United States Patent
Racenet et al.

(10) Patent No.: US 7,721,935 B2
(45) Date of Patent: May 25, 2010

(54) SURGICAL STAPLING DEVICE

(75) Inventors: David C. Racenet, Litchfield, CT (US); Ralph Stearns, Bozrah, CT (US); John W. Beardsley, Hamden, CT (US); Philip Roy, Hamden, CT (US); Lee Ann Olson, Wallingford, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 589 days.

(21) Appl. No.: 11/543,640

(22) Filed: Oct. 3, 2006

(65) Prior Publication Data

US 2007/0034670 A1    Feb. 15, 2007

Related U.S. Application Data

(62) Division of application No. 10/871,342, filed on Jun. 17, 2004, now Pat. No. 7,159,750.

(60) Provisional application No. 60/479,379, filed on Jun. 17, 2003.

(51) Int. Cl.
*A61B 17/04* (2006.01)

(52) U.S. Cl. ............... 227/180.1; 227/175.1; 606/219

(58) Field of Classification Search ... 227/175.1–180.1; 606/130, 219, 131, 151
See application file for complete search history.

(56) References Cited

U.S. PATENT DOCUMENTS

| | | | |
|---|---|---|---|
| 3,079,606 | A | 3/1963 | Bobrov et al. |
| 3,490,675 | A | 1/1970 | Green et al. |
| 3,777,538 | A | 12/1973 | Weatherly et al. |
| 4,027,510 | A | 6/1977 | Hiltebrandt |
| 4,086,926 | A | 5/1978 | Green et al. |
| 4,244,372 | A | 1/1981 | Kapitanov et al. |
| 4,429,695 | A | 2/1984 | Green |
| 4,505,414 | A | 3/1985 | Filipi |
| 4,589,413 | A | 5/1986 | Malyshev et al. |
| 4,602,634 | A | 7/1986 | Barkley |
| 4,608,981 | A | 9/1986 | Rothfuss et al. |
| 4,610,383 | A | 9/1986 | Rothfuss et al. |

(Continued)

FOREIGN PATENT DOCUMENTS

AU          5476586          9/1986

(Continued)

*Primary Examiner*—Paul R Durand

(57) ABSTRACT

A surgical device is disclosed which includes a handle portion, a central body portion and a single use loading unit, or "SULU". The SULU includes a proximal body portion, an intermediate pivot member and a tool assembly. The intermediate pivot member is pivotally secured to the proximal body portion about a first pivot axis and the tool assembly is pivotally secured to the intermediate pivot member about a second pivot axis which is orthogonal to the first pivot axis. The SULU includes a plurality of articulation links which are operably connected to the tool assembly by non-rigid links. The articulation links are adapted to releasably engage articulation links positioned in the central body portion. The body portion articulation links are connected to an articulation actuator which is supported for omni-directional movement to effect articulation of the tool assembly about the first and second axes. The handle portion includes a spindle and barrel assembly drive mechanism for advancing and retracting a drive member positioned in the tool assembly. In one embodiment, the tool assembly includes a cartridge assembly having a plurality of staples and an anvil assembly.

15 Claims, 44 Drawing Sheets

U.S. PATENT DOCUMENTS

| | | | |
|---|---|---|---|
| 4,633,861 A | 1/1987 | Chow et al. | |
| 4,633,874 A | 1/1987 | Chow et al. | |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,892,244 A | 1/1990 | Fox et al. | |
| 4,978,049 A | 12/1990 | Green | |
| 4,991,764 A | 2/1991 | Mericle | |
| 5,040,715 A | 8/1991 | Green et al. | |
| 5,065,929 A | 11/1991 | Schulze et al. | |
| 5,074,454 A | 12/1991 | Peters | |
| 5,083,695 A | 1/1992 | Foslien et al. | |
| 5,084,057 A | 1/1992 | Green et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,170,925 A | 12/1992 | Madden et al. | |
| 5,171,247 A | 12/1992 | Hughetti et al. | |
| 5,246,156 A | 9/1993 | Rothfuss et al. | |
| RE34,519 E | 1/1994 | Fox et al. | |
| 5,282,807 A | 2/1994 | Knoepfler | |
| 5,307,976 A | 5/1994 | Olson et al. | |
| 5,312,023 A * | 5/1994 | Green et al. | 227/175.1 |
| 5,318,221 A | 6/1994 | Green et al. | |
| 5,326,013 A | 7/1994 | Green et al. | |
| 5,328,077 A | 7/1994 | Lou | |
| 5,332,142 A | 7/1994 | Robinson et al. | |
| 5,336,232 A | 8/1994 | Green et al. | |
| 5,358,506 A | 10/1994 | Green et al. | |
| 5,364,002 A | 11/1994 | Green et al. | |
| 5,364,003 A | 11/1994 | Williamson, IV | |
| 5,376,095 A | 12/1994 | Ortiz | |
| 5,381,943 A | 1/1995 | Allen et al. | |
| 5,382,255 A | 1/1995 | Castro et al. | |
| 5,383,880 A | 1/1995 | Hooven | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,407,293 A | 4/1995 | Crainich | |
| 5,413,268 A | 5/1995 | Green et al. | |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A * | 1/1996 | Fontayne | 227/178.1 |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A * | 10/1996 | Huitema et al. | 606/159 |
| 5,564,615 A | 10/1996 | Bishop et al. | |
| 5,571,116 A | 11/1996 | Bolanos et al. | |
| 5,573,543 A | 11/1996 | Akopov et al. | |
| 5,575,799 A | 11/1996 | Bolanos et al. | |
| 5,577,654 A | 11/1996 | Bishop | |
| 5,579,107 A | 11/1996 | Wright et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,094 A | 3/1997 | Clark et al. | |
| 5,607,095 A * | 3/1997 | Smith et al. | 227/177.1 |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A * | 9/1997 | Bishop et al. | 606/143 |
| 5,662,666 A | 9/1997 | Onuki et al. | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,690,269 A * | 11/1997 | Bolanos et al. | 227/176.1 |
| 5,692,668 A | 12/1997 | Schulze et al. | |
| 5,697,542 A | 12/1997 | Knodel et al. | |

| | | |
|---|---|---|
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,954,259 A | 9/1999 | Viola et al. |
| 5,980,510 A | 11/1999 | Tsonton et al. |
| 6,004,335 A | 12/1999 | Vaitekunas et al. |
| 6,010,054 A | 1/2000 | Johnson et al. |
| 6,024,748 A * | 2/2000 | Manzo et al. ............... 606/153 |
| 6,032,849 A | 3/2000 | Mastri et al. |
| 6,079,606 A | 6/2000 | Milliman et al. |
| 6,109,500 A | 8/2000 | Alli et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,830,174 B2 * | 12/2004 | Hillstead et al. ......... 227/175.1 |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B2 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,159,750 B2 | 1/2007 | Racenet et al. |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069565 A1 | 6/2002 | Liao |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |

| | | | | | |
|---|---|---|---|---|---|
| 2004/0004105 A1 | 1/2004 | Jankowski | DE | 2903159 | 1/1980 |
| 2004/0007608 A1 | 1/2004 | Ehrenfels | DE | 3114135 | 10/1982 |
| 2004/0050902 A1 | 3/2004 | Green et al. | DE | 4213426 | 10/1992 |
| 2004/0093029 A1 | 5/2004 | Zubik et al. | DE | 4300307 | 7/1994 |
| 2004/0094597 A1 | 5/2004 | Whitman | EP | 0041022 | 12/1981 |
| 2004/0108357 A1 | 6/2004 | Milliman | EP | 0136950 | 4/1985 |
| 2004/0149802 A1 | 8/2004 | Whitman | EP | 0140552 | 5/1985 |
| 2004/0173659 A1 | 9/2004 | Green | EP | 0156774 | 10/1985 |
| 2004/0199181 A1 | 10/2004 | Knodel et al. | EP | 0216532 | 4/1987 |
| 2004/0232199 A1 | 11/2004 | Shelton, IV et al. | EP | 0220029 | 4/1987 |
| 2004/0232200 A1 | 11/2004 | Shelton, IV et al. | EP | 0213817 | 11/1987 |
| 2004/0232201 A1 | 11/2004 | Wenchell | EP | 0273468 | 7/1988 |
| 2004/0243151 A1 | 12/2004 | Demmy | EP | 0324166 | 7/1989 |
| 2004/0267310 A1 | 12/2004 | Racenet | EP | 0324635 | 7/1989 |
| 2005/0006429 A1 | 1/2005 | Wales | EP | 0324637 | 7/1989 |
| 2005/0006430 A1 | 1/2005 | Wales | EP | 0324638 | 7/1989 |
| 2005/0006431 A1 | 1/2005 | Shelton, IV et al. | EP | 0369324 | 5/1990 |
| 2005/0006432 A1 | 1/2005 | Racenet | EP | 0373762 | 6/1990 |
| 2005/0006433 A1 | 1/2005 | Milliman | EP | 0380025 | 8/1990 |
| 2005/0006434 A1 | 1/2005 | Wales et al. | EP | 0399701 | 11/1990 |
| 2005/0023324 A1 | 2/2005 | Doll et al. | EP | 0449394 | 10/1991 |
| 2005/0023325 A1 | 2/2005 | Gresham | EP | 0484677 | 5/1992 |
| 2005/0067457 A1 | 3/2005 | Shelton | EP | 0489436 | 6/1992 |
| 2005/0067458 A1 | 3/2005 | Swayze et al. | EP | 0503662 | 9/1992 |
| 2005/0067459 A1 | 3/2005 | Swayze et al. | EP | 0514139 | 11/1992 |
| 2005/0067460 A1 | 3/2005 | Milliman | EP | 0536903 | 4/1993 |
| 2005/0072827 A1 | 4/2005 | Mollenauer | EP | 0537572 | 4/1993 |
| 2005/0103819 A1 | 5/2005 | Racenet | EP | 0539762 | 5/1993 |
| 2005/0119669 A1 | 6/2005 | Demmy | EP | 0545029 | 6/1993 |
| 2005/0127131 A1 | 6/2005 | Mastri | EP | 0552050 | 7/1993 |
| 2005/0165415 A1 | 7/2005 | Wales | EP | 0552423 | 7/1993 |
| 2005/0173490 A1 | 8/2005 | Shelton, IV | EP | 0579038 | 1/1994 |
| 2005/0178813 A1 | 8/2005 | Swayze et al. | EP | 0589306 | 3/1994 |
| 2005/0184123 A1 | 8/2005 | Scirica et al. | EP | 0591946 | 4/1994 |
| 2005/0184124 A1 | 8/2005 | Scirica et al. | EP | 0592243 | 4/1994 |
| 2005/0184125 A1 | 8/2005 | Marczyk | EP | 0593920 | 4/1994 |
| 2005/0184126 A1 | 8/2005 | Green et al. | EP | 0598202 | 5/1994 |
| 2005/0189397 A1 | 9/2005 | Jankowski | EP | 0598579 | 5/1994 |
| 2005/0216055 A1 | 9/2005 | Scirica et al. | EP | 0621006 | 10/1994 |
| 2005/0263562 A1 | 12/2005 | Shelton, IV et al. | EP | 0621009 | 10/1994 |
| 2005/0279804 A1 | 12/2005 | Scirica et al. | EP | 0656188 | 6/1995 |
| 2006/0000867 A1 | 1/2006 | Shelton, IV et al. | EP | 0365153 | 8/1995 |
| 2006/0000868 A1 | 1/2006 | Shelton, IV et al. | EP | 0666057 | 8/1995 |
| 2006/0011699 A1 | 1/2006 | Olson et al. | EP | 0705571 | 4/1996 |
| 2006/0016853 A1 | 1/2006 | Racenet | FR | 2542188 | 9/1984 |
| 2006/0022014 A1 | 2/2006 | Shelton, IV et al. | FR | 2660851 | 10/1991 |
| 2006/0022015 A1 | 2/2006 | Shelton, IV et al. | FR | 2681775 | 10/1991 |
| 2006/0049230 A1 | 3/2006 | Shelton, IV et al. | GB | 1352554 | 4/1971 |
| 2006/0062136 A1* | 3/2006 | Kikuchi et al. ......... 369/275.1 | GB | 1452185 | 10/1976 |
| 2006/0124688 A1 | 6/2006 | Racenet et al. | GB | 1555455 | 11/1979 |
| 2006/0151567 A1 | 7/2006 | Roy | GB | 2048685 | 12/1980 |
| 2006/0151568 A1 | 7/2006 | Weller et al. | GB | 2070499 | 9/1981 |
| 2006/0175375 A1 | 8/2006 | Shelton, IV et al. | GB | 2141066 | 12/1984 |
| 2006/0180634 A1 | 8/2006 | Shelton, IV et al. | GB | 2165559 | 4/1986 |
| 2006/0201990 A1 | 9/2006 | Mastri et al. | JP | 51-149985 | 5/1975 |
| 2006/0201991 A1 | 9/2006 | Mastri et al. | SU | 728848 | 5/1977 |
| 2006/0226195 A1 | 10/2006 | Scirica et al. | SU | 659146 | 4/1979 |
| 2006/0226196 A1 | 10/2006 | Hueil et al. | SU | 980703 | 12/1982 |
| 2006/0278680 A1 | 12/2006 | Viola et al. | SU | 990220 | 1/1983 |
| 2006/0278681 A1 | 12/2006 | Viola et al. | WO | WO 89/10094 | 11/1989 |
| 2006/0289600 A1 | 12/2006 | Wales et al. | WO | WO9210976 | 7/1992 |
| 2006/0289602 A1 | 12/2006 | Wales et al. | WO | WO 9308754 | 5/1993 |
| | | | WO | WO8302247 | 7/1993 |
| | FOREIGN PATENT DOCUMENTS | | WO | WO 9314706 | 8/1993 |
| DE | 2744824 | 4/1978 | * cited by examiner | | |

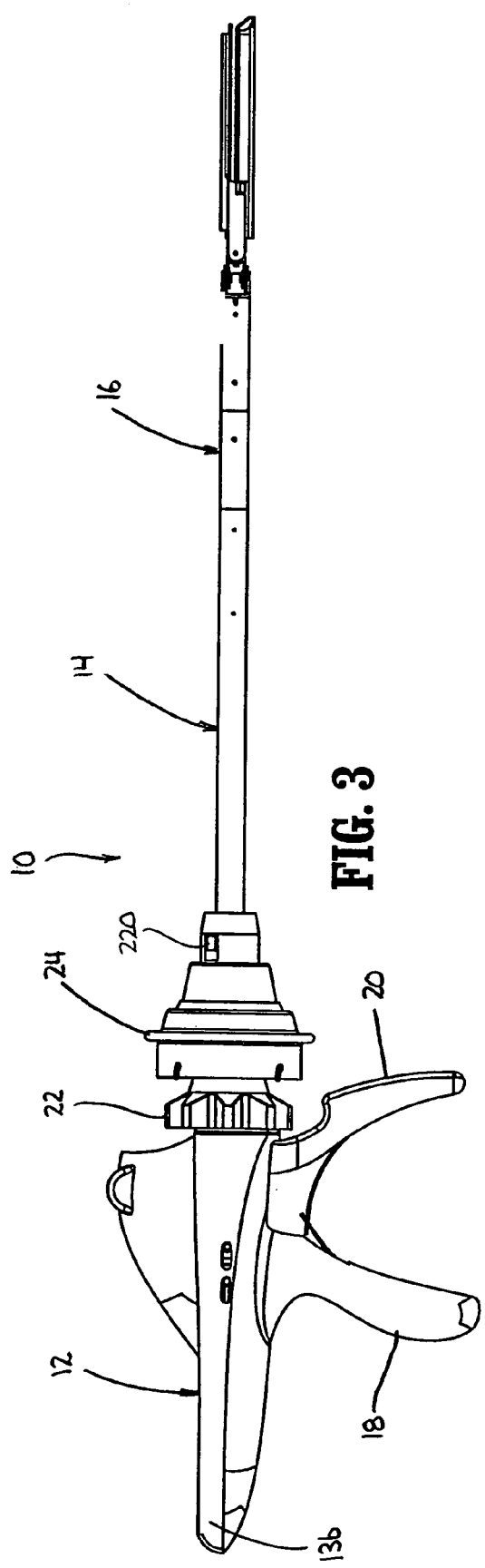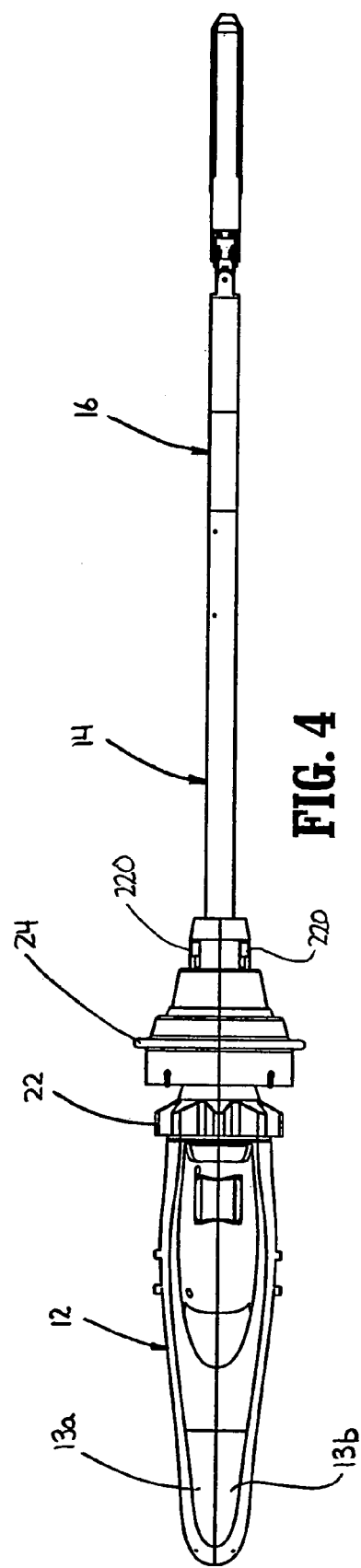

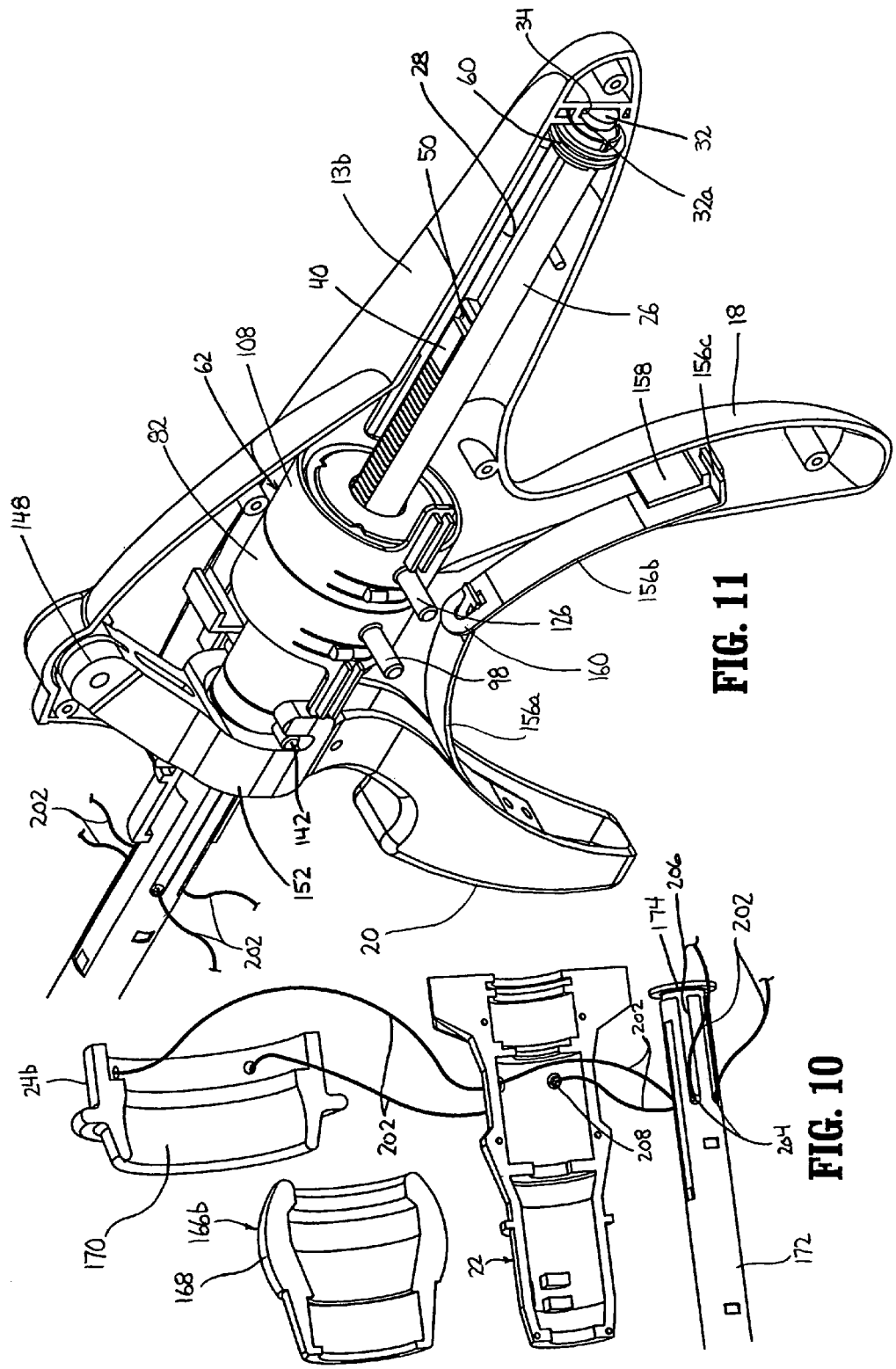

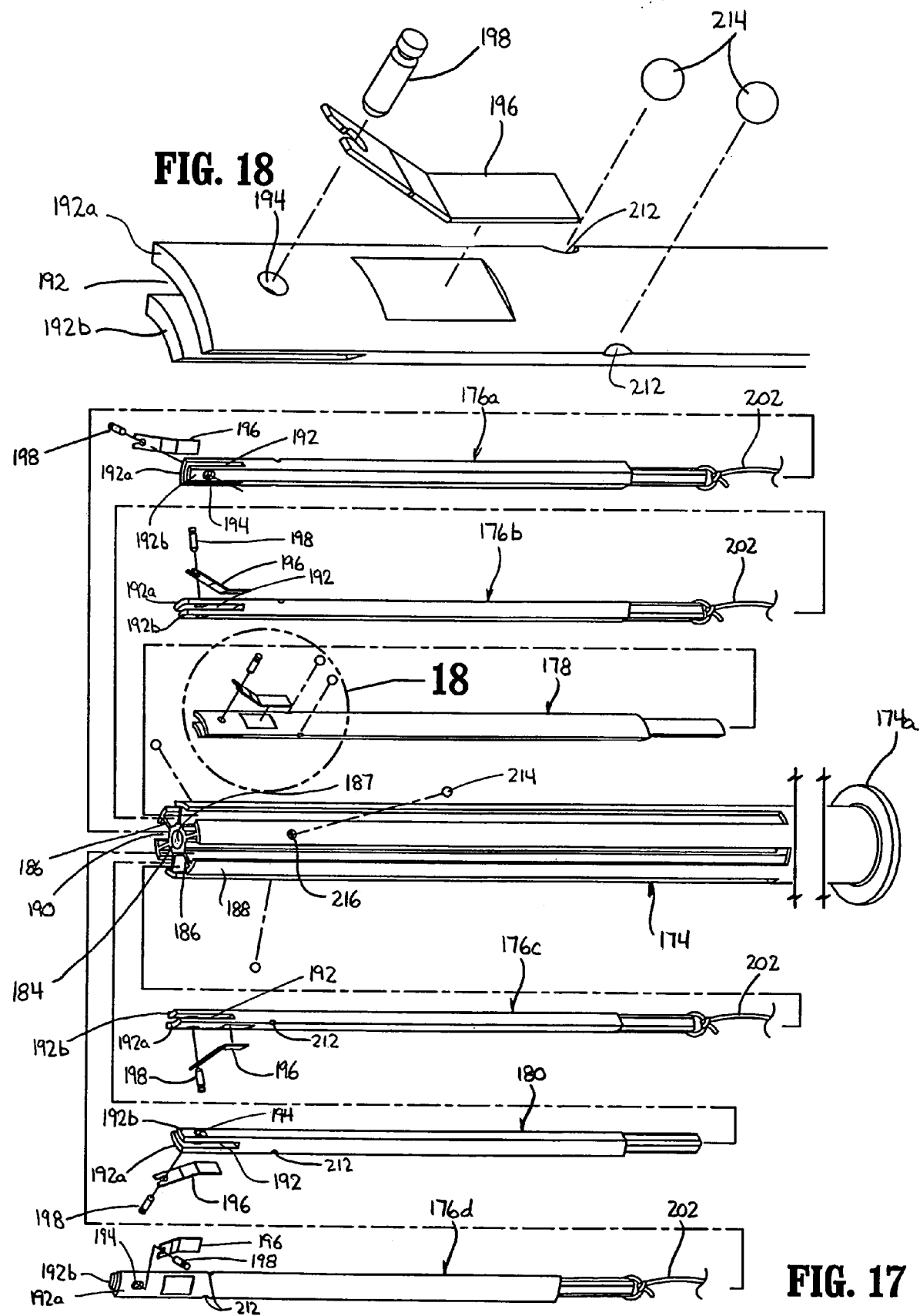

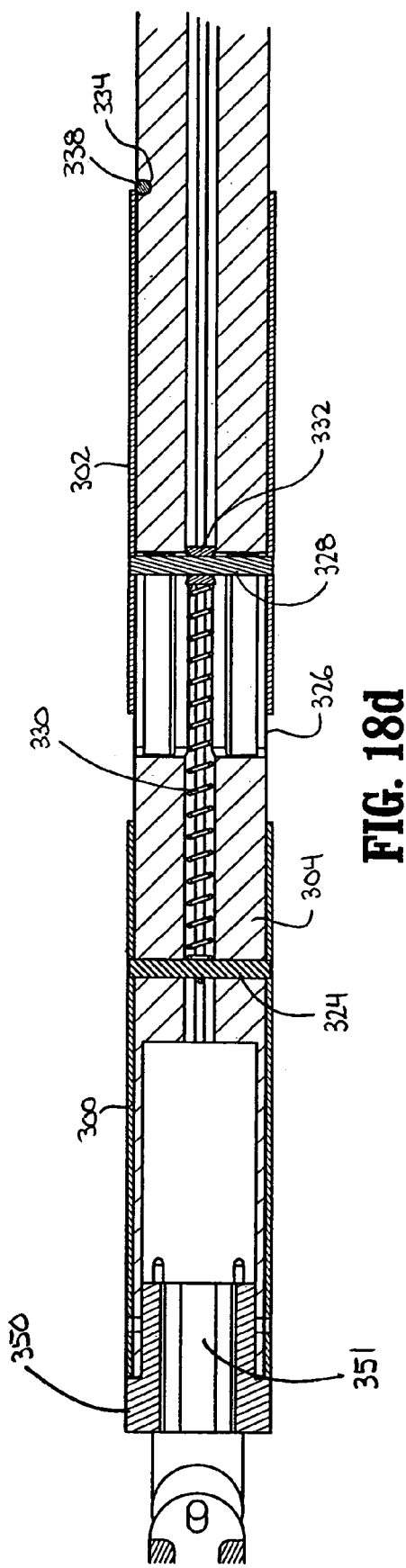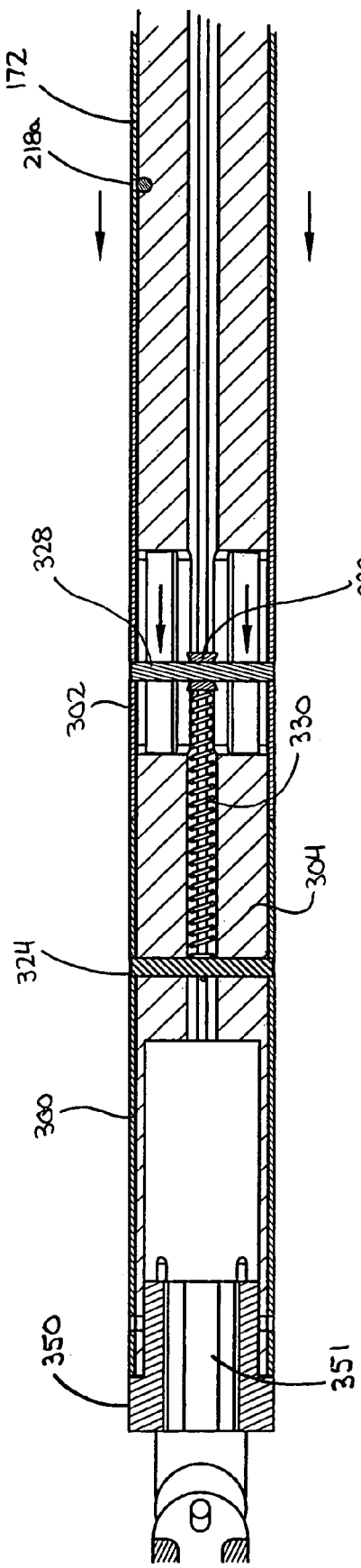

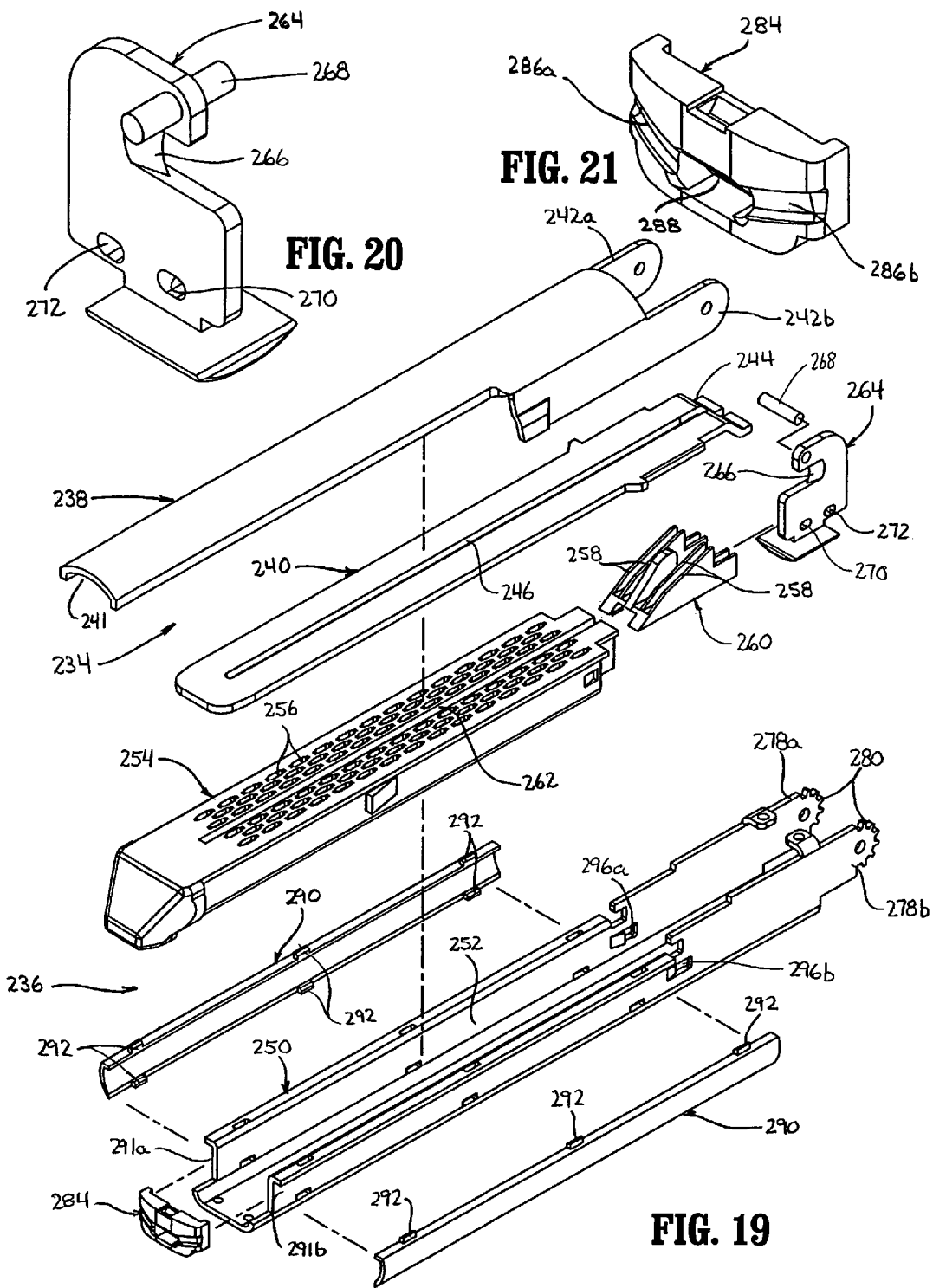

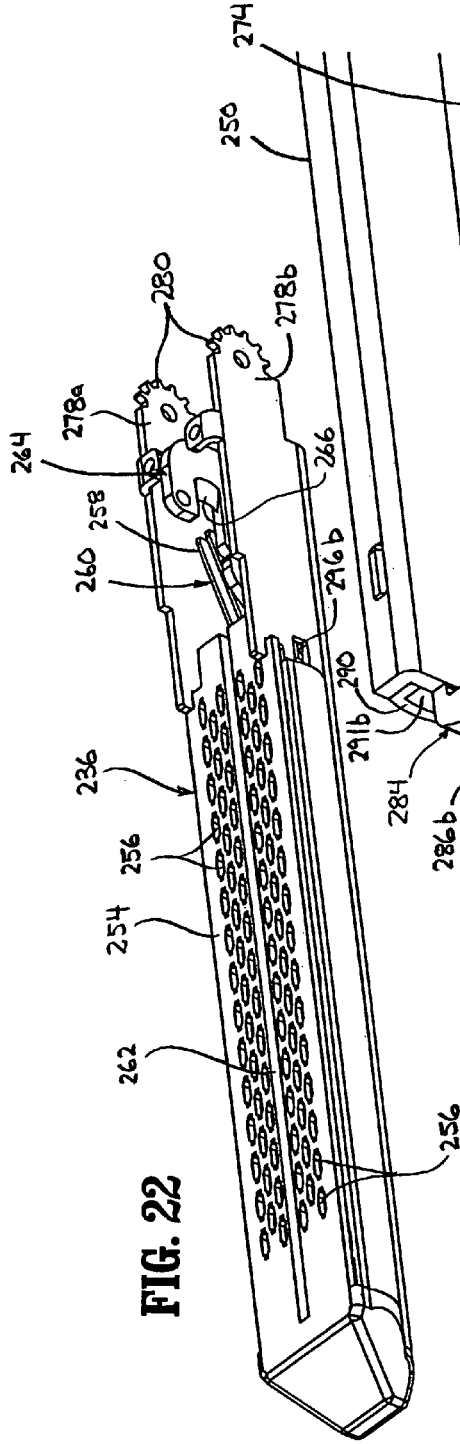
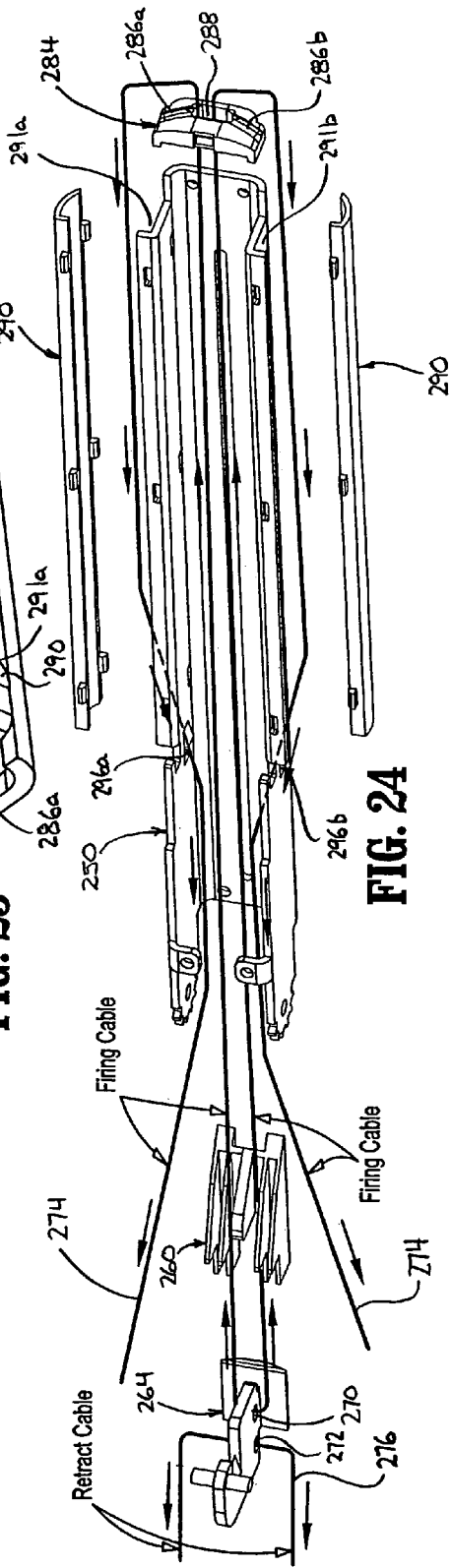
FIG. 22
FIG. 23
FIG. 24

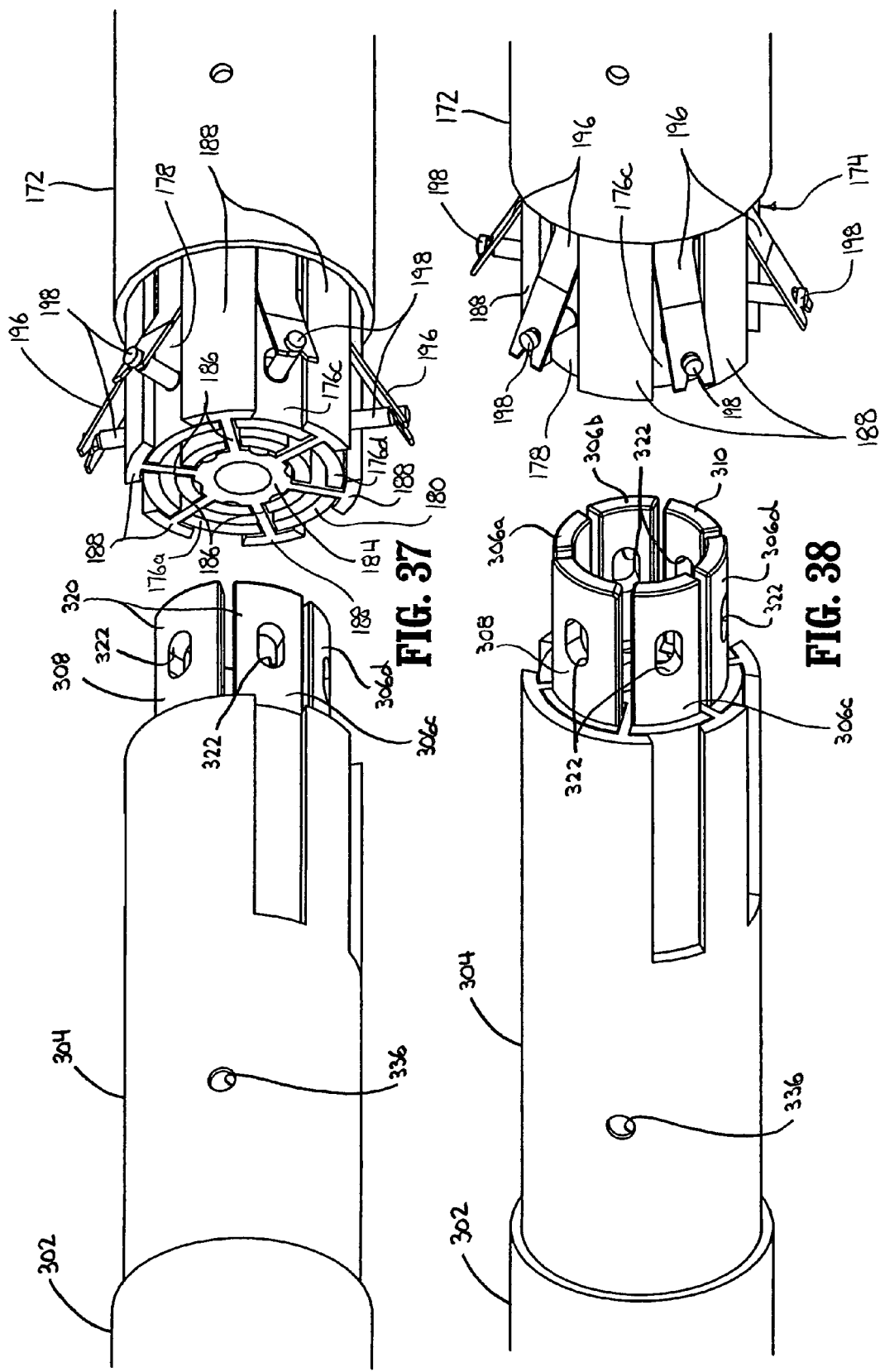

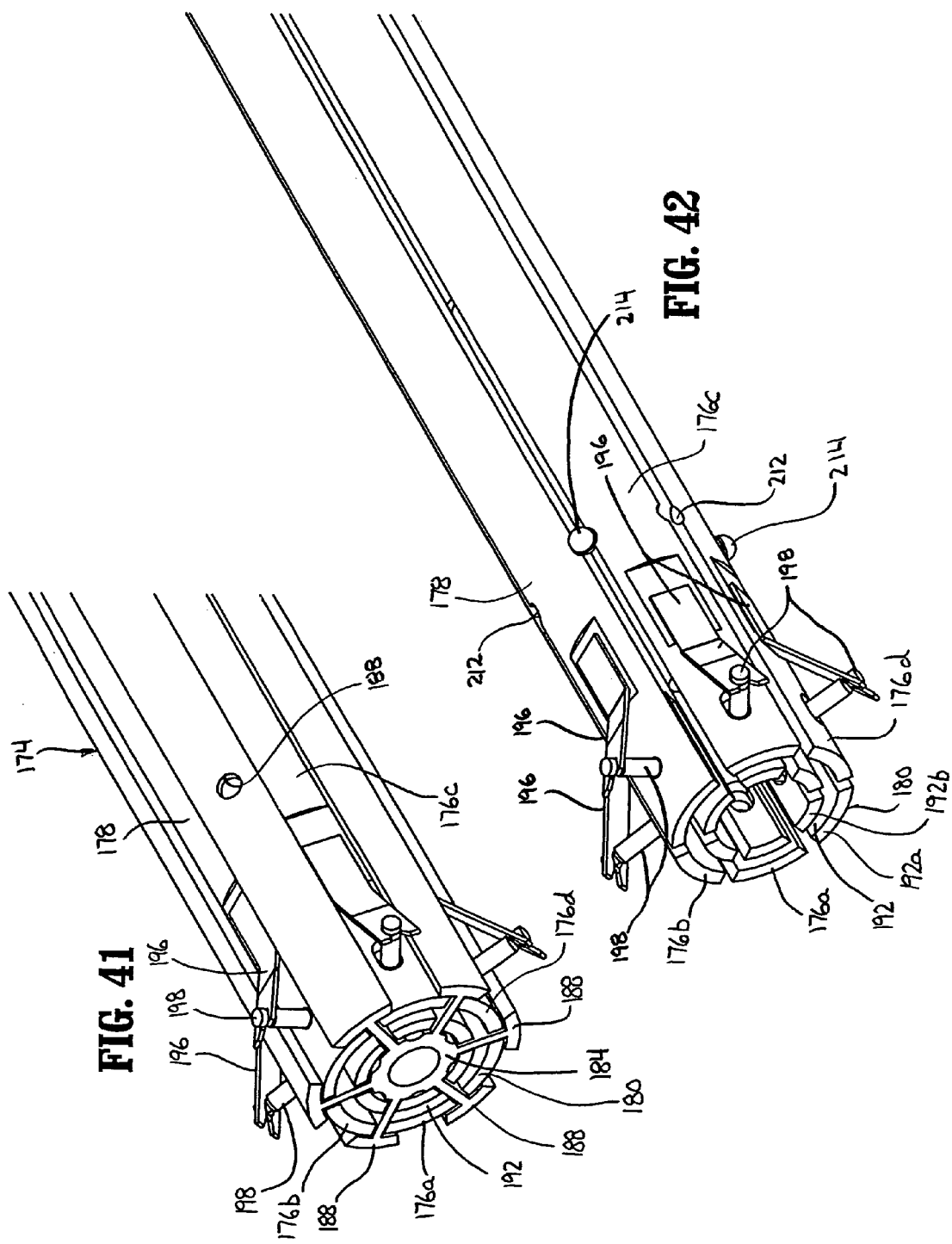

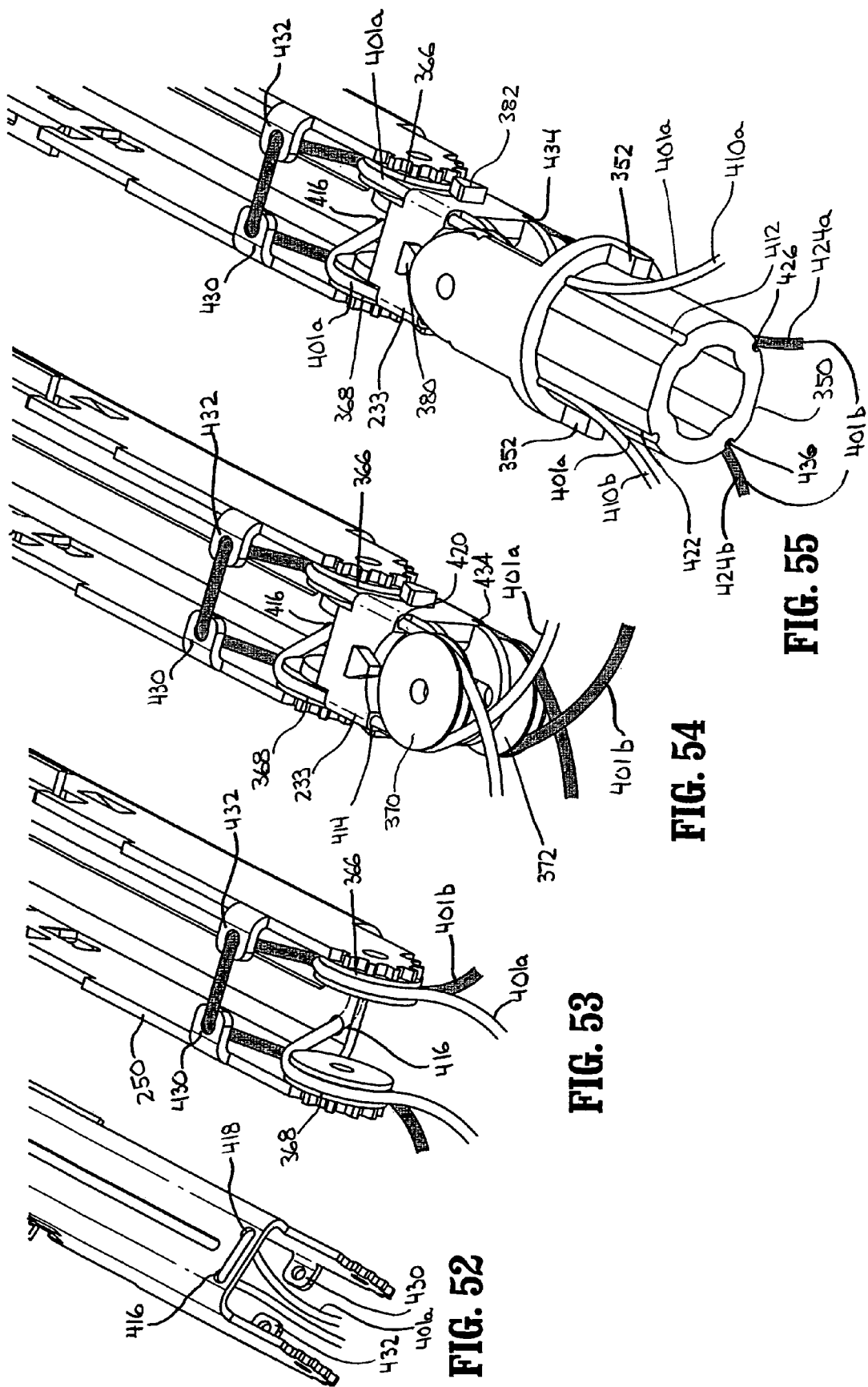

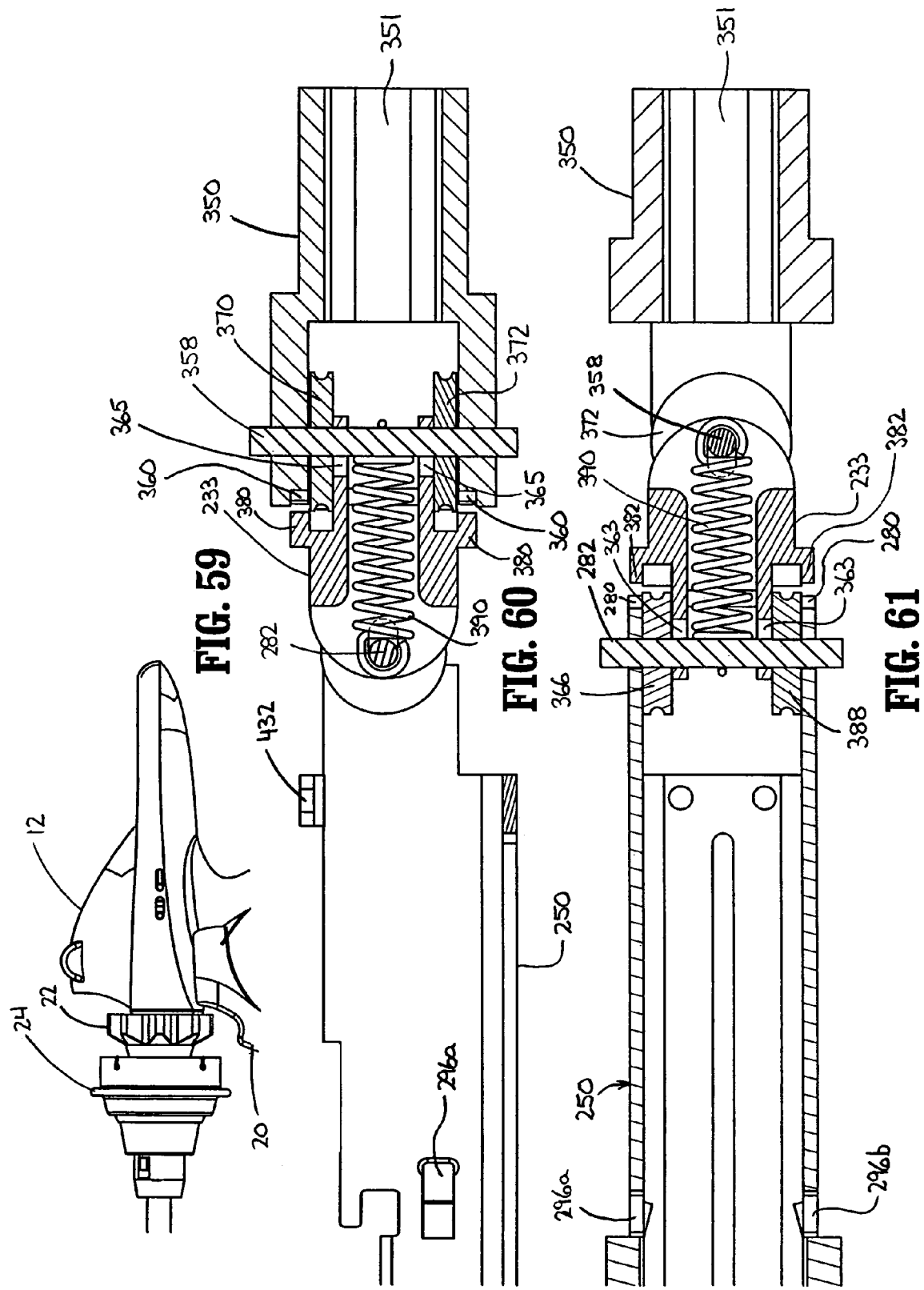

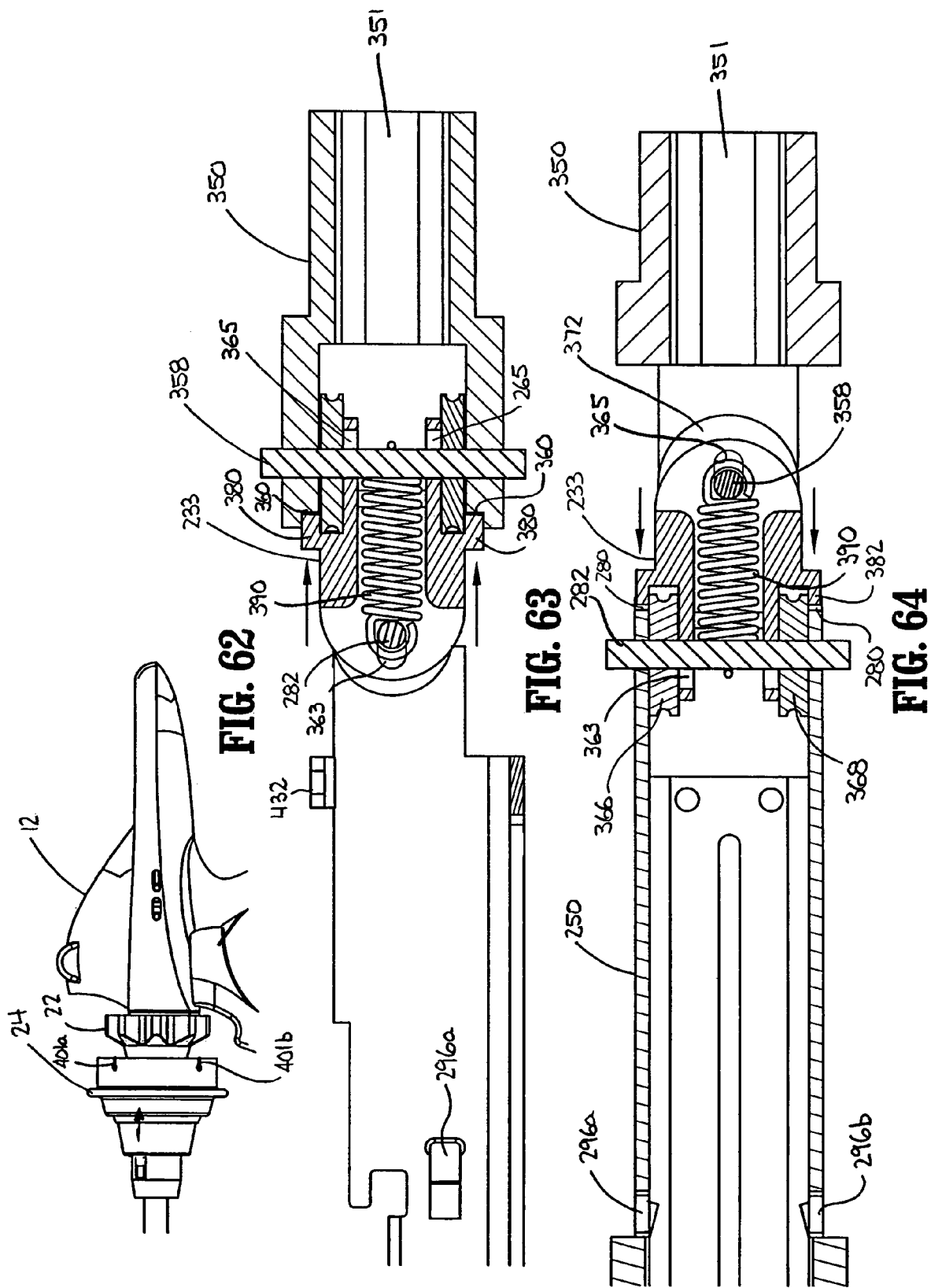

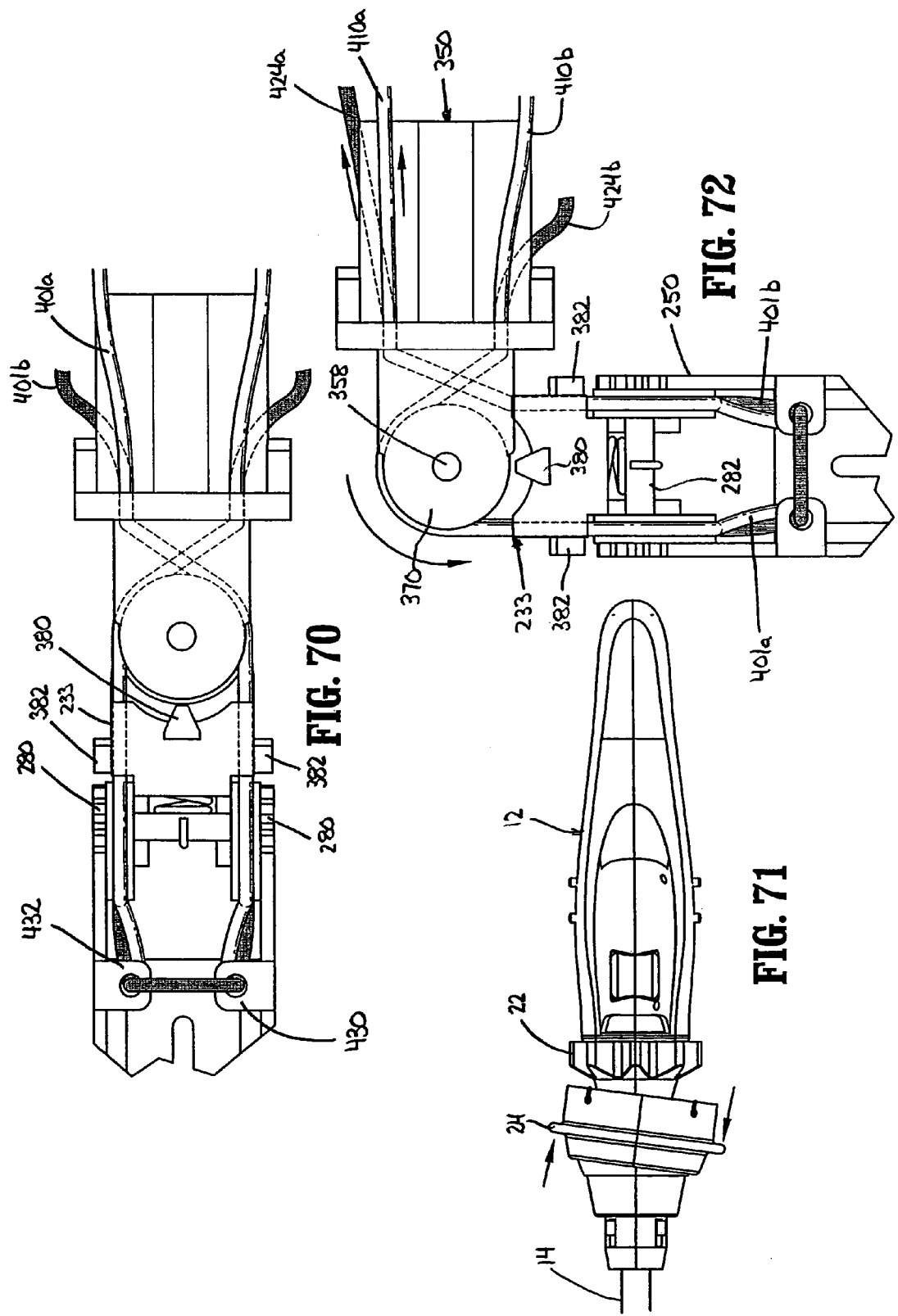

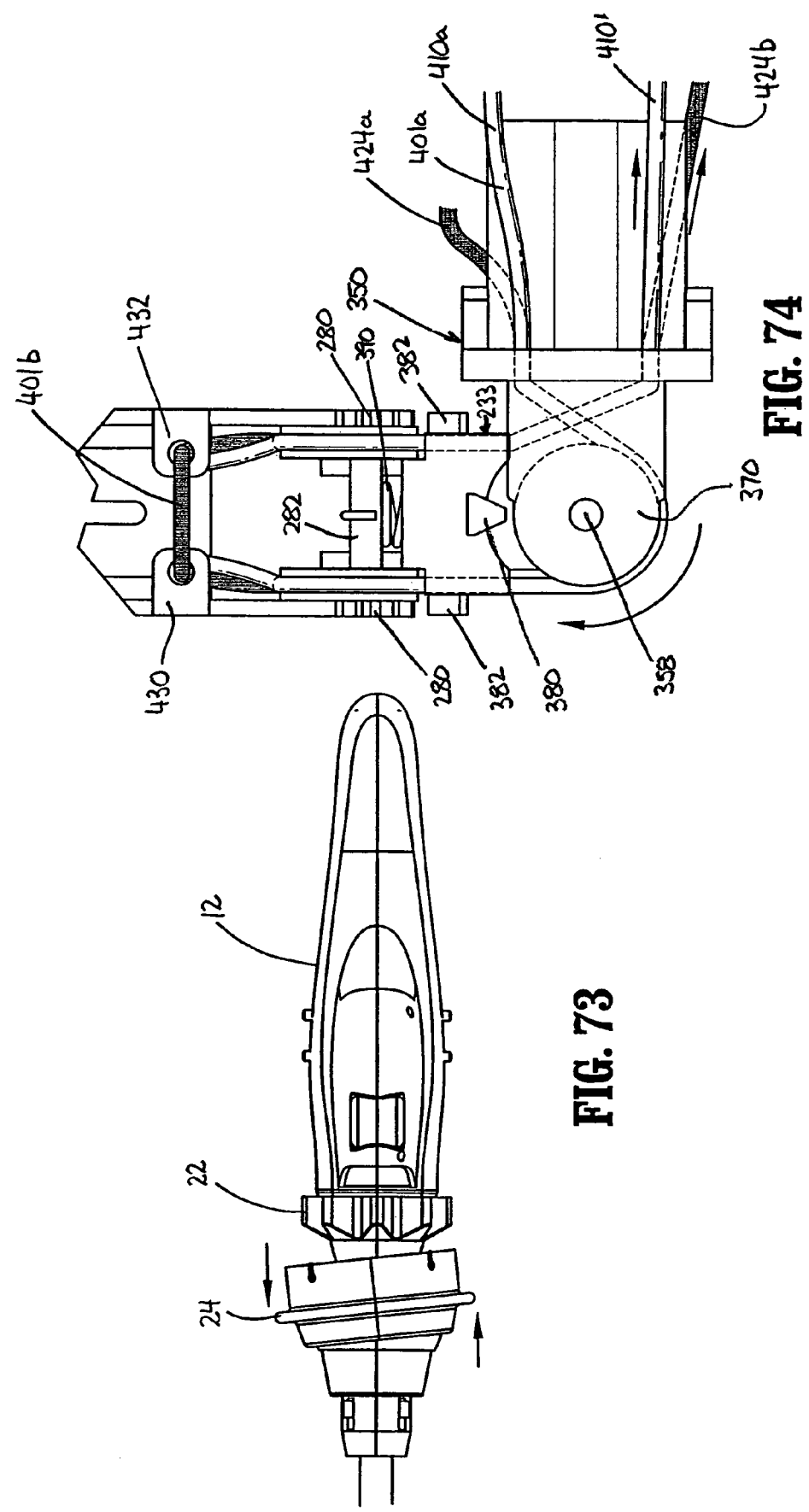

SURGICAL STAPLING DEVICE

RELATED APPLICATIONS

This application is a divisional of U.S. patent application Ser. No. 10/871,342 filed Jun. 17, 2004 now U.S. Pat. No. 7,159,750 which claims priority to U.S. Provisional Patent Application Ser. No. 60/479,379 filed Jun. 17, 2003, the disclosures of which are incorporated herein in their entirety by this reference.

BACKGROUND

1. Technical Field

The present disclosure relates to a surgical stapling device and, more particularly, to an endoscopic surgical stapling device having a tool assembly which is articulatable about first and second perpendicular axes.

2. Background of Related Art

Surgical devices wherein tissue is first grasped or clamped between opposing jaw structure and then joined by surgical fasteners are well known in the art. In some instruments a knife is provided to cut the tissue which has been joined be the fasteners. The fasteners are typically in the form of surgical staples but two part, including polymeric, fasteners can also be utilized.

Instruments for this purpose can include two elongated members which are respectively used to capture or clamp tissue. Typically, one of the members carries a staple cartridge which houses a plurality of staples arranged, for example, in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut the stapled tissue between the rows of staples. Such staplers are disclosed in U.S. Pat. Nos. 6,250,532 and 6,241,139 which are incorporated herein be reference in their entirety.

In endoscopic or laparoscopic procedures, surgery is performed through small incisions or through small diameter cannulas inserted through small entrance wounds in the skin. Due to the limited degree of motion of an instrument when it is positioned through the skin, it may be quite difficult for a surgeon to manipulate the tool assembly of the instrument to access and/or clamp tissue. To overcome this problem, instruments having rotatable endoscopic body portions and rotatable and/or articulatable tool assemblies have been developed and are commercially available. Although these instruments provide significant improvements in the endoscopic tool art, further improvements that may decrease the time required for surgical procedures by allowing surgeons to more quickly access tissue are desired.

Accordingly, a continuing need exists for an endoscopic or laparoscopic surgical device having a tool assembly which can be quickly and easily manipulated to an infinite number of orientations to access, clamp and/or cut tissue.

SUMMARY

In accordance with the present disclosure, a surgical stapling device is provided which includes a handle portion, an elongated central body portion and a Single Use Loading Unit ("SULU") or Disposable Loading Unit ("DLU"). The elongated body portion is rotatably secured to the handle portion. The SULU includes a proximal body portion, an intermediate pivot member and a tool assembly. The intermediate pivot member is pivotally connected to the proximal body portion about a first axis and pivotally connected to the tool assembly about a second axis substantially orthogonal to the first axis. As such, the intermediate pivot member is able to articulate in relation to the proximal body portion and tool assembly is able to pivot with respect to the intermediate pivot member. Thus, the tool assembly is able to be pivoted about multiple axes in relation to the elongated central body portion of the device. Since the elongated central body portion of the device is also rotatable in relation to the handle portion of the device, the capability of articulation of the tool assembly about multiple axes allows a surgeon to quickly and easily position the tool assembly at an infinite number of orientations to facilitate operation on body tissue.

In another aspect of the disclosure, the surgical stapling device includes an articulation actuator which is supported on a semi-spherical base member for omni-directional or universal movement. A plurality of articulation links have a first end operably connected to the articulation actuator and a second end adapted to be releasably connected to articulation links of the SULU. The articulation links of the SULU are operably connected to the tool assembly by cables or non-rigid links such that the articulation actuator can be manipulated to articulate the tool assembly about either or both of the first and second axes.

In another aspect of the invention, the handle portion includes a drive mechanism for moving a firing link and a retraction link for effecting operation of the tool assembly. The drive mechanism includes a spindle supported within the handle portion and a barrel assembly slidably positioned about the spindle. The spindle includes a first guide track for receiving a firing rack and a second diametrically disposed guide track for slidably receiving a retraction rack. The barrel assembly includes a firing pawl which is movable into engagement with the firing rack and a retraction pawl which is movable into engagement with the retraction rack. A first shift ring assembly is provided to selectively position the firing and retraction pawls in relation to the firing and retraction racks, respectively. A handle portion trigger is provided to move the barrel assembly about and along the spindle to selectively move the firing rack or retraction rack to operate the tool assembly.

In yet another aspect of the disclosure, the tool assembly is a stapling device and the barrel assembly includes a grasper pawl which is movable into engagement with the firing rack to allow the tool assembly to be operated in a grasper mode. More specifically, the grasper pawl is controlled by a second shift ring assembly and is selectively movable into engagement with the firing rack to allow the firing rack to move a distance which will, upon operation of the movable trigger, effect approximation of cartridge and anvil assemblies of the tool assembly but will not affect firing of staples.

In yet another embodiment of the disclosure, the tool assembly includes a cartridge assembly and an anvil assembly. A drive assembly including a knife bar and an actuation sled are translatable through the tool assembly to simultaneously staple and cut tissue positioned between the cartridge and anvil assemblies. A firing cable and a retract cable each have a first portion secured to the drive assembly. The firing cable has a proximal end secured to a firing link of the SULU which is adapted to be releasably connected to a firing link of the central body portion. The firing link of the central body portion is operably connected to the firing rack such that proximal movement of the firing rack effects distal translation of the drive assembly through the cartridge assembly. The retract cable has a proximal end connected to a retraction link of the SULU. The retraction link of the SULU is adapted to be connected to the retraction link of the central body portion of the device which is operably connected to the retraction rack such that proximal movement of the retraction rack effects proximal movement of the drive assembly.

In another aspect of the disclosure, a novel connection mechanism is provided for securing the SULU to the elongated central body portion of the stapling device. The connection mechanism facilitates releasable attachment of a SULU having a non-rigid cable driven drive assembly to a stapling device.

It is an object of this disclosure to provide a surgical device having a removable SULU which includes an articulation and/or drive mechanism having non-rigid links.

It is another object of this disclosure to provide a surgical stapling device having a rotatable central body portion and a tool assembly including a cartridge assembly and an anvil assembly which is pivotal about first and second axes which are substantially orthogonal to each other.

It is yet another object of this disclosure to provide a handle portion having a spindle and barrel assembly which facilitates selective operation of an operating member or drive member in a firing or operating mode, a retraction mode and a grasping mode.

BRIEF DESCRIPTION OF THE DRAWINGS

Embodiments of the presently disclosed surgical stapling device are disclosed herein with reference to the drawings wherein:

FIG. 3 is a side view of the surgical stapling device shown in FIG. 2;

FIG. 4 is a top view of the surgical stapling device shown in FIG. 3;

FIG. 10 is a side perspective view with parts separated of the proximal end of the central body portion, one half-section of the articulation actuator and actuator base member and one half-section of the rotation control member of the surgical stapling device shown in FIG. 8;

FIG. 11 is a side perspective view from the proximal end of the handle portion and the proximal portion of the central body portion of the surgical stapling device shown in FIG. 8 with a handle portion half-section, the articulation actuator and rotation control member removed;

FIG. 17 is a side perspective view with parts separated of the internal components of the central body portion of the surgical stapling shown in FIG. 8;

FIG. 18 is an enlarged view of the indicated area of detail shown in FIG. 17;

FIG. 18a is a side perspective view of the SULU of the surgical stapling device shown in FIG. 8 with the proximal body portion of the SULU shown with parts separated;

FIG. 18b is a cross-sectional view taken along section lines 18b-18b of FIG. 18a;

FIG. 18c is a cross-sectional view taken along section lines 18c-18c of FIG. 18a;

FIG. 18d is a cross-sectional view taken along section lines 18d-18d of FIG. 18a;

FIG. 18e is a cross-sectional view of the proximal body portion of the SULU shown in FIG. 18 during attachment of the SULU to the central body portion of a surgical stapling device;

FIG. 19 is a side perspective view with parts separated of the tool assembly of the SULU shown in FIG. 18a with mess cables not shown;

FIG. 20 is an enlarged side perspective view of the knife bar of the SULU shown in FIG. 19;

FIG. 21 is an enlarged side perspective view from the distal end of the guide cap of the SULU shown in FIG. 19;

FIG. 22 is an enlarged side perspective view from above of the cartridge assembly of the SULU shown in FIG. 19, assembled;

FIG. 23 is an enlarged side perspective view of a portion of the distal end of the cartridge assembly shown in FIG. 22 with the cartridge and nose cap removed;

FIG. 24 is a top perspective view from one side of the cartridge assembly shown in FIG. 22 with parts separated and the firing cable and retract cable shown schematically;

FIG. 37 is a perspective view from the distal end of the proximal portion of the SULU and the distal portion of the central body portion of the surgical stapling device shown in FIG. 8 prior to attachment of the SULU to the central body portion;

FIG. 38 is a perspective view from the proximal end of the proximal portion of the SULU and the distal portion of the central body portion shown in FIG. 37;

FIG. 41 is a perspective view of the distal end of the central body portion of the surgical stapling device shown in FIG. 8 with the outer tube removed;

FIG. 42 is a perspective view from the distal end of the central body portion shown in FIG. 41 with the hub member removed;

FIG. 52 is a bottom perspective view of the proximal end of the cartridge carrier portion shown in FIG. 51 with an articulation cable attached thereto;

FIG. 53 is a top perspective view of the proximal end of the cartridge carrier portion shown in FIG. 52 with a pair of rotatable pulleys, and articulation cables thereon;

FIG. 54 is a top perspective view of the proximal end of the cartridge carrier portion shown in FIG. 53 with the intermediate pivot and a second pair of rotatable pulleys attached thereto;

FIG. 55 is a top perspective view of the proximal end of the cartridge carrier portion shown in FIG. 54 with the mounting member secured to the intermediate pivot;

FIG. 59 is a side cutaway view of the handle portion and central body portion of the surgical stapling device shown in FIG. 8 prior to articulation of the surgical stapling device;

FIG. 60 is a side cross-sectional view of the carrier portion, intermediate pivot assembly and mounting member of the surgical stapling device shown in FIG. 59;

FIG. 61 is a top cross-sectional view of the carrier portion, intermediate pivot and mounting member shown in FIG. 60;

FIG. 62 is a side cutaway view of the handle portion and central body portion of the surgical stapling device shown in FIG. 59 with the articulation actuator moved proximally;

FIG. 63 is a side cross-sectional view of the carrier portion, intermediate pivot and mounting member of the surgical stapling device shown in FIG. 62;

FIG. 64 is a top cross-sectional view of the carrier portion, intermediate pivot and mounting member of the SULU of the surgical stapling device shown in FIG. 62;

FIG. 70 is a bottom view of the carrier portion, intermediate pivot and mounting member shown in FIG. 65;

FIG. 71 is a top view of the handle portion of the surgical stapling device shown in FIG. 8 with the articulation actuator moved to a third position to articulate the tool assembly to a third orientation; and FIG. 72 is a bottom view of the carrier portion, intermediate pivot and mounting member as shown in FIG. 70 after the articulation actuator has been moved to the position shown in FIG. 71.

FIG. 73 is a top view of the handle portion of the surgical stapling device shown in FIG. 8 with the articulation actuator moved to a fourth position to articulate the tool assembly to a fourth orientation; and FIG. 74 is a bottom view of the carrier portion, intermediate pivot and mounting member as shown in FIG. 70 after the articulation actuator has been moved to the position shown in FIG. 73.

DETAILED DESCRIPTION OF PREFERRED EMBODIMENTS

Figure 1:
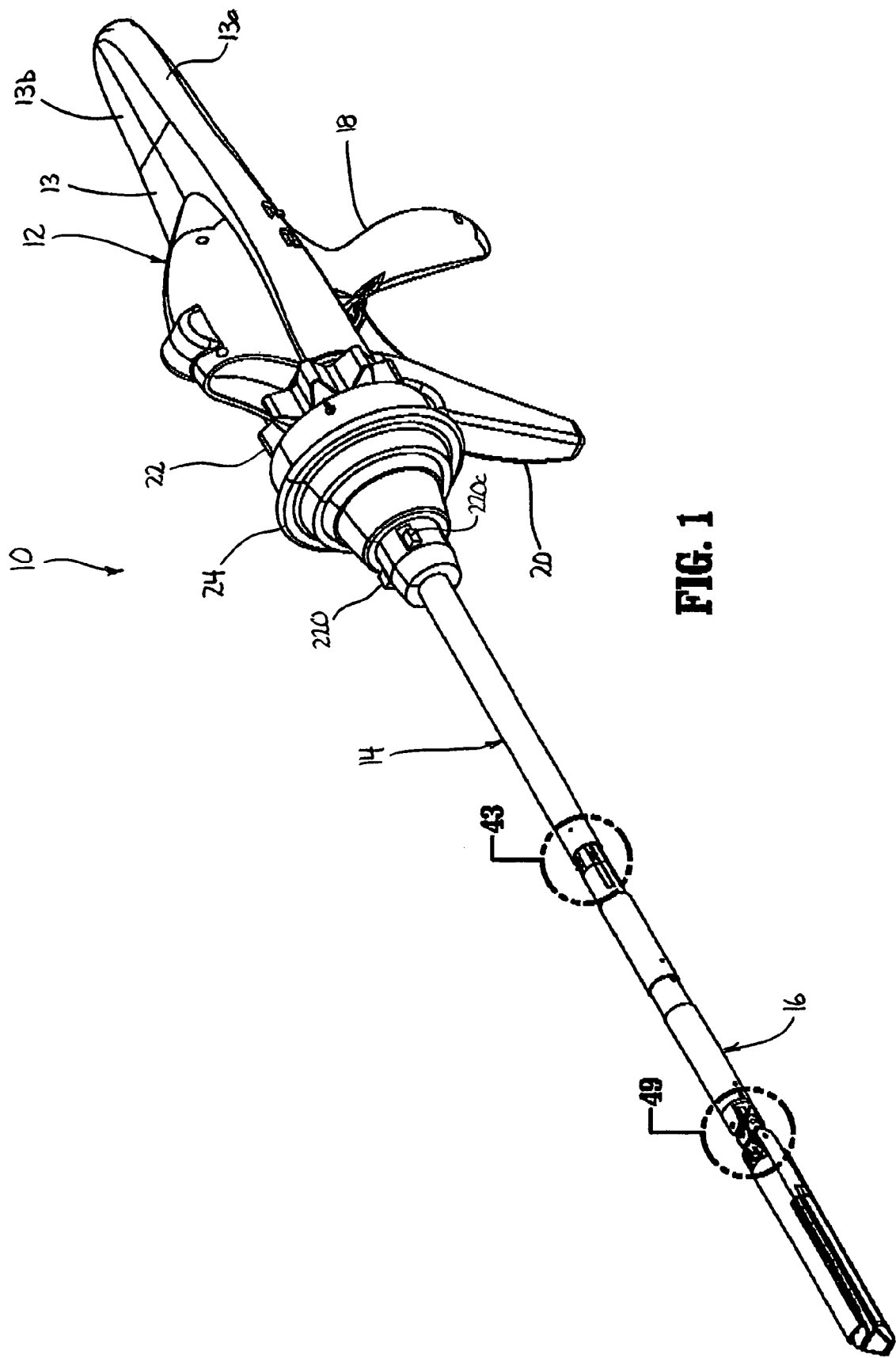
FIG. 1 is a side perspective view from the distal end of the presently disclosed surgical stapling device.
Figure 2:
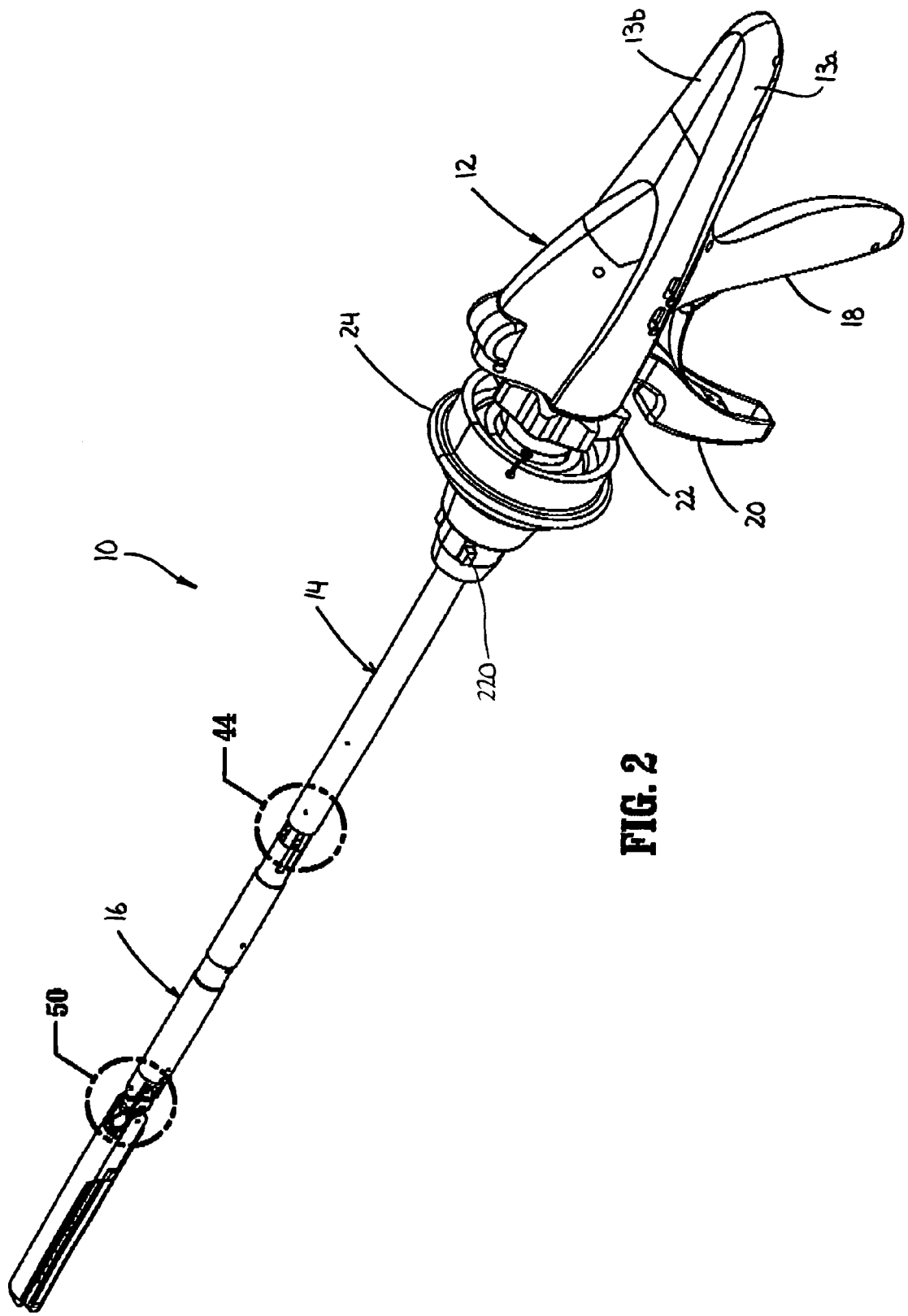
FIG. 2 is a side perspective view from the proximal end of the surgical stapling device shown in FIG. 1.
Figure 5:
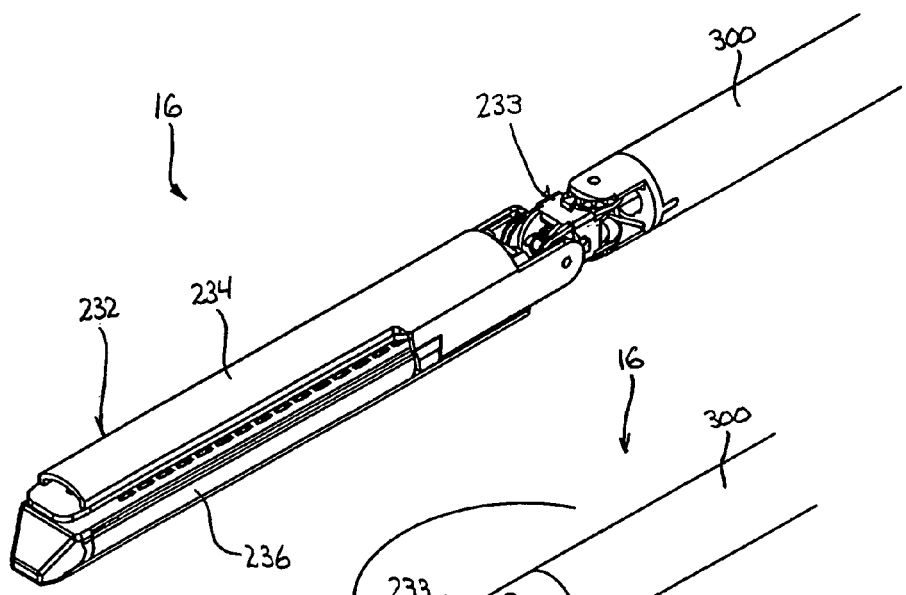
FIG. 5 is a side perspective view from the distal end of the proximal body portion and tool assembly of the SULU of the surgical stapling device shown in FIG. 4 with the tool assembly in a non-articulated position.
Figure 6:
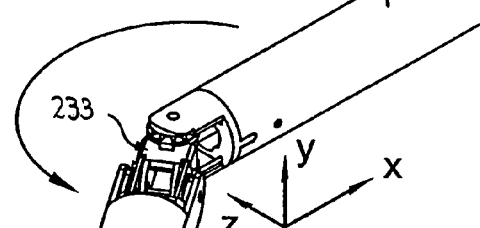
FIG. 6 is a side perspective view from the distal end of the SULU shown in FIG. 5 with the tool assembly articulated about a first axis.
Figure 7:
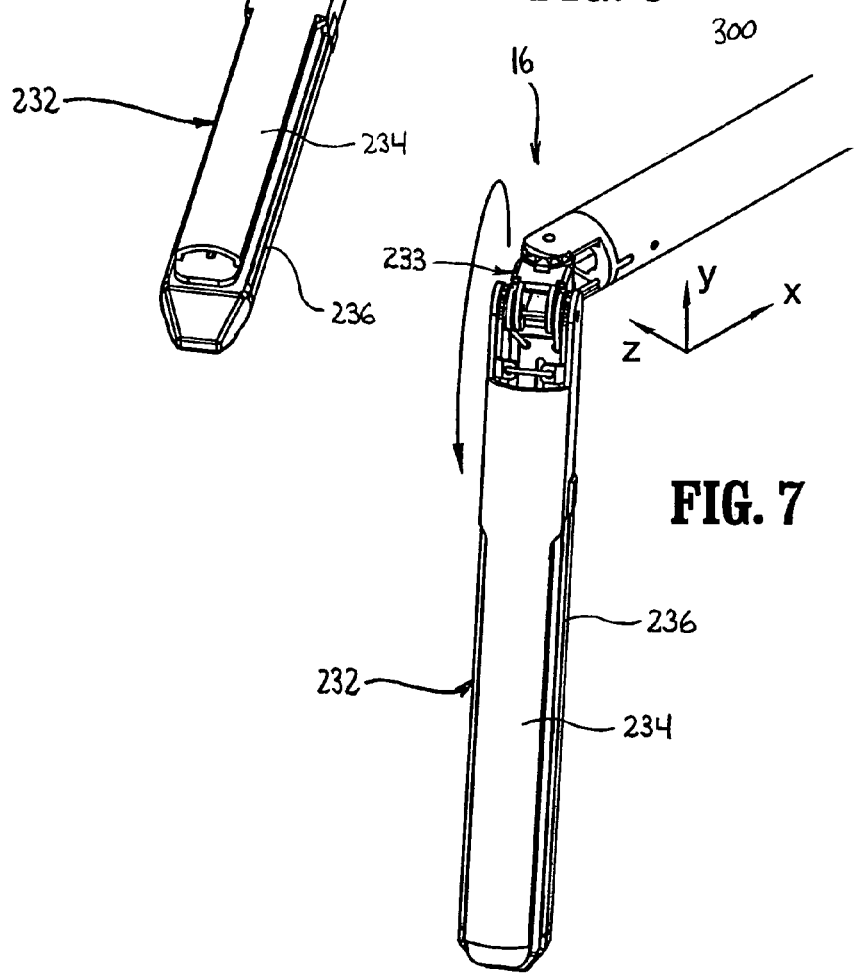
FIG. 7 is a side perspective view from the distal end of the SULU shown in FIG. 6 with the tool assembly articulated about a second axis transverse to the first axis.
Figure 8:
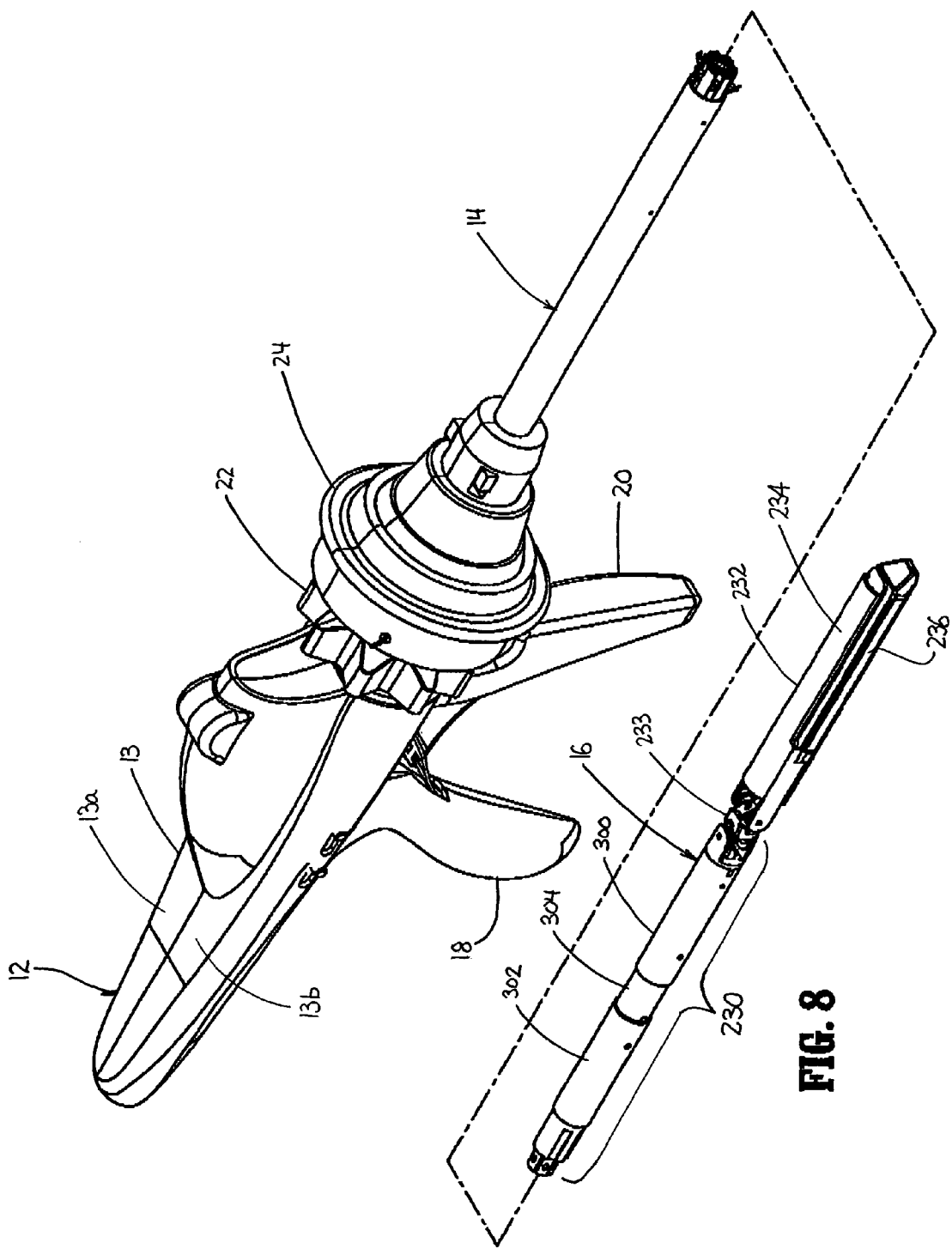
FIG. 8 is a side perspective view from the distal end of the surgical stapling device shown in FIG. 4 with the SULU separated from the central portion of the central body portion of the surgical stapling device shown in FIG. 8 with a handle portion half-section, the rotation control member and the articulation actuator removed.

Preferred embodiments of the presently disclosed stapling device will now be described in detail with reference to the drawings in which like reference numerals designate identical or corresponding element in each of the several views.

U.S. provisional application Ser. No. 60/416,088 filed Oct. 4, 2002 and U.S. provisional application Ser. No. 60/416,372 filed Oct. 4, 2002 are incorporated herein by reference in their entirety.

Throughout this description, the term "proximal" will refer to the portion of the device closest to the operator and the term "distal" will refer to the portion of the device furthest from the operator.

FIGS. 1-8 illustrate one embodiment of the presently disclosed surgical stapling device shown generally as 10. Briefly, surgical stapling device 10 includes a proximal handle portion 12, an elongated central body portion 14 and a distal disposable loading unit ("DLU") 16. Preferably, the DLU is a single use loading unit ("SULU"). Handle portion 12 includes a body 13 defining a stationary handle 18, a trigger 20, a rotation control member 22 for rotating and an articulation actuator 24. Body 13 includes a pair of molded half-sections 13a and 13b, which may be formed of a thermoplastic material, e.g., polycarbonate. Alternately, other materials having the requisite strength requirements may be used to form body 13, e.g., surgical grade metals. Body 13 half-sections 13a and 13b are secured to each other using known fastening techniques, e.g., adhesives, welding, interlocking structure, screws, etc. Alternately, other fastening techniques may be used.

Figure 14:
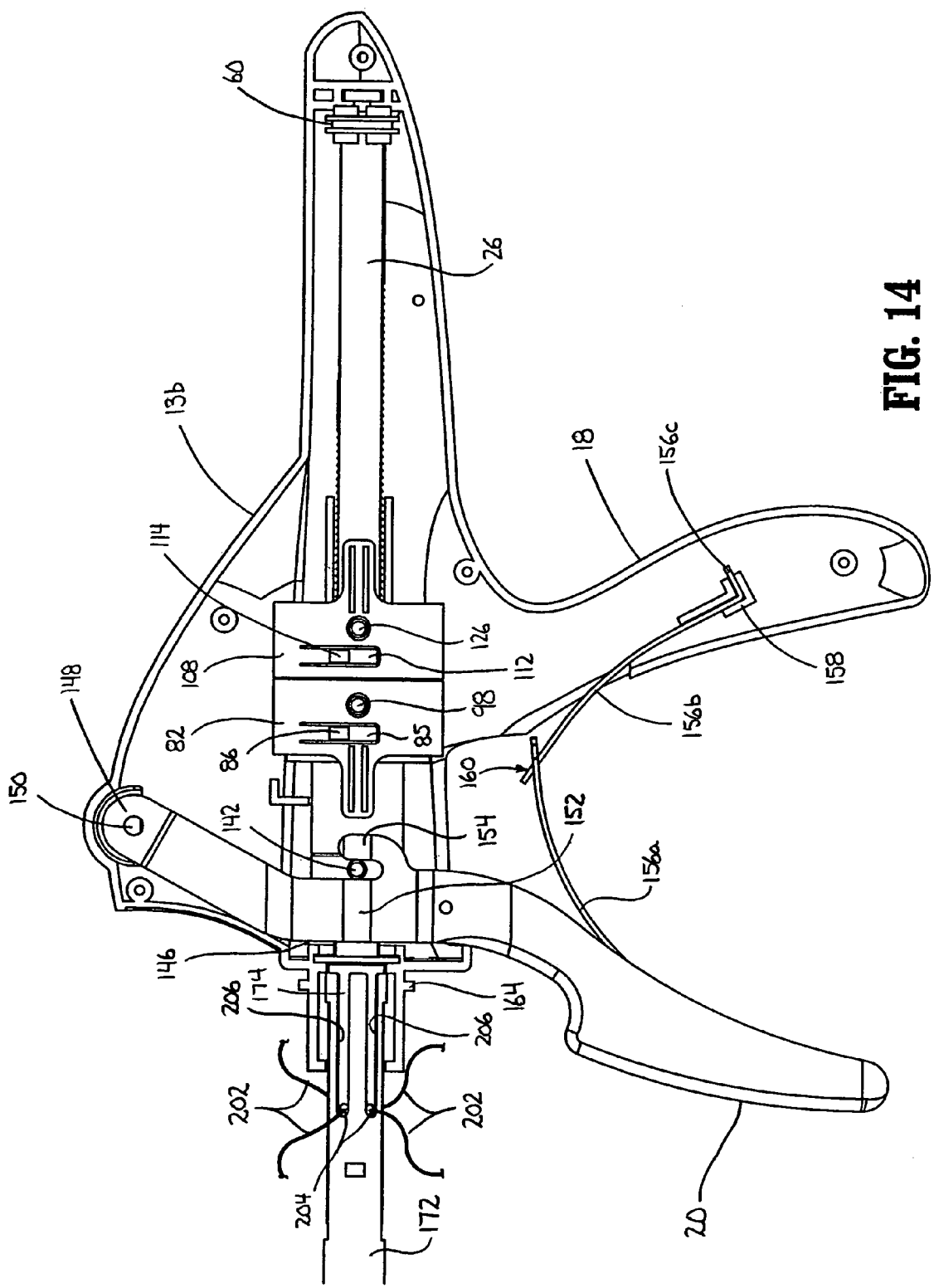
FIG. 14 is a side view of the handle portion and the proximal portion of the central body portion of the surgical stapling device shown in FIG. 8 with a handle portion half-section, the rotation control member and the articulation actuator removed.
Figure 15:
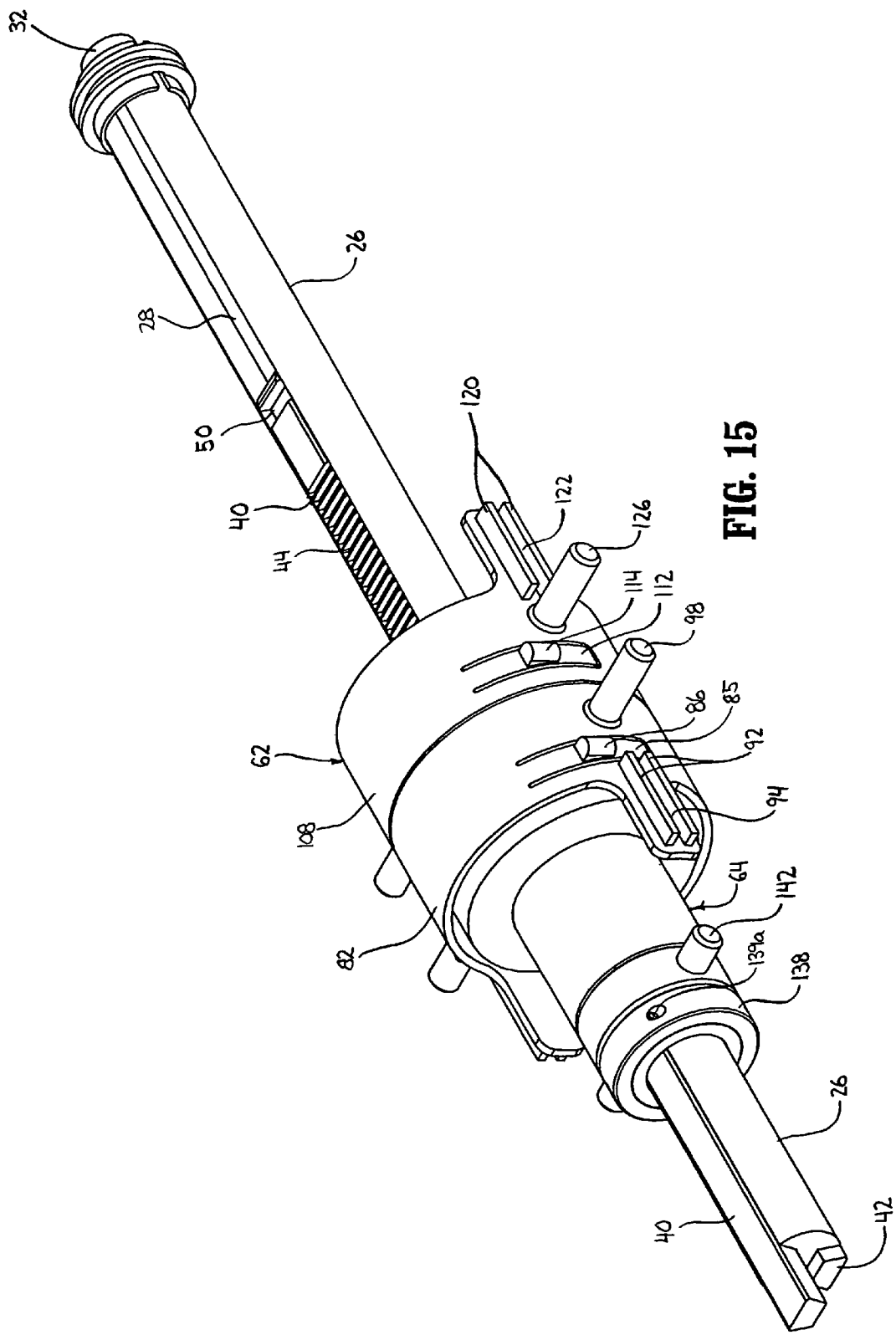
FIG. 15 is a side perspective view from the distal end of the spindle and barrel assembly of the surgical stapling device shown in FIG. 9.
Figure 16:
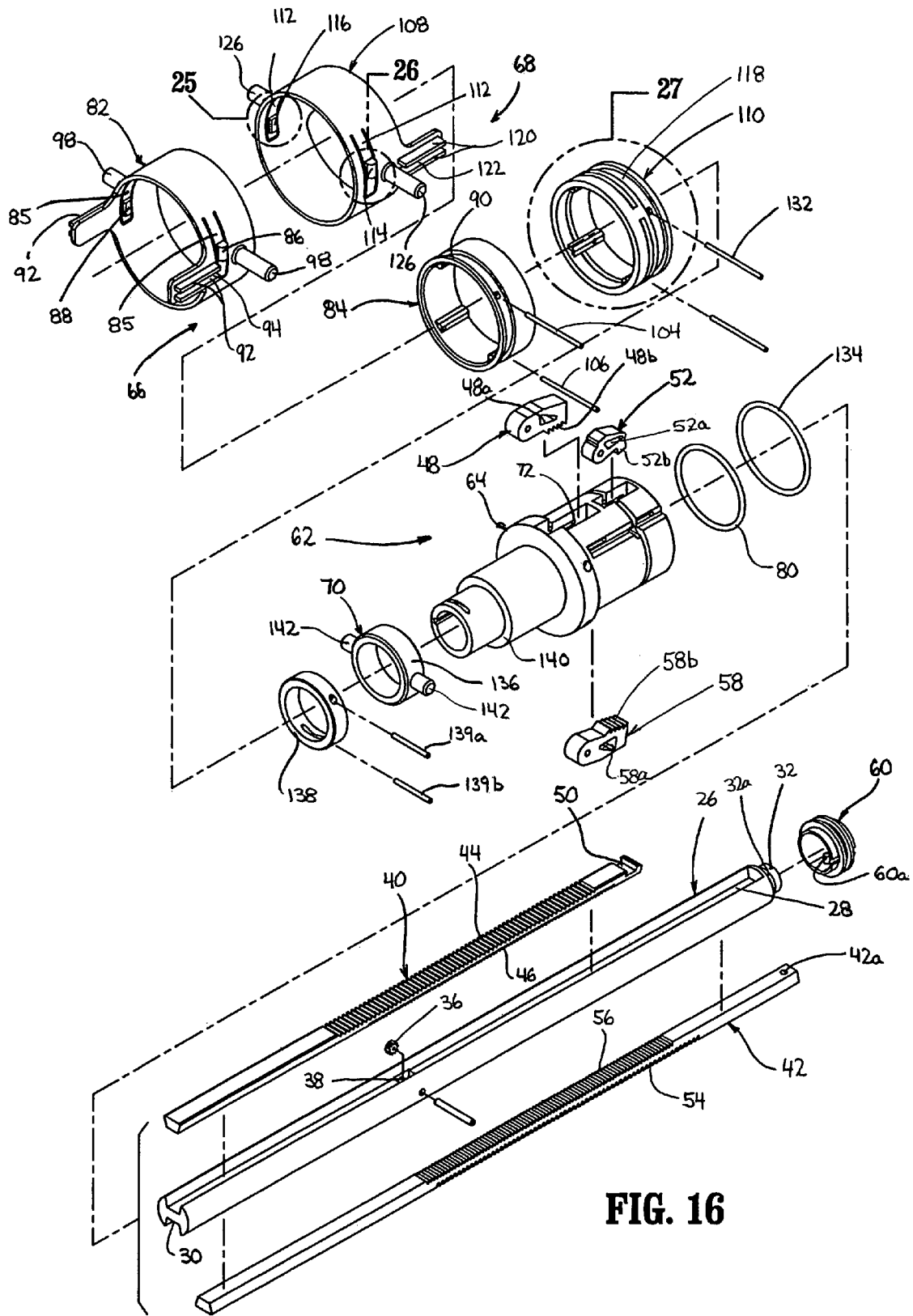
FIG. 16 is a side perspective view from the distal end of the spindle and barrel assembly shown in FIG. 15 with parts separated.

Referring to FIGS. 9-16, handle portion 12 includes an approximation/firing mechanism for approximating the jaws of SULU 16 and ejecting staples from SULU 16 as will be described in detail herein below. The approximation/firing mechanism includes a spindle 26 which defines diametrically opposed guide tracks 28 and 30 (FIG. 16). The proximal end of spindle 26 includes an extension 32 defining an annular recess 32a (FIG. 11). Extension 32 is received within a recess 34 defined in body half-sections 13a and 13b of handle portion 12 to rotatably fasten spindle 26 within body 13. A pinion 36 (FIG. 16) is rotatably secured in a throughbore 38 formed in a central portion of spindle 26. Pinion 36 includes gear teeth which extend into guide tracks 28 and 30.

Referring to FIG. 16, a firing rack 40 is slidably received in guide track 28 of spindle 26 and a retraction rack 42 is slidably received in guide track 30 of spindle 26. Firing rack 40 includes gear teeth 44 and 46 formed on opposite sides of the rack. Gear teeth 44 are positioned to engage the teeth of an advancement and firing pawl 48 ("firing pawl"). Gear teeth 46 are positioned to engage the teeth of pinion 36. The proximal end of firing rack 40 includes a cutout 50 which is dimensioned to engage a grasper pawl 52 in a manner to be discussed in detail below.

Retraction rack 42 also includes gear teeth 54 and 56 formed on opposite sides of the rack. Gear teeth 54 are positioned to engage the teeth of a retraction pawl 58 and gear teeth 56 are positioned to engage the teeth of pinion 36. The proximal end of retraction rack 42 includes a bore 42a for receiving a pin 60a of an indicator ring 60. Indicator ring 60 is positioned about spindle 26 and is secured to and movable with retraction rack 42. Preferably, indicator ring 60 is colored to facilitate viewing, e.g., red. A window or transparent portion (not shown) of body 13 of handle portion 12 permits viewing of the position of indicator ring 60. Indicia may be provided on body 13 adjacent the viewing portion to identify the stage of operation of the device in relation to the position of indicator ring 60.

Figure 33:
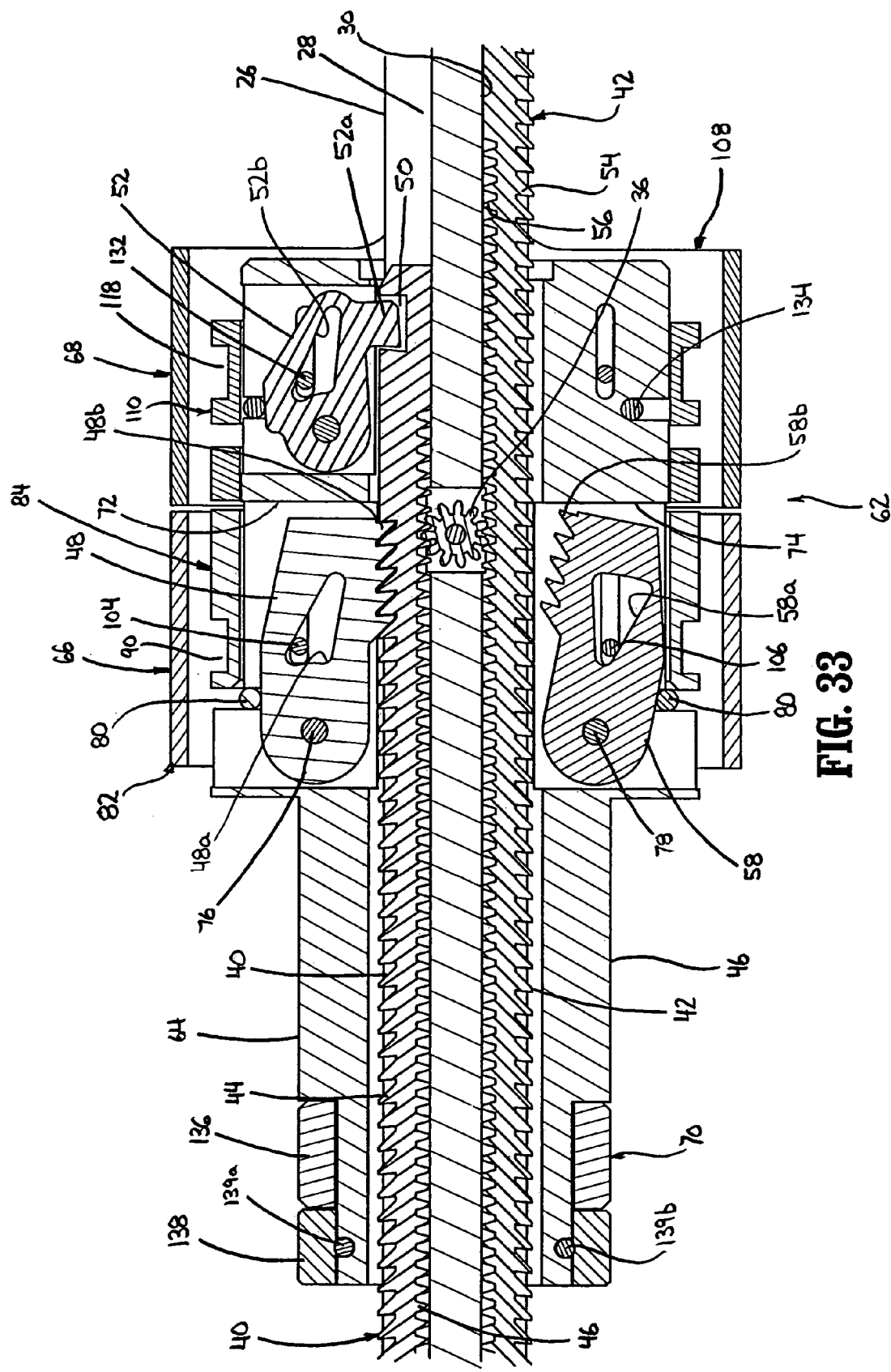
FIG. 33 is an enlarged view of the indicated area of detail shown in FIG. 32.
Figure 33A:
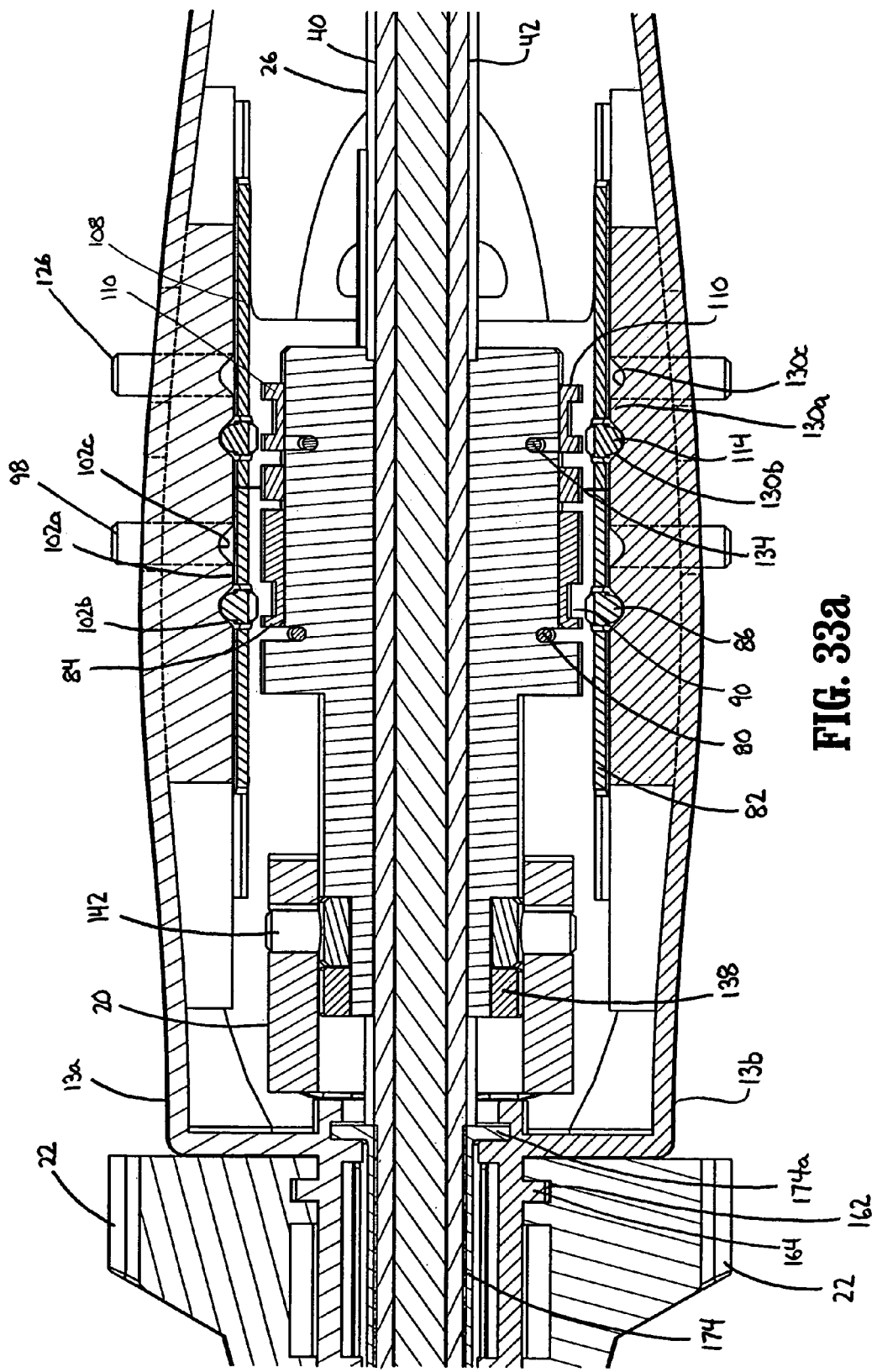
FIG. 33a is an enlarged horizontal cross-sectional view of a portion of the handle portion of surgical stapling device shown in FIG. 1 with the first and second shift ring assemblies in their distal-most positions and the firing pawl engaged with the firing rack.
Figure 33B:
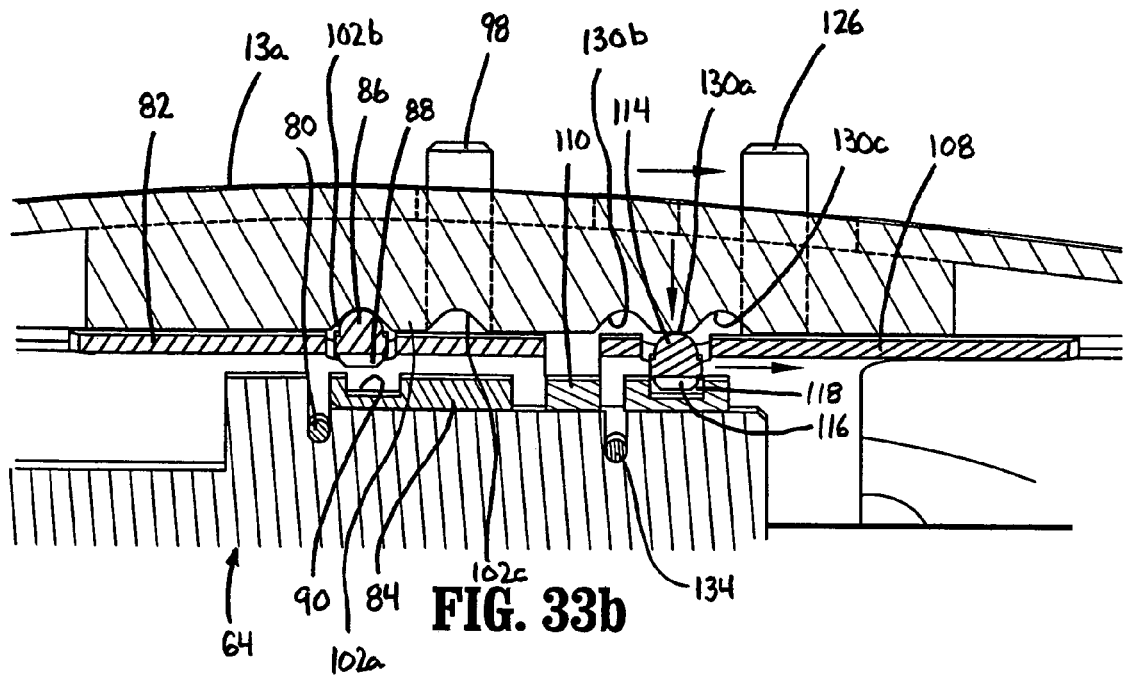
FIG. 33b is a horizontal cross-sectional view with portions broken away of one side of the handle portion of the surgical stapling device shown in FIG. 33a and with the second shift ring assembly being moved towards its proximal-most position.
Figure 33C:
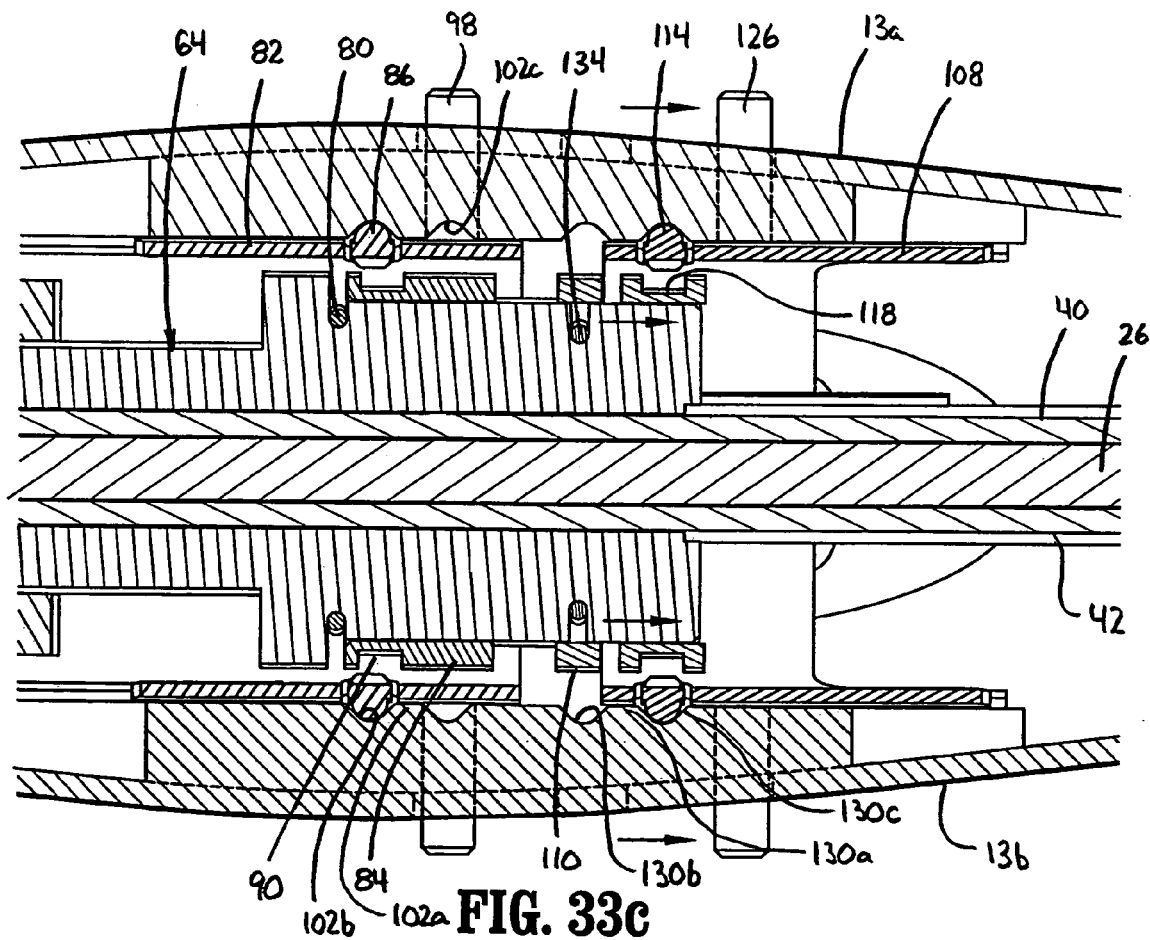
FIG. 33c is a horizontal cross-sectional view of the handle portion of the surgical stapling device shown in FIG. 33a with the second shift ring assembly moved to its proximal-most position.
Figure 33D:
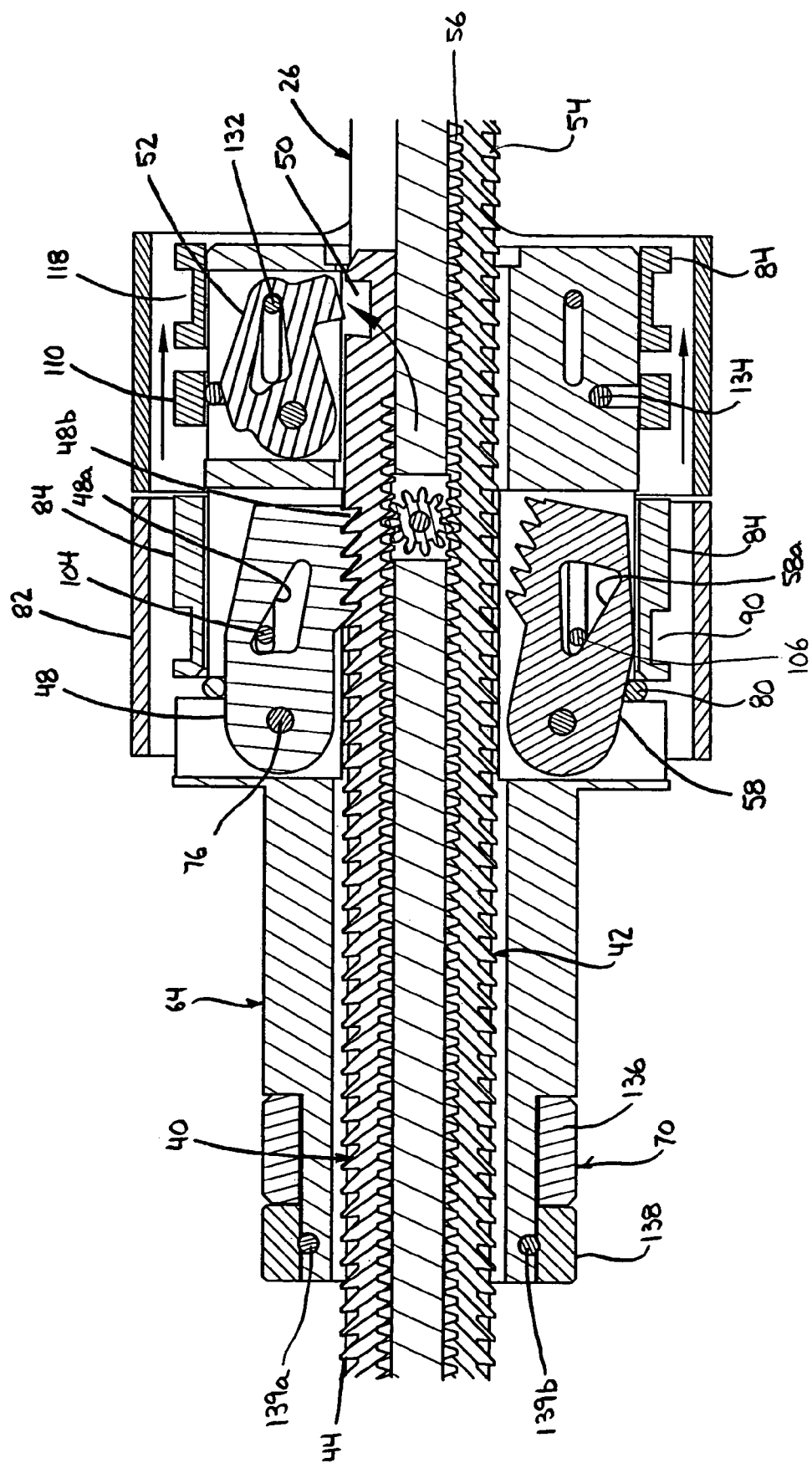
FIG. 33d is a cross-sectional view of the barrel assembly and spindle shown in FIG. 30 with the second shift ring assembly in its proximal-most position and the grasper pawl disengaged with the firing rack.

Referring also to FIGS. 15 and 33, a barrel assembly 62 is slidably positioned about spindle 26. Barrel assembly 62 includes firing pawl 48, grasper pawl 52, retraction pawl 58, a body portion 64, first and second shift ring assemblies 66 and 68, and a trigger connector 70. Barrel assembly body portion 64 includes a pair of opposed throughbores 72 and 74. Firing pawl 48 is pivotally secured within throughbore 72 about a pivot pin 76 which extends through barrel assembly body portion 64. Retraction pawl 58 is pivotally secured within throughbore 74 about a pivot pin 78 which extends through barrel assembly body portion 64. A spring member or O-ring 80 is positioned about body portion 64 and engages firing pawl 48 and retraction pawl 58 to urge firing pawl 48 and retraction pawl 58 into engagement with firing rack 40 and retraction rack 42, respectively. Alternately, other biasing devices may be used to bias the firing pawl and retraction pawl into engagement with the firing and retraction racks. Firing pawl 48 includes a cam slot 48a and series of teeth 48b configured to engage teeth 44 of firing rack 40. Retraction pawl 58 includes a cam slot 58a and a series of teeth 58b configured to engage teeth 54 of retraction rack 42.

First shift ring assembly 66 includes an outer ring 82 and an inner ring 84. Outer ring 82 is slidably positioned about barrel assembly body portion 64. Outer ring 82 includes a pair of cantilevered spring arms 85. Each spring arm includes an outer abutment member 86 and an inner protrusion 88. Inner ring 84 is slidably positioned about barrel assembly body portion 64 within outer ring 82 and includes an outer annular recess 90 dimensioned to receive protrusion 88 of spring arm 85 in a manner to be described in detail below. Frictional contact between the inner surface of inner ring 84 and the outer surface of barrel assembly body portion 64 retains the inner ring 84 at a fixed position on the barrel assembly body portion 64 until inner ring 84 is manually moved.

Outer ring 82 is slidably positioned within handle body 13 and includes a pair of elongated ribs 92 on each side thereof. Ribs 92 define an elongated slot 94 which is dimensioned to slidably receive an elongated rib 96 (FIG. 34) formed on an inner surface of body half-sections 13a and 13b (FIG. 35). The positioning of rib 96 in slot 94 restricts outer ring 82 to linear movement. A pair of diametrically opposed prongs 98 extend outwardly from each side of outer ring 82 through elongated slots 100 (FIG. 34) formed in each of body half-sections 13a and 13b. Prongs 100 are positioned on the handle body 13 at a position to be manipulated by an operator of device 10 to move outer ring 82 linearly within handle body 13 from an advanced to a retracted position.

Figure 34:
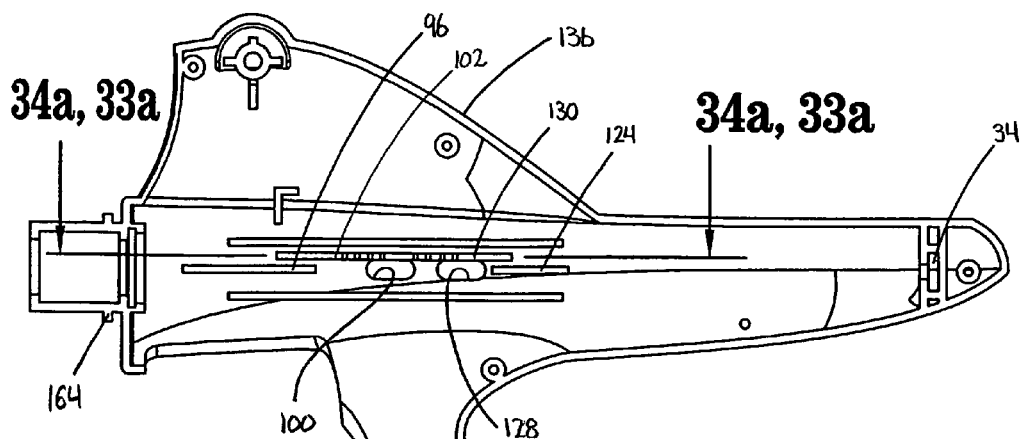
FIG. 34 is a side view of the internal body of a handle portion half-section of the handle portion shown in FIG. 33e.
Figure 34A:
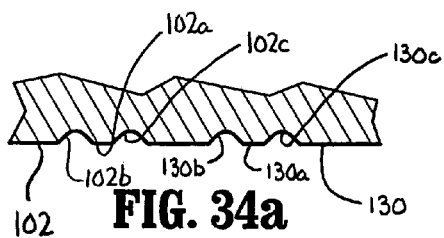
FIG. 34a is an enlarged partial cutaway cross-sectional view taken along section lines 34a-34a of FIG. 34.
Figure 35:
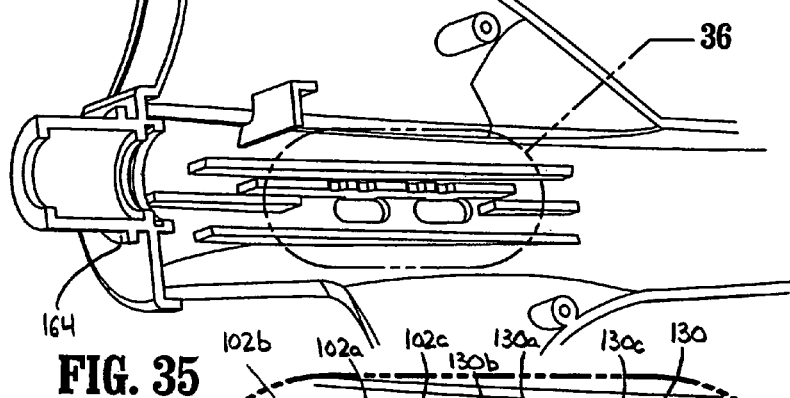
FIG. 35 is an enlarged side perspective view of a portion of the handle portion shown in FIG. 34.
Figure 36:
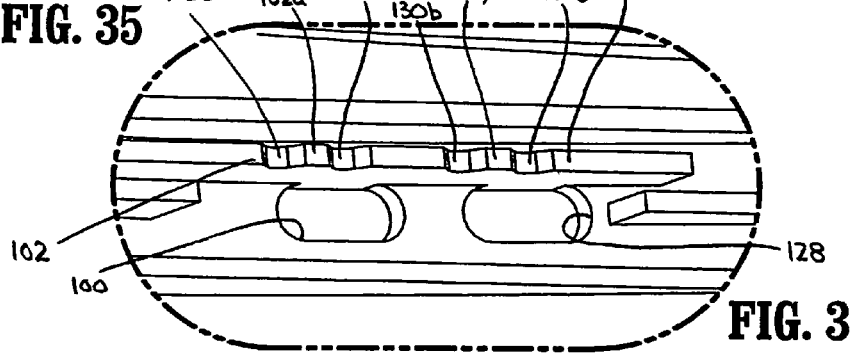
FIG. 36 is an enlarged view of the indicated area of detail shown in FIG. 35.

Referring also to FIGS. 34-36, a cam surface 102 is formed on an inner surface of each of body half-sections 13a and 13b. Abutment member 86 of spring arm 85 of outer ring 82 is positioned to slide over cam surface 102 as the outer ring 82 is moved from an advanced position about body portion 64 to a retracted position about body portion 64. Cam surface 102 includes a raised surface 102a and recesses 102b and 102c positioned at each end of cam surface 102. When outer ring 82 is moved linearly within handle body 13 between the advanced and retracted positions, abutment member 86 engages raised surface 102a of cam surface 102 to push spring arm 85 inwardly such that inner protrusion 88 moves into annular recess 90 of inner ring 84 about body portion 64. When inner protrusion 88 is received within annular recess 90 of inner ring 84, linear movement of outer ring 82 is translated into linear movement of inner ring 84. When abutment member 86 passes raised surface 102a, spring arm 85 moves outwardly such that abutment member 86 moves into the recess 102b or 102c and inner protrusion 88 moves out of annular recess 90 to disengage the inner and outer rings 82 and 84 respectively.

A pin or rod 104 (FIG. 16) extends across inner ring 84 through firing pawl cam slot 48a. A second pin or rod 106 extends across inner ring 84 through retraction pawl cam slot 58a. When inner ring 84 is moved from the advanced to the retracted position, pins 104 and 106 move within firing pawl cam slot 48a and retraction pawl cam slot 58a, respectively, to allow spring member 80 to move retraction pawl 58 into engagement with the respective retraction rack 42 and to move firing pawl 48 out of engagement with firing rack 40. (See FIG. 33g).

When inner ring 84 is moved from the retracted position to the advanced position, pins 104 and 106 move within cam slots 48a and 58a, respectively, to pivot firing pawl 48 into engagement with firing rack 40 and to allow spring member 80 to pivot retraction pawl 58 out of engagement with retraction rack 42. (See FIG. 33).

Referring again to FIGS. 15, 16 and 33, second shift ring assembly 68 (FIG. 16) also includes an outer ring 108 and an inner ring 110 and functions identically to the first shift ring assembly. More specifically, outer ring 108 is slidably positioned about barrel assembly body portion 64 and includes a pair of cantilevered spring arms 112. Each spring arm includes an outer abutment member 114 and an inner protrusion 116. Inner ring 110 is slidably positioned about barrel assembly body portion 64 within outer ring 108 and includes an annular recess 118 dimensioned to receive protrusion 116 of spring arm 112 in a manner to be described in detail below. Frictional contact between the inner surface of inner ring 110 and the outer surface of the barrel assembly body portion 64 retains the inner ring 110 at a fixed position on the barrel assembly body portion 64.

Outer ring 108 is slidably positioned within handle body 13 and includes a pair of elongated ribs 120 on each side thereof. Ribs 120 define an elongated slot 122 which is dimensioned to slidably receive an elongated rib 124 (FIG. 34) formed on an inner surface of body half-sections 13a and 13b (FIG. 35). The positioning of rib 124 in slot 122 restricts outer ring 108 to linear movement. A pair of diametrically opposed prongs 126 extend outwardly from each side of outer ring 108 through elongated slots 128 (FIG. 36) formed in each of body half-sections 13a and 13b. Prongs 128 are positioned on the handle body 13 at a position to be manipulated by an operator of device 10 to move outer ring 108 linearly within handle body 13 from an advanced to a retracted position.

Referring also to FIGS. 34-36, a cam surface 130 is formed on an inner surface of each of body half-sections 13a and 13b. Abutment member 114 of spring arm 112 of outer ring 108 is positioned to slide over cam surface 130 as the outer ring 82 is moved from its retracted position to its advanced position. Cam surface 130 includes a raised surface 130a and recesses 130b and 130c positioned at each end of cam surface 130. When outer ring 108 is moved linearly within handle body 13 between its advanced position and its retracted position, abutment member 114 engages raised surface 130a of cam surface 130 to push spring arm 112 inwardly such that inner protrusion 116 moves into annular recess 118 of inner ring 110. When inner protrusion 116 is received within annular recess 118 of inner ring 110, linear movement of outer ring 108 is translated into linear movement of inner ring 110. When abutment member 114 passes over raised surface 130a, spring arm 112 moves outwardly such that abutment member 114 moves into the recess 130b or 130c and inner protrusion 116 moves out of annular recess 118 to disengage the inner and outer rings.

A pin or rod 132 (FIG. 16) extends across inner ring 110 through grasper pawl cam slot 52a. When inner ring 110 is moved from its advanced position to its retracted position on barrel assembly body portion 64, pin 132 moves within grasper pawl cam slot 52a to pivot grasper pawl 52 away from firing rack 40. When inner ring 110 is moved from its retracted position to its advanced position, pin 132 moves within grasper pawl cam slot 52a to a position which allows a biasing member 134 to urge a projection 52b of grasper pawl 52 into firing rack cutout 50. When projection 52b of grasper pawl 52 is positioned in firing rack cutout 50, only limited advancement and retraction of the firing rack 40 will occur upon operation of trigger 20, allowing the device to function as graspers.

Referring again to FIGS. 9-16, barrel assembly 62 also includes a trigger connector 70 (FIG. 16) which includes an annular member 136 rotatably secured about a distal end of barrel assembly body portion 64 by a cap 138. In one embodiment, cap 138 is secured to the distal end of barrel assembly body portion 64 by a pair of pins 139a and 139b to retain annular member 136 on the distal end of barrel assembly body portion 64 between cap 138 and a shoulder 140 (FIG. 16) of barrel assembly body portion 64. Alternately, other fastening techniques may be used to secure cap 138 to barrel assembly body portion 64, e.g., screw threads, adhesives, welding, etc. Annular member 136 includes a pair of prongs 142 positioned to engage the trigger 20 in a manner to be described below.

Trigger 20 includes a grip portion 144, an engagement portion 146, and a pivot portion 148. Pivot portion 148 is formed at a top end of trigger 20 and is configured to be pivotally secured between body half-sections 13a and 13b about a pivot member 150 (FIG. 14). Engagement portion 146 of trigger 20 includes a cylindrical member 152 for receiving barrel body portion and a pair of U-shaped hook members 154. Hook members 154 are dimensioned to slidably receive prongs 142 of annular member 136 such that pivotal movement of trigger 20 effects linear movement of barrel assembly 62 about spindle 26. A biasing member 156 is positioned between trigger 20 and stationary handle 18 to urge trigger 20 to a non-compressed configuration. In one embodiment, biasing member 156 includes a first part 156a secured to trigger 20, such as by pins, and a second part 156b secured to stationary handle 18 between body half-sections 13a and 13b via a hook 156c positioned within a groove 158 formed in stationary handle 18. First and second parts 156a and 156b of two part biasing member 156 may be formed of spring steel and are slidably attached using a T-slot connector 160. Alternately, other known biasing devices or fastening techniques may be used.

Figure 33E:
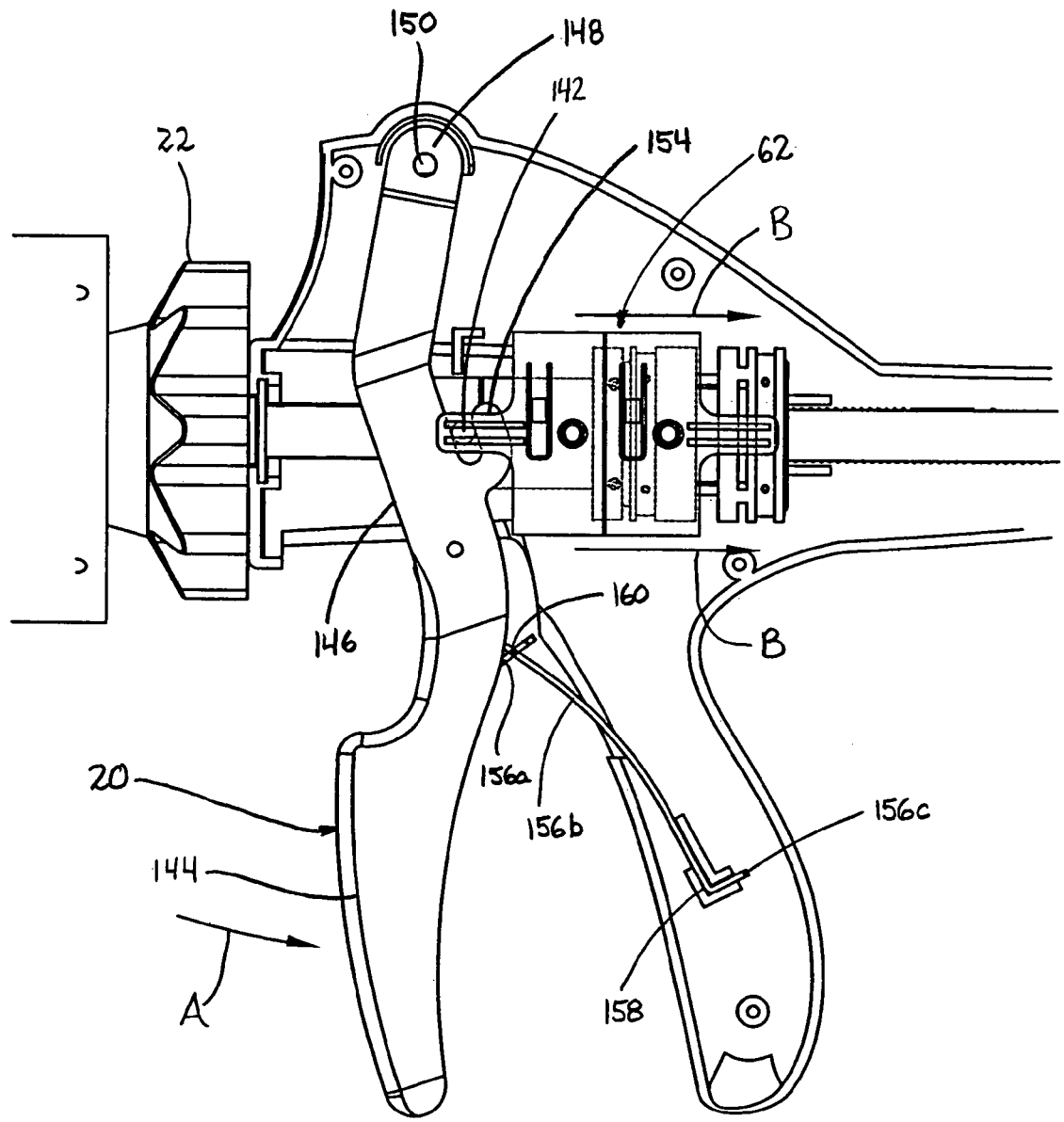
FIG. 33e is a side view of a portion of the handle portion of the surgical stapling device shown in FIG. 14 with the second shift ring assembly moved to its proximal-most position.
Figure 33F:
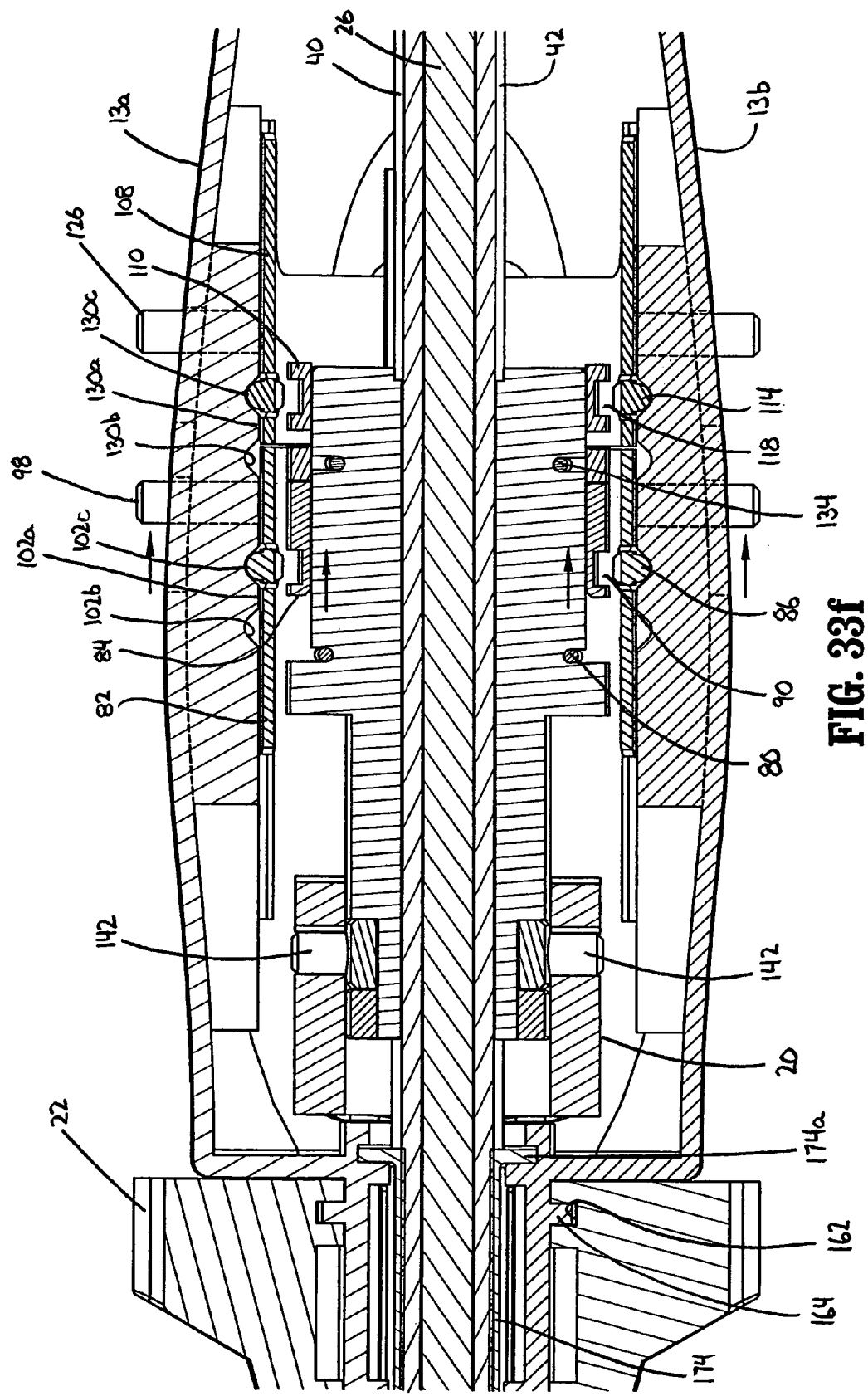
FIG. 33f is a horizontal cross-sectional view of the handle portion of the surgical stapling device shown in FIG. 1 with the first and second shift ring assemblies moved to their proximal-most positions.
Figure 33G:
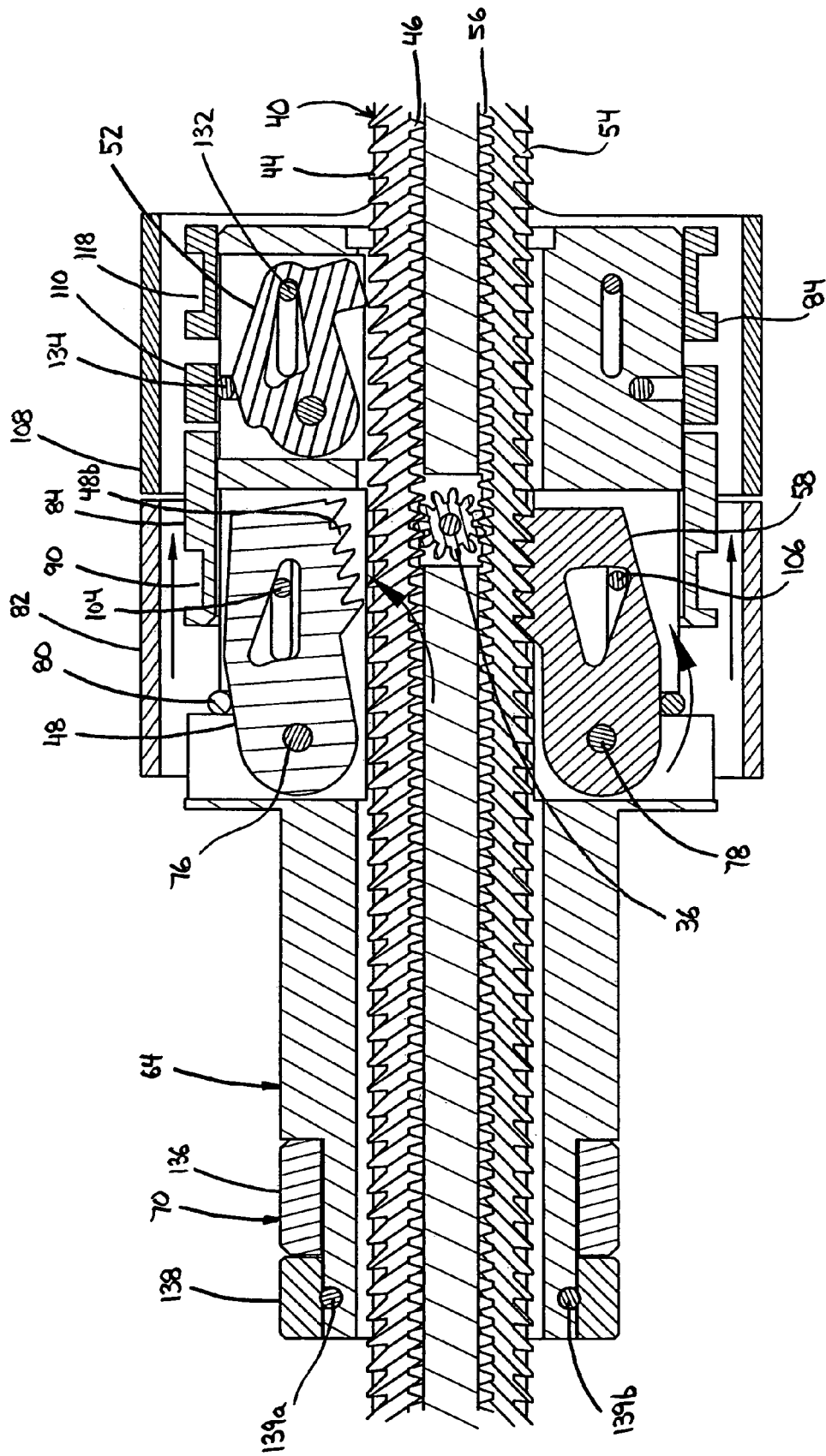
FIG. 33g is a vertical cross-sectional view of the barrel assembly and spindle shown in FIG. 30 with the first and second shift ring assemblies in their proximal-most positions.

In use, when trigger 20 is manually pivoted towards stationary handle 18 in the direction indicated by arrow "A" in FIG. 33e, barrel assembly 62 is moved proximally over spindle 26 in the direction indicated by arrow "B". If first shift ring assembly 66 is in its advanced position (FIG. 33), i.e., positioned such that firing pawl 48 is engaged with firing rack 40, firing rack 40 is pushed proximally along guide track 28. As this occurs, pinion 36, which is engaged with firing rack 40 and retraction rack 42 will rotate and advance retraction rack along guide track 30. If first shift ring assembly 66 is in its retracted position (FIG. 33g), i.e., positioned such that retraction pawl 58 is engaged with retraction rack 42, retraction rack 42 will be pushed proximally along guide track 30 as barrel assembly 62 is moved by trigger 20 proximally over spindle 26. As this occurs, pinion 36 is driven by movement of retraction rack 42 to advance firing rack 40 distally. Operation of the grasper pawl 52 will be discussed in further detail hereinbelow.

Figure 9:
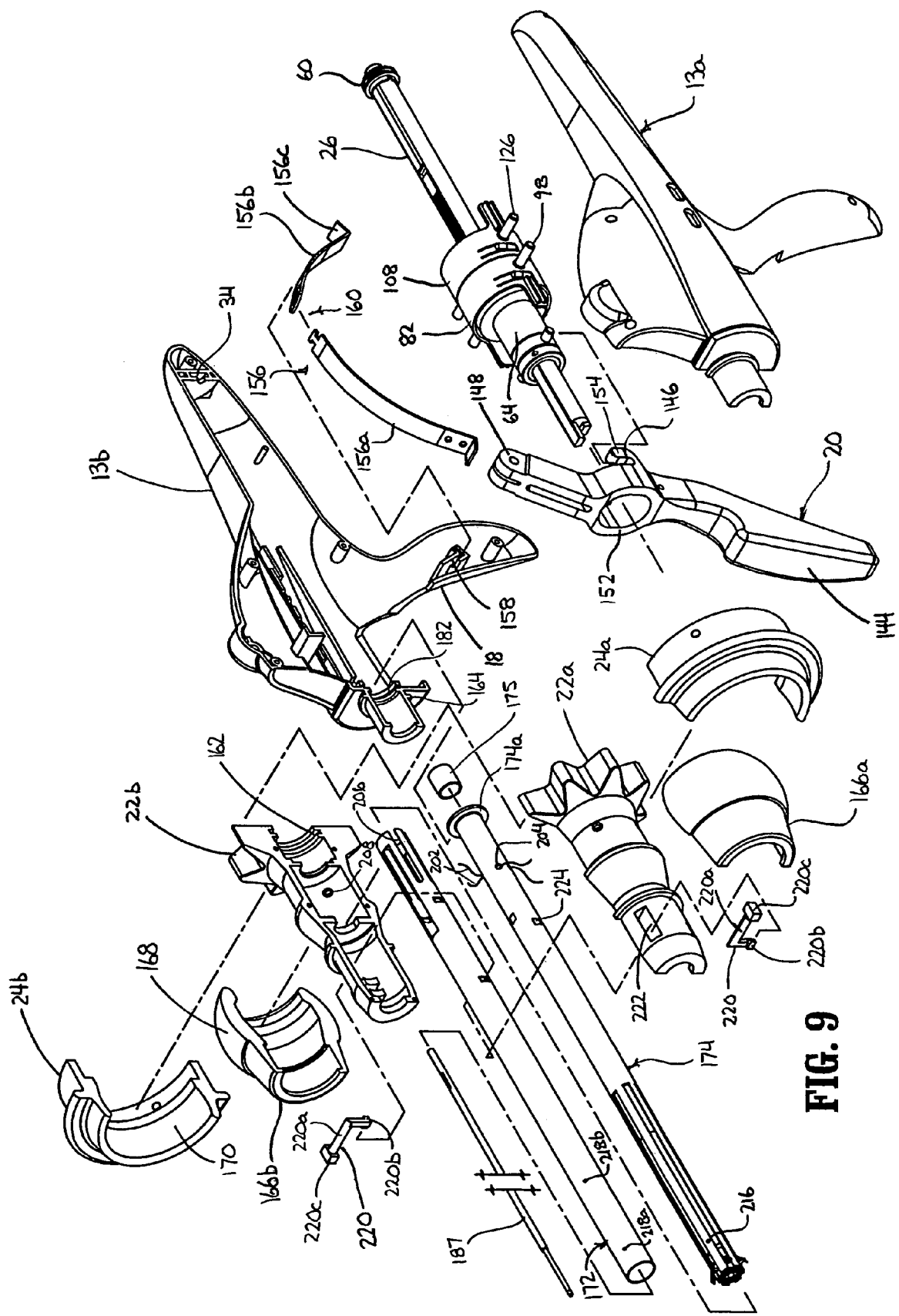
FIG. 9 is a side perspective view from the distal end of the surgical stapling device shown in FIG. 8, with parts separated and with the SULU not shown.
Figures 12, 13:
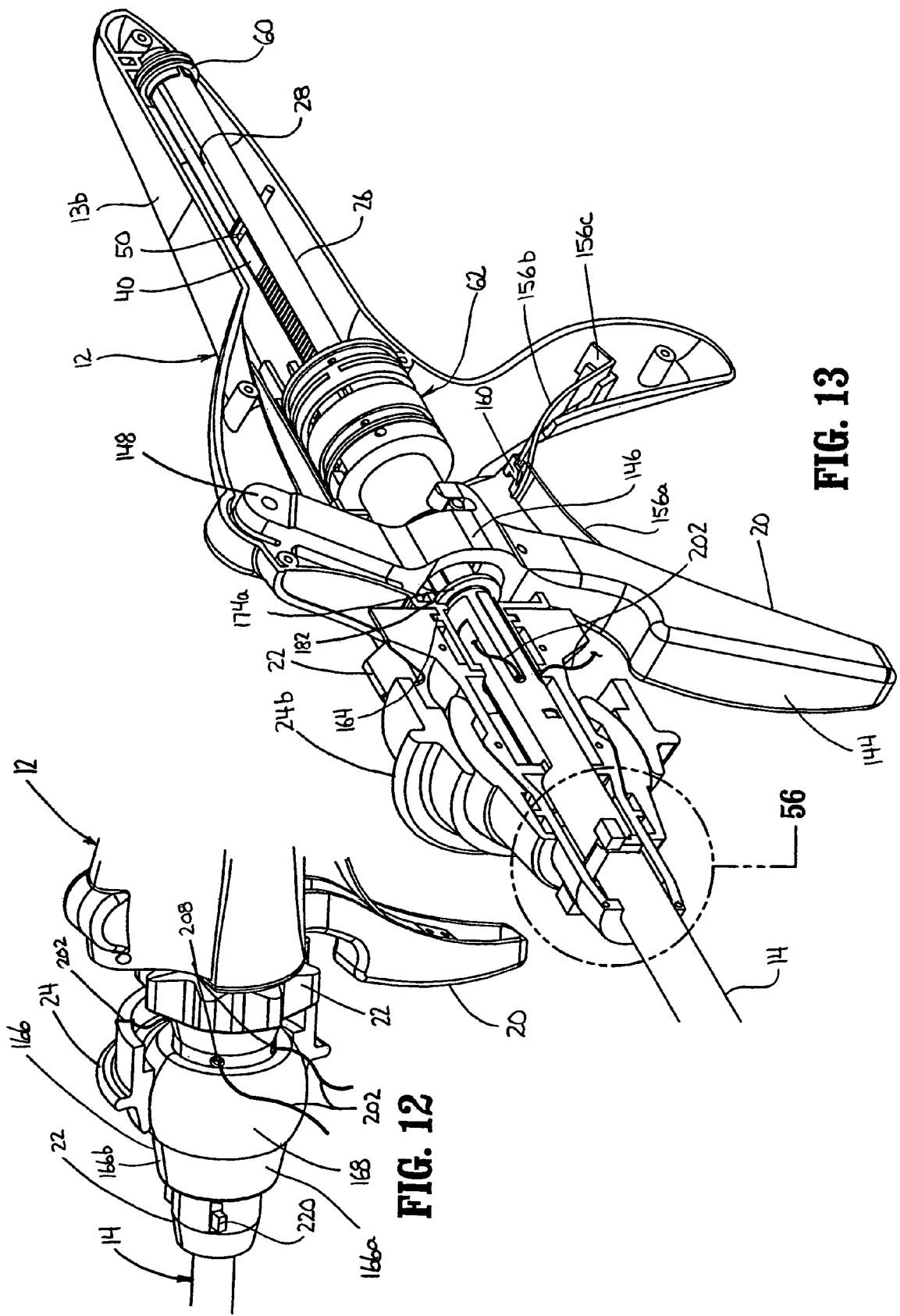
FIG. 12 is a side perspective view from the top of the distal portion of the handle portion, rotation control member, articulation actuator and proximal portion of the central body portion of the surgical stapling device shown in FIG. 8.
FIG. 13 is a side perspective view from the distal end of the handle portion and the proximal portion of the central body portion of the surgical stapling device shown in FIG. 8 with a handle portion half-section and a half-section of the rotation control member and articulation actuator removed.

Referring to FIGS. 9, 12 and 13, rotation control member 22 includes half-sections 22a and 22b which may be formed from a thermoplastic material, e.g., polycarbonate. The proximal end of control member 22 defines an inner annular channel 162 dimensioned to receive an annular rib 164 formed on the distal end of handle portion 12. Engagement between channel 162 and rib 164 rotatably fastens rotation control member 22 to handle portion 12. An actuator base member 166 has a semi-spherical outer surface 168 portion which is secured about rotation control member 22. Actuator base member 166 is can be formed from molded half-sections 166a and 166b which are fastened together about a central portion of rotation control member 22 using any known fastening technique, e.g., adhesives, welds, screws, etc. Articulation actuator 24 which may also be formed from molded half-sections 24a and 24b includes a semi-spherical inner surface 170 which is supported about semi-spherical outer surface 168 of actuator base member 166 to permit generally omni-directional movement of articulation actuator 24 in relation to base member 166, i.e., articulation actuator 24 can be pivoted in all directions about semi-spherical outer surface of base member 166. Articulation actuator 24 is movable in relation to actuator base member 166 to effect articulation of the tool member of SULU 16 as will be discussed in detail below.

Referring to FIGS. 9, 17 and 18, elongated body portion 14 includes an outer tube 172, an inner shaft 174, a plurality of articulation links 176a-d, a retraction link 178 and an advancement and firing link ("firing link") 180. The proximal end 174a of inner shaft 174 is flared outwardly and received within an annular channel 182 formed in handle body 13 to rotatably secure inner shaft 174 to handle body 13. Inner shaft 174 includes a central hub member 184 having a series of circumferentially spaced radially directed spokes 186. An alignment rod 187 is secured within hub member 184 to assist in aligning elongated body portion 14 with a SULU 16. A semi-circular guide surface 188 is secured to or formed monolithically with a distal end of each spoke 186 such that adjacent spokes 186 and respective guide surfaces 188 define a guide channel 190 for receiving each respective one of articulation links 176a-d, retraction link 178 and firing link 180.

Referring to FIGS. 17 and 18, the distal end of each of articulation links 176a-d, retraction link 178 and firing link 180 includes engagement structure including a pair of spaced fingers 192a and 192b which define a curved slot 192. Slot 192 is configured and dimensioned to receive the proximal end of respective articulation, retraction and firing links of SULU 16 in a manner to be discussed in further detail below. A hole or bore 194 is formed through each of fingers 192a and 192b. A leaf spring 196 is secured to the distal end of each of links 176a-d, 178 and 180 and includes a connector or linkage pin 198 secured thereto. Leaf spring 196, in its undeformed configuration, extends outwardly from a top surface of each link. Linkage pin 198 is supported on leaf spring 196 such that when leaf spring 196 is deformed downwardly towards the top surface of each link, linkage pin 198 is inserted through bore 194 in each of fingers 192a and 192b. Bore 194 is slightly elongated or oversized to accommodate the pivoted motion of entry of linkage pin 198.

Figure 40:
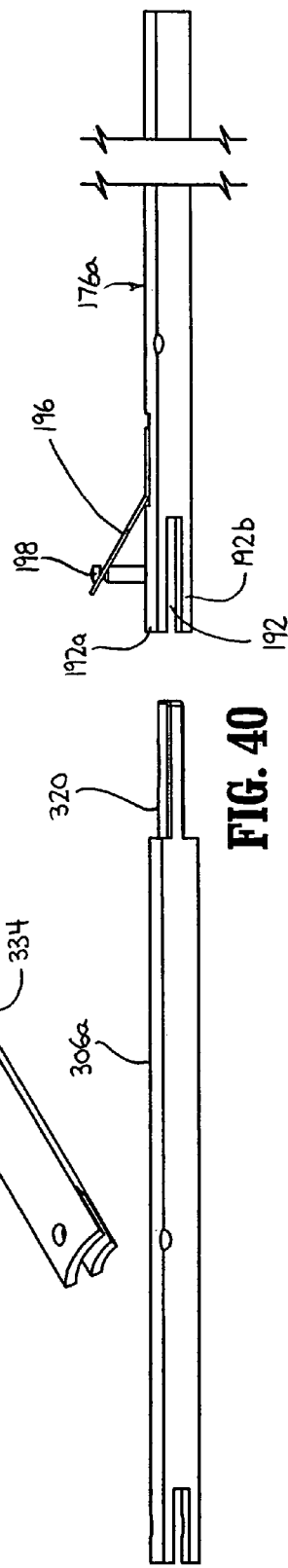
FIG. 40 is a side view of the articulation links shown in FIG. 39.
Figure 40A:
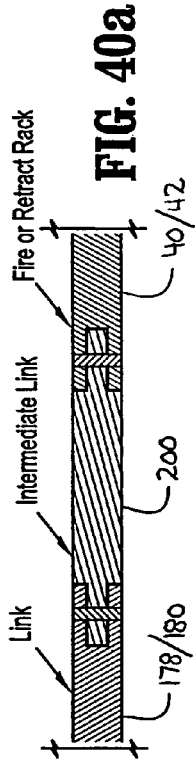
FIG. 40a is a cross-sectional view of a firing/retract link of the central body portion and a firing/retract link of the SULU interconnected by an intermediate link.
Figure 43:
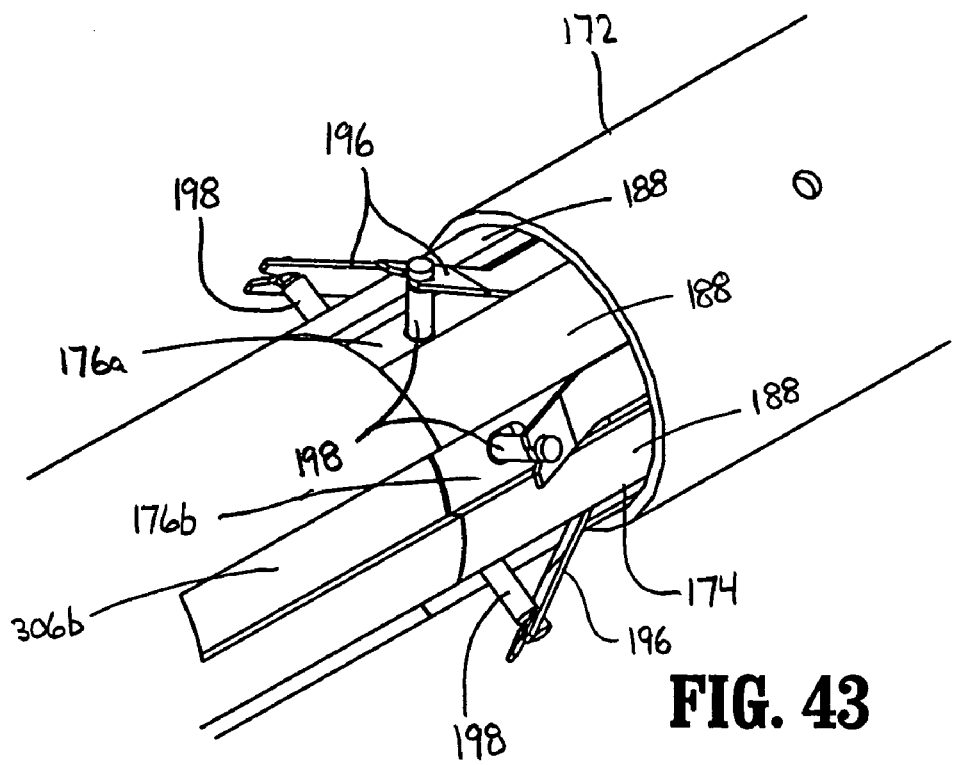
FIG. 43 is an enlarged view of the indicated area of detail shown in FIG. 1, prior to attachment of the SULU to the device.
Figure 44:
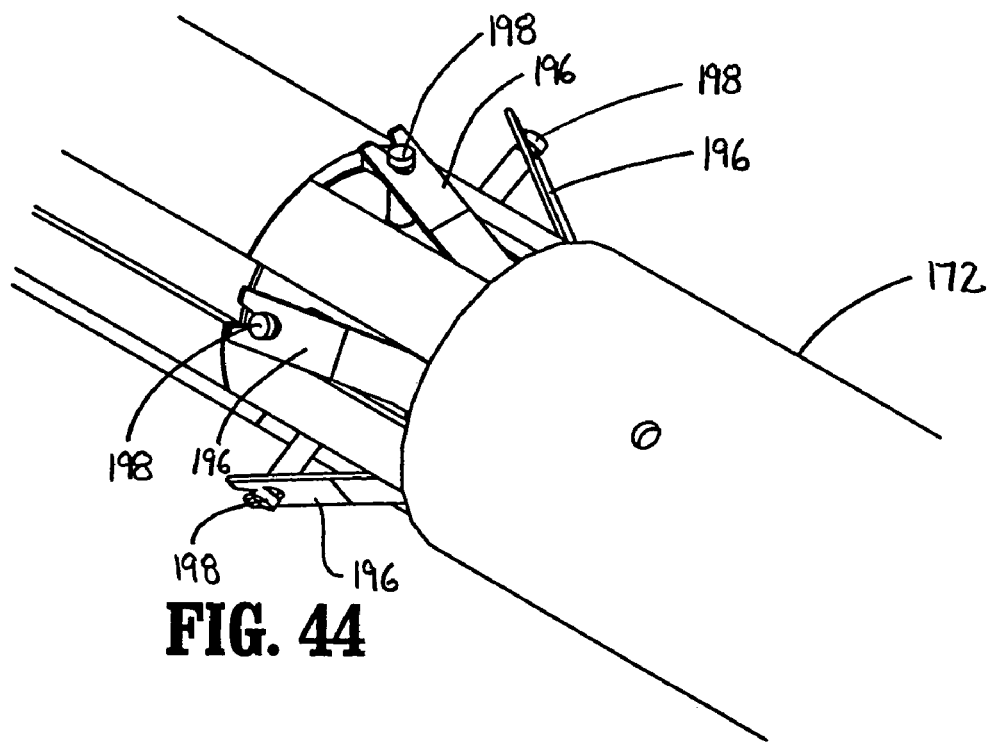
FIG. 44 is an enlarged view of the indicated area of detail shown in FIG. 2.

Referring to FIG. 40a, the proximal end of retraction link 178 is fixedly secured to the distal end of retraction rack 42 and the proximal end of firing link 180 is fixedly secured to the distal end of firing rack 40. An intermediate link 200 may be used to connect the retraction and firing links to the retraction and firing racks. It is envisioned, however, that the retraction and firing links can be directly connected to the retraction and firing racks, respectively. When an intermediate link 200 is used, this link can be a rigid link which is pinned to a rack and link such as shown in FIG. 40a or a non-rigid link or cable which can be fastened between the links and racks using any known fastening techniques, e.g., adhesives, knots, clamps, etc.

The term "rigid" in reference, e.g., to an articulation link, herein generally means that the overall link is sufficiently rigid or strong to be operable for the purposes intended (here to effectively articulate the tool assembly by use of the articulation actuator). Accordingly, for example, the end portions of the link should be rigid enough to effectively operably attach the end of the articulation link at the proximal end of the disposable loading unit to an adjacent distal end of another articulation link at the distal end of the central body portion of the surgical device. Likewise, and also to effectively and operably attach the opposite end of the articulation link to a cable. In this context here, attach means by any suitable structure or manner, e.g., so that the forces imparted at the area of attachment do not sever the cable or tear the material of the link.

As shown in FIG. 17, the proximal end of each of articulation links 176a-d is connected to articulation actuator 24 by a non-rigid link 202, e.g., cable, rope, cord, wire, Kevlar strand, or any combination thereof, etc. Alternately, rigid links may also be used to connect the proximal end of articulation links 176a-d to articulation actuator 24.

Referring to FIGS. 9-14 and 17, links 202 are secured to the proximal end of articulation links 176a-d and extend proximally through inner shaft 174. In this embodiment, links 202 are connected to articulation links 176a-d by passing link 202 through a hole near the proximal end of the links. Alternately, other attachment techniques may be used. A plastic sleeve 175 (FIG. 9) may be secured within inner shaft 174 to prevent fraying of links 202. A plurality of radially or circumferentially spaced apart openings 204 are formed through the proximal portion of inner shaft 174. Links 202 extend from within inner shaft 174, through openings 204 in inner shaft 174, through elongated slots 206 formed in outer tube 172 and through holes 208 formed in rotation control member 22 to a position adjacent articulation actuator 24. The proximal end of each of links 202 is secured to articulation actuator 24 at locations evenly spaced about the circumference of articulation actuator 24 (FIG. 10). Links 202 may be secured to articulation actuator 24 using any known fastening techniques including tying, adhesives, pins, etc. Thus, when articulation actuator 24 is manipulated by an operator, e.g., pivoted or swiveled, this motion is translated via links 202 into linear movement of articulation links 176a-d within guide channels 190 of inner shaft 174.

Referring again to FIGS. 17 and 18, each of articulation links 176a-d, retraction link 178 and firing link 180 includes at least one concavity 212 formed on a top surface thereof. Concavities 212 are configured and dimensioned to receive a locking member 214. A single locking member 214 may be positioned to be received in concavities 212 formed in a pair of adjacent links. Although locking member 214 is illustrated as a ball shaped member, it is envisioned that locking member 214 may assume other configurations which are capable of performing the function discussed below. Each locking member is seated within cooperative concavities 212 of adjacent links 176-180, such that when locking member 214 is positioned within adjacent concavities 212, the adjacent links are prevented from moving axially in relation to each other and in relation to inner shaft 174.

Referring also to FIG. 9, outer tube 172 is slidably positioned about inner shaft 174. A hole 216 is formed in each guide surface 188 of inner shaft 174 adjacent each concavity 212. Hole 216 is aligned with concavities 212 in links 176a-180, such that locking member 214 extends partially through hole 216. Outer tube 172 also includes annularly arranged ball release holes 218a and a proximal series of annularly arranged ball release holes 218b. The proximal series of ball release holes 218b are slidable into alignment with locking members 214. Distal series of ball release holes 218a are movable into alignment with locking members positioned in SULU 16 as will be discussed in detail below. When outer tube 172 is in its retracted position about inner shaft 174, the inner wall of outer tube 172 engages locking members 214 and presses locking members 214 through holes 216 in inner shaft 174 into concavities 212 of links 176-180 to lock links 176-180 axially in relation to inner shaft 174 and each other. When the outer tube is moved to its advanced position about inner shaft, ball release holes 218b align with locking members 214 to permit locking members 214 to move from concavities 212. Thus, when the device is actuated to fire or articulate, movement of a link or links 176-180 urges locking members 214 out of concavities 212 partially into ball release holes 218b to permit movement of links 176-180 in relation to inner shaft 174.

Figure 45:
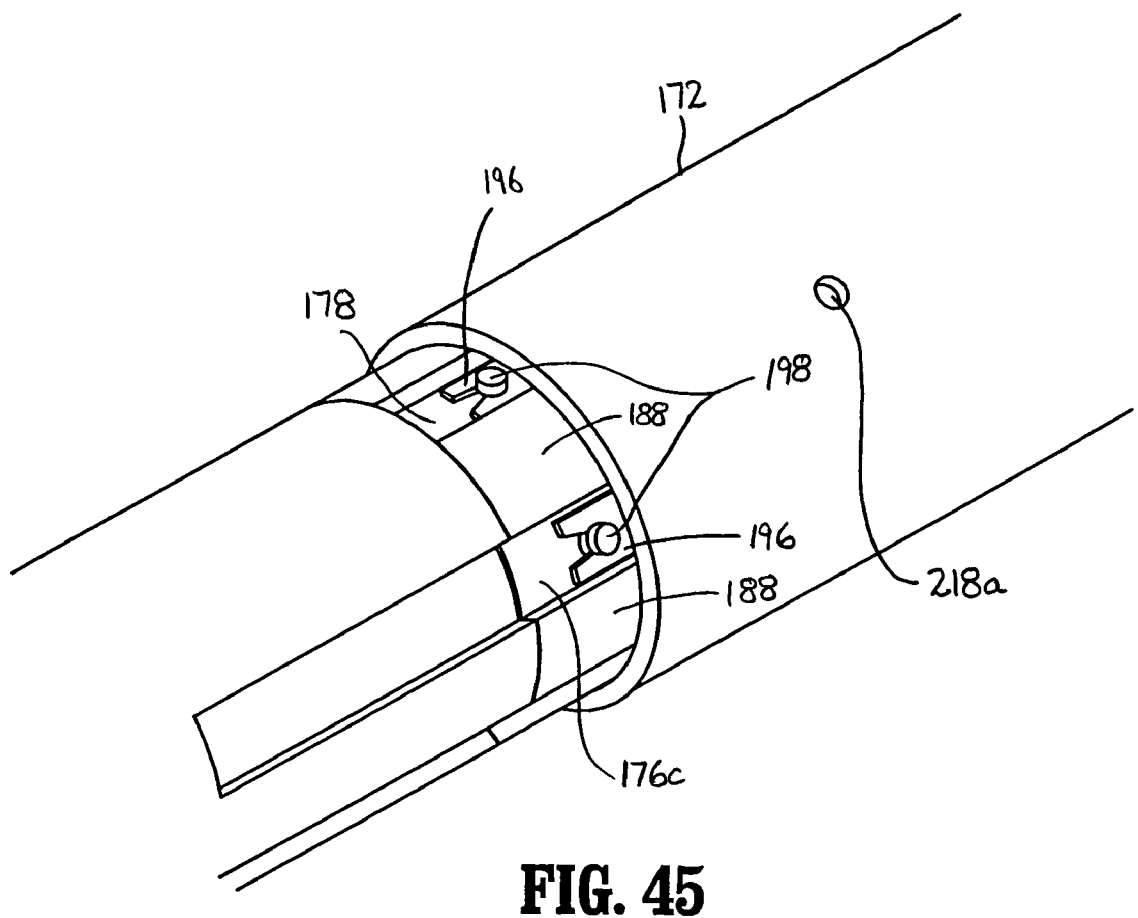
FIG. 45 is a side perspective view from the distal end of the proximal portion of the SULU and the distal portion of the central body portion of the surgical stapling device shown in FIG. 8 during attachment of the SULU to the central body portion.
Figure 46:
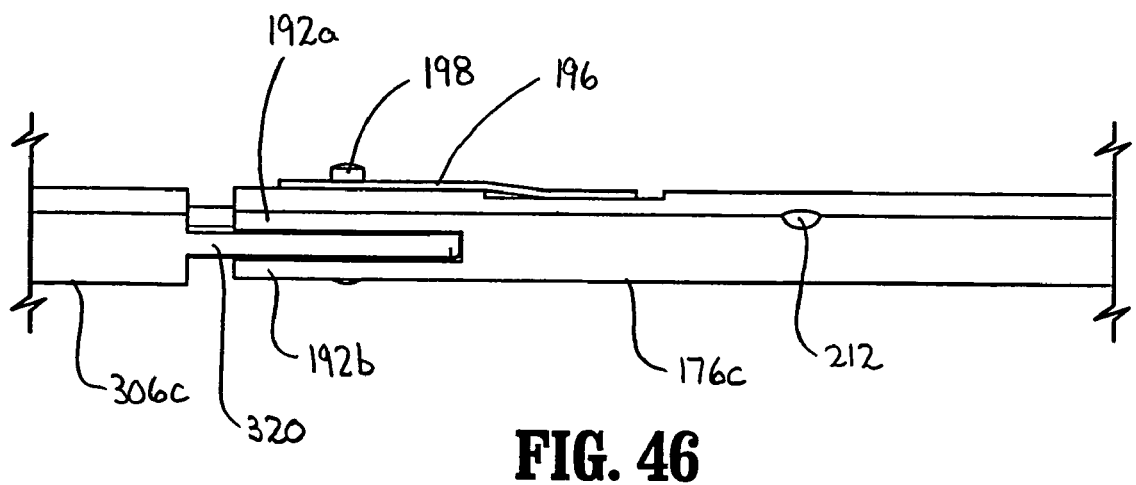
FIG. 46 is a side view of a SULU articulation link and a central body portion articulation link during attachment of one to the other.
Figure 47:
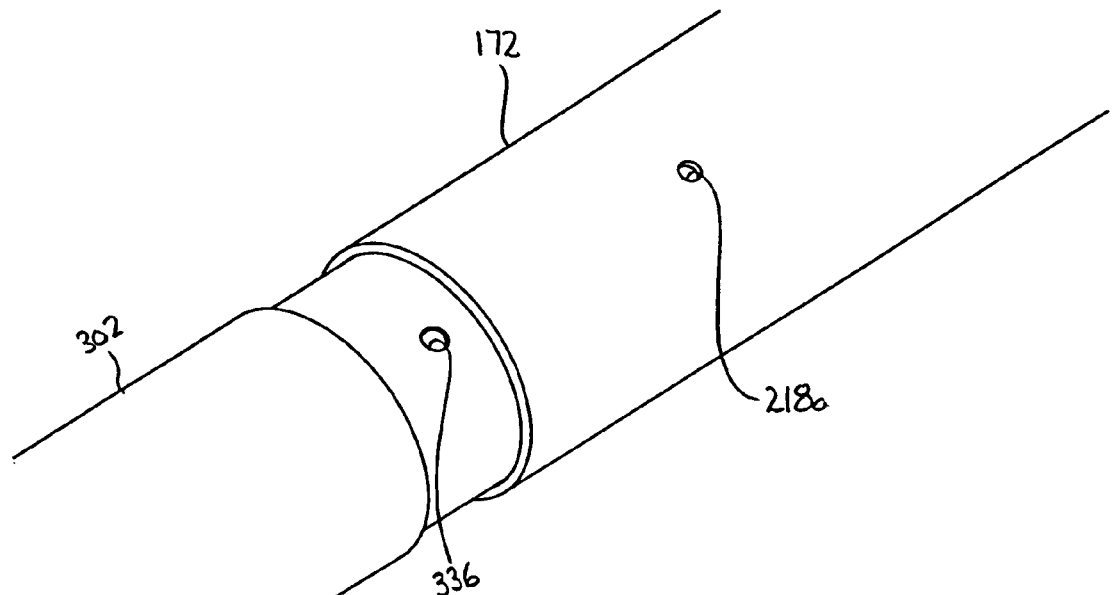
FIG. 47 is a side perspective view of the proximal end of the device SULU and the distal end of the device central body portion shown in FIG. 45 just prior to full attachment of one to the other.
Figure 48:
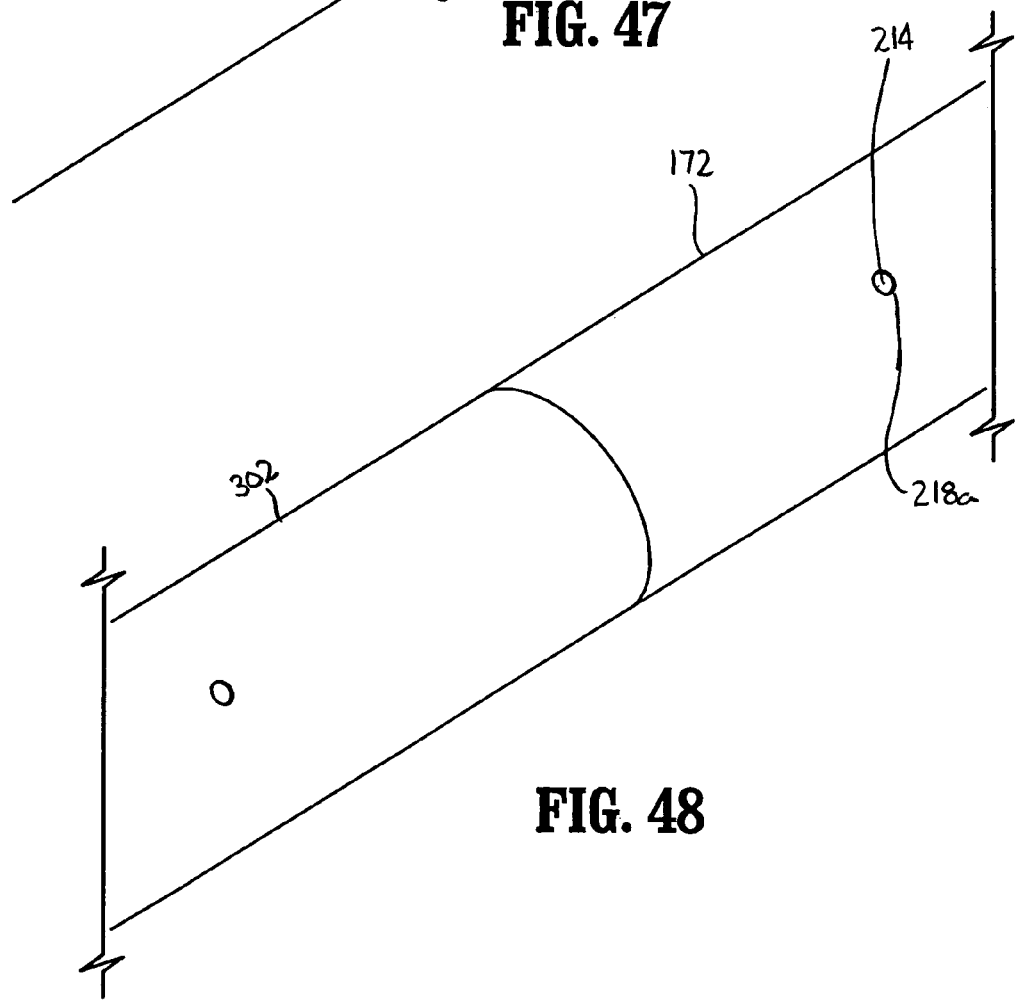
FIG. 48 is a side perspective view of the proximal end of the device SULU and the distal end of the device central body portion with the SULU fully attached to the central body portion.
Figure 49:
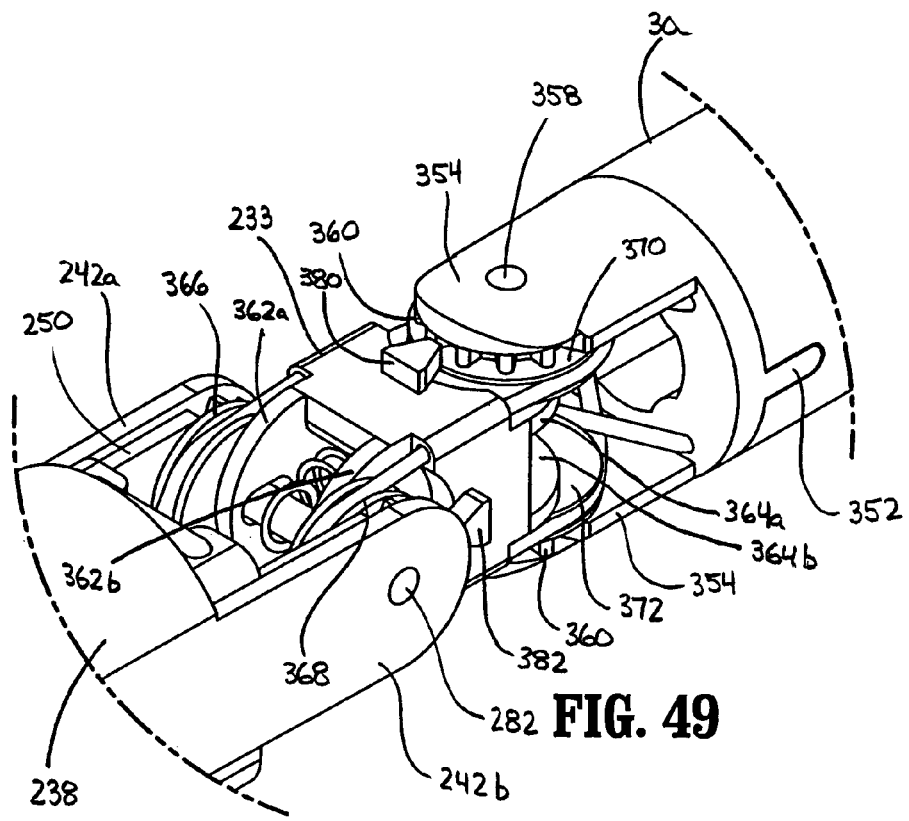
FIG. 49 is an enlarged view of the indicated area of detail shown in FIG. 1.

Outer tube 172 also functions to deform leaf spring 196 on each of links 176a-180 when outer tube 172 is moved from its retracted position to its advanced position. This occurs when the distal end of outer tube 172 advances over leaf springs 196 to force leaf springs 196 towards the top surface of each of links 176a-180 (See FIG. 45). When leaf springs 196 are pressed inwardly by outer tube 172, linkage pins 198 are moved through holes 194 in fingers 192a and 192b to secure a SULU 16 to the distal end of elongated body portion 14 as will be discussed in further detail below.

Referring to FIGS. 9 and 56-58, a pair of snap-fit buttons 220 are positioned to extend through slots 222 (FIG. 9) formed in rotation control member 22. Snap-fit buttons 220 each include an L-shaped body 220a having a projection 220b formed at one end of the body and a finger engagement member 220c on the other end of the body 220a. Each engagement member 220c is accessible by an operator from a location adjacent rotation control member 22 (FIG. 1). Each L-shaped body 220a extends through a respective slot 222 in rotation control member 22 adjacent the other L-shaped body 220a over a top surface of outer tube 172 such that projection 220b engages a sidewall of outer tube 172 opposite engagement member 220c. Snap-fit buttons 220 are formed of a resilient material, e.g., plastic, spring steel, etc. Outer tube 172 includes a pair of diametrically opposed cutouts 224. When outer tube 172 is moved from its retracted to its advanced position, projections 222b of snap-fit buttons 222 snap into cutouts 224 to lock outer tube 172 in its advanced position. Snap-fit buttons 222 can be pressed together by pressing on engagement members 222c to flex projections 222b outwardly and remove projections 222b from cutouts 224 to release outer tube from its advanced position.

Referring to FIGS. 5-8 and 18a-24, SULU 16 includes a proximal body portion 230, a distal tool assembly 232 and an intermediate pivot member 233. Distal tool assembly 232 includes an anvil assembly 234 and a cartridge assembly 236. Anvil assembly 234 includes an anvil body portion 238 and an anvil plate portion 240 (FIG. 19) Anvil plate portion 240 includes along its underside a plurality of staple deforming pockets (not shown) as known in the art. Anvil plate portion 240 is secured to anvil body portion 238 using any known fastening technique, e.g., welding, crimping, etc. In an assembled condition, anvil body portion 238 and anvil plate portion 240 define a gap or cavity 241 therebetween (FIG. 19). The proximal end of anvil body portion 238 includes a pair of hinge members 242a and 242b. The proximal portion of anvil plate portion 240 defines a cam surface 244. An elongated slot 246 extends from the proximal end of anvil plate portion 240 towards the distal end of anvil plate portion 240.

Cartridge assembly 236 includes a carrier portion 250 which defines an elongated support channel 252 dimensioned to receive a staple cartridge 254. Corresponding slots and grooves in the cartridge 254 and carrier portion 250 function to retain cartridge 254 within support channel 252. Staple cartridge 254 includes a plurality of staple slots or pockets 256 for receiving a plurality of fasteners, e.g., staples, and pushers (not shown) as is known in the art. A plurality of spaced apart internal longitudinal slots (not shown) extend through staple cartridge 254 to accommodate upstanding cam wedges 258 of an actuation sled 260. A central longitudinal slot 262 extends along the length of staple cartridge 254 to facilitate linear movement of a knife bar 264 through cartridge 254. Knife bar 264 includes a knife blade 266 and a transverse camming member 268 which is positioned to travel through cavity 241 of anvil assembly 234. Knife bar 264 is positioned proximal to and in contact with actuation sled 260. A pair of holes 270 and 272 are provided in knife bar 264. Hole 270 facilitates engagement or attachment of a firing cable 274 (FIG. 24) to knife bar 264. Hole 272 facilitates engagement or attachment of a retraction cable 276 (FIG. 24) to knife bar 264.

Carrier portion 250 has a pair of hinge members 278a and 278b formed on a proximal end thereof. The proximal surface of each hinge member 278a and 278b can be semi-circular and cam include a series of serrations or teeth 280. The function of teeth 280 will be discussed in further detail below. A pivot pin 282 (FIG. 51) extends between hinge members 242a and 242b and hinge members 278a and 278b such that anvil assembly 234 is pivotal in relation to cartridge assembly 236 between spaced and approximated positions relative to anvil body portion 238.

A guide cap 284 (FIG. 21) or other suitable structure can be provided or secured to the distal end of carrier portion 250. Guide cap 284 or the structure can define for example a pair of tracks 286a and 286b and a central throughbore 288 for receiving and guiding cables of a cable drive system for effecting approximation of the anvil and cartridge assemblies and ejection of staples which will be discussed in further detail below. Guide cap 284 may be secured to carrier portion 250 using any known fastening technique, e.g., snap-fit tabs, screws, adhesives, welds, etc. A channel cover 290 can be secured to each side of carrier portion 250. Each channel cover 290 is secured to a side wall of carrier portion 250 using tabs 292 which are lockingly received in slots 294 formed in carrier portion 250. Channel covers 290 define cable channels, for example, 291a and 291b, for firing cable 274 along sidewalls of carrier portion 250. A pair of cutouts 296a and 296b are formed in carrier portion 250 to facilitate passage of firing cable 274 cable from channels 291a and 291b into cartridge support channel 252.

FIG. 24, shows a suitable cable arrangement or pathway for use with the devices and SULUs disclosed herein. More particularly, firing cable 274 can include a central portion which can extend through hole 270 in knife bar 264. Both ends of cable 274 extend distally from knife bar 264 through suitable channels in or associated with actuation sled 260 and along a central portion of carrier portion 250 of cartridge assembly 236. A first end of firing cable 274 exits carrier portion 250 from throughbore 288 of guide cap 284 and is redirected around track 286a. The second end of firing cable 274 exits carrier portion 250 from throughbore 288 of guide cap 284 and is redirected around guide track 286b. The first and second ends of firing cable 274 extend proximally through cable channels 291a and 291b, respectively, and reenter a proximal portion of carrier portion 250 through cutouts 296a and 296b, respectively, and each passes along opposite sidewalls of carrier portion 250 proximally towards a SULU firing link 310 as will be described in detail below. The arrangement of firing cable 274 is such that when the first and second ends of firing cable 274 are pulled proximally by actuating trigger 20 with firing pawl 48 engaged in firing rack 40, knife bar 264 is pulled distally to approximate the anvil assembly 234 and cartridge assembly 236 and to cause sled 260 to subsequently eject staples from staple cartridge 254.

A retraction cable 276 includes a central portion which operably engages, here, extends through hole 272 in knife bar 264. Respective first and second portions of retraction cable 276 extend proximally from knife bar 264 and towards SULU retraction link 308 as will be describe in detail below (FIG. 24).

Referring to FIGS. 8 and 18a-18e, the SULU proximal body portion 230 (FIG. 8) includes a first fixed outer tube 300, a second movable outer tube 302, an inner shaft 304, a plurality of articulation links 306a-d, a retraction link 308 and a firing link 310. Inner shaft 304 is similar in structure to inner shaft 174 and includes a central hub member 312 (FIG. 18b), a plurality of circumferentially spaced spokes 314 and an outer cylindrical guide surface 316. Adjacent spokes 314 and guide surface 316 define guide channels 318. Each guide channel 318 is dimensioned to slidably receive one of the articulation, retraction and firing links.

Each of the articulation links 306a-d, retraction link 308 and firing link 310 includes a first end having a finger 320 (FIGS. 39 and 40) having a bore 322. Each finger 320 is dimensioned to be slidably received in slot 192 between fingers 192a and 192b of a respective one of links 176-180 of elongated central body portion 14 such that bore 322 is substantially aligned with bore 194 of the respective body portion link. A second end of each of articulation links 306a-d, is adapted to operably engage one end of one of articulation cables 401a and 401b for effecting articulation of the device as will be discussed in further detail below. The proximal end of retraction link 308 and firing link 310 is adapted to engage the proximal end of retraction cable 276 and firing cable 274, respectively. In one embodiment, articulation cables 401a and 401b, retraction cable 276 and firing cable 274 include a proximal eyelet 403 (FIG. 18a) which is pinned to the distal end of a respective link. Alternately, other attachment techniques may be used.

Fixed outer tube 300 can be secured to a distal end portion of inner shaft 304 by a pin 324. Pin 324 extends through outer tube 300 and inner shaft 304 to axially fix outer tube 300 to inner shaft 304. Outer tube 302 can be slidably positioned about a proximal end of inner shaft 304. Inner shaft 304 includes an elongated longitudinal slot 326 extending therethrough. A pin 328 attached to outer tube 302 can be slidably positioned in slot 326, such that outer tube 326 is movable in relation to inner shaft 304 between advanced and retracted positions. A biasing member or spring 330 is positioned in compression between pins 324 and 328 to urge outer tube 302 to its retracted position (FIGS. 18d and 18e). A spring mount 332 may be provided on one or both pins 324 and 328 to facilitate attachment of spring 330 to the pins 324 and/or 328.

Figures 18A, 18B, 18C:
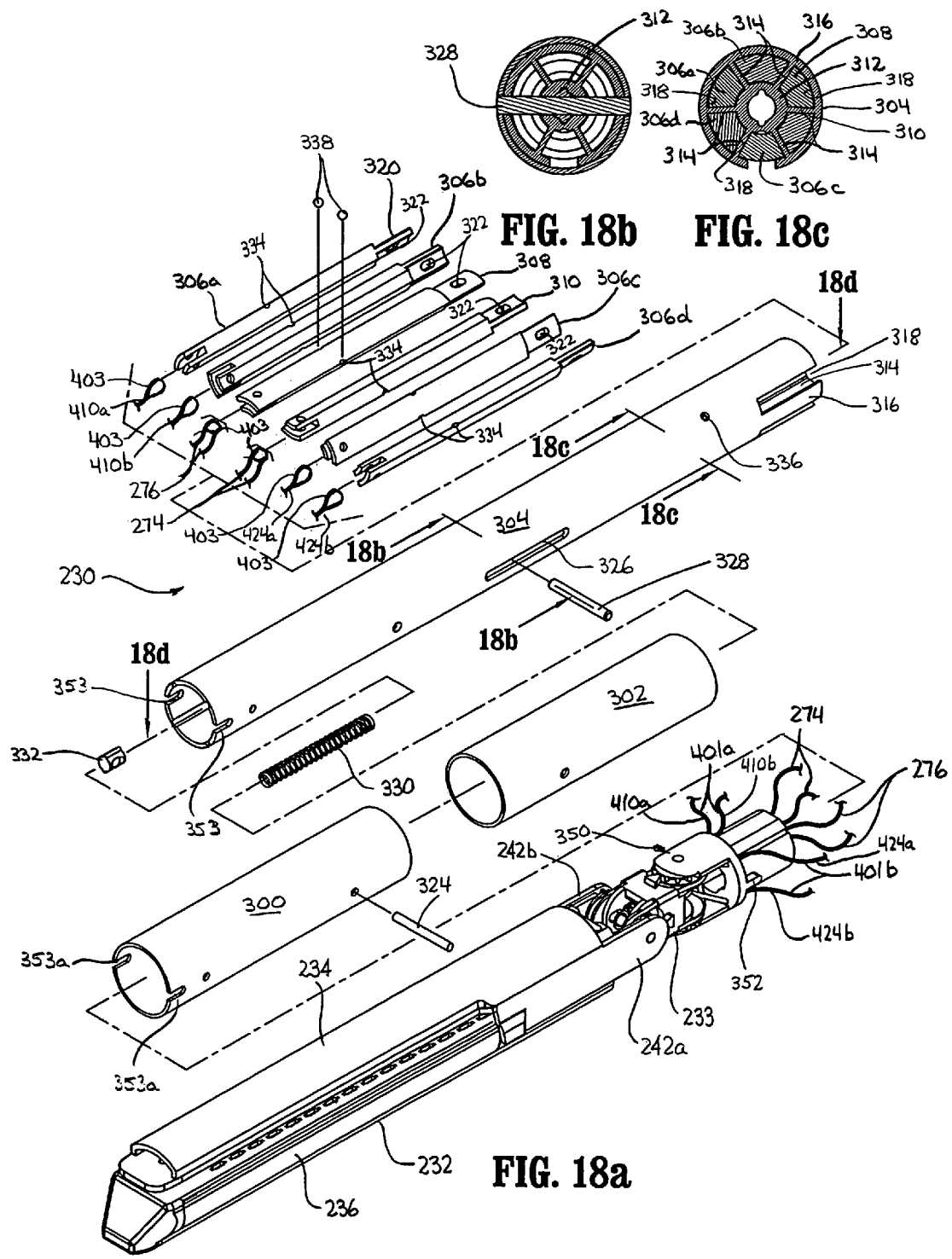
Figure 26:
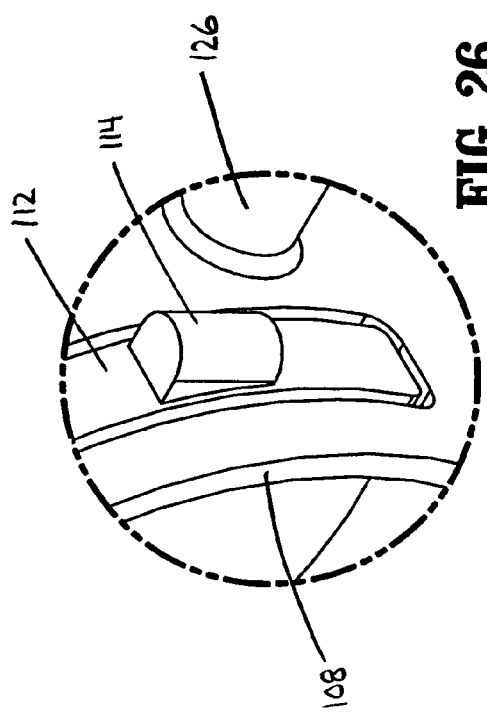
FIG. 26 is an enlarged view of the indicated area of detail shown in FIG. 16.
Figure 28:
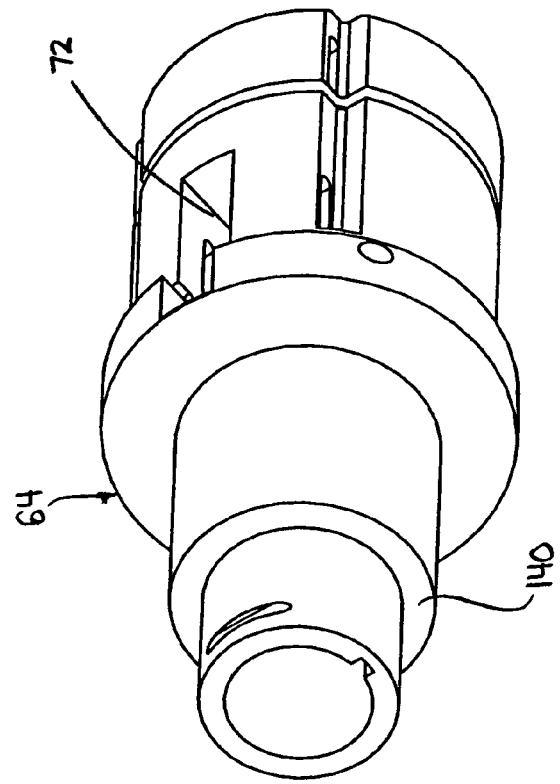
FIG. 28 is an enlarged side perspective view from the distal end of the barrel assembly body portion of the barrel assembly shown in FIG. 15.
Figure 25:
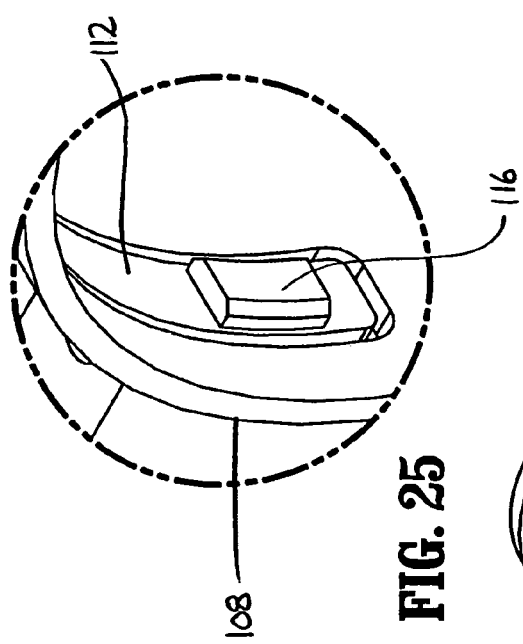
FIG. 25 is an enlarged view of the indicated area of detail shown in FIG. 16.
Figure 27:
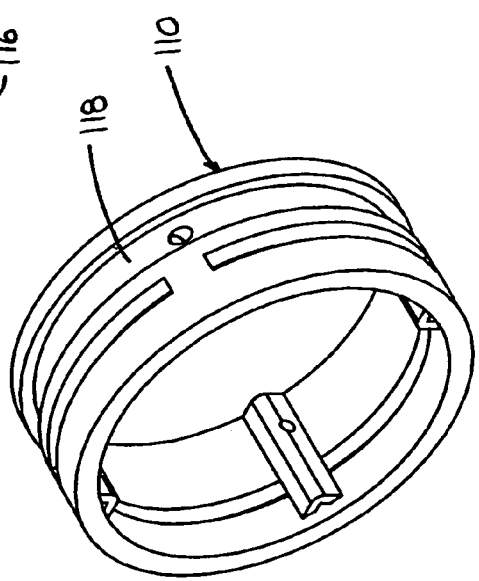
FIG. 27 is an enlarged view of the indicated area of detail shown in FIG. 16.
Figure 29:
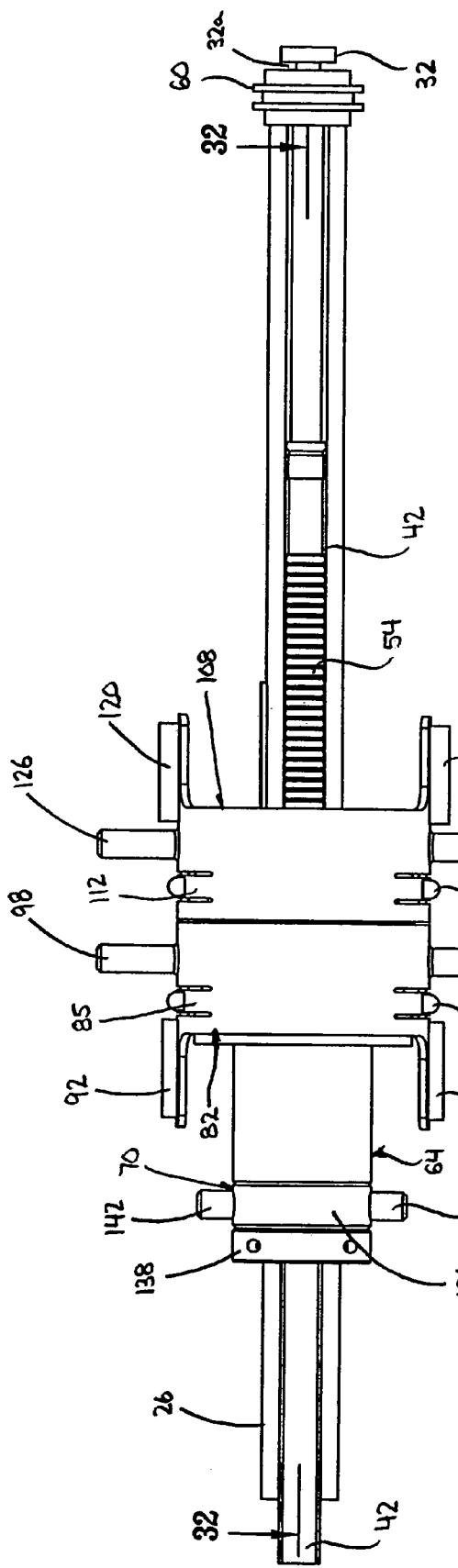
FIG. 29 is a top view of the barrel assembly and spindle shown in FIG. 15.
Figure 30:
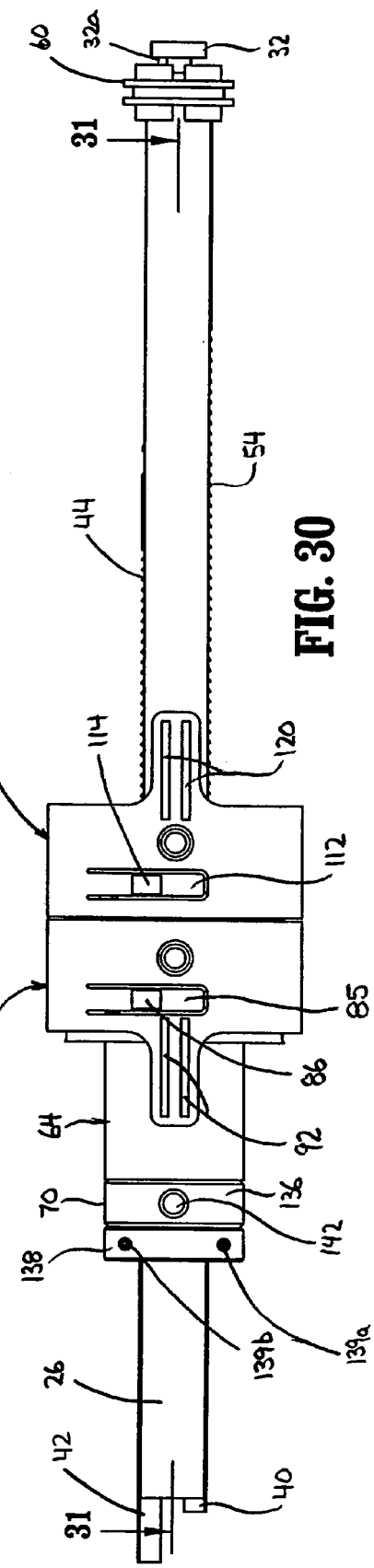
FIG. 30 is a side view of the barrel assembly and spindle shown in FIG. 29.
Figure 31:
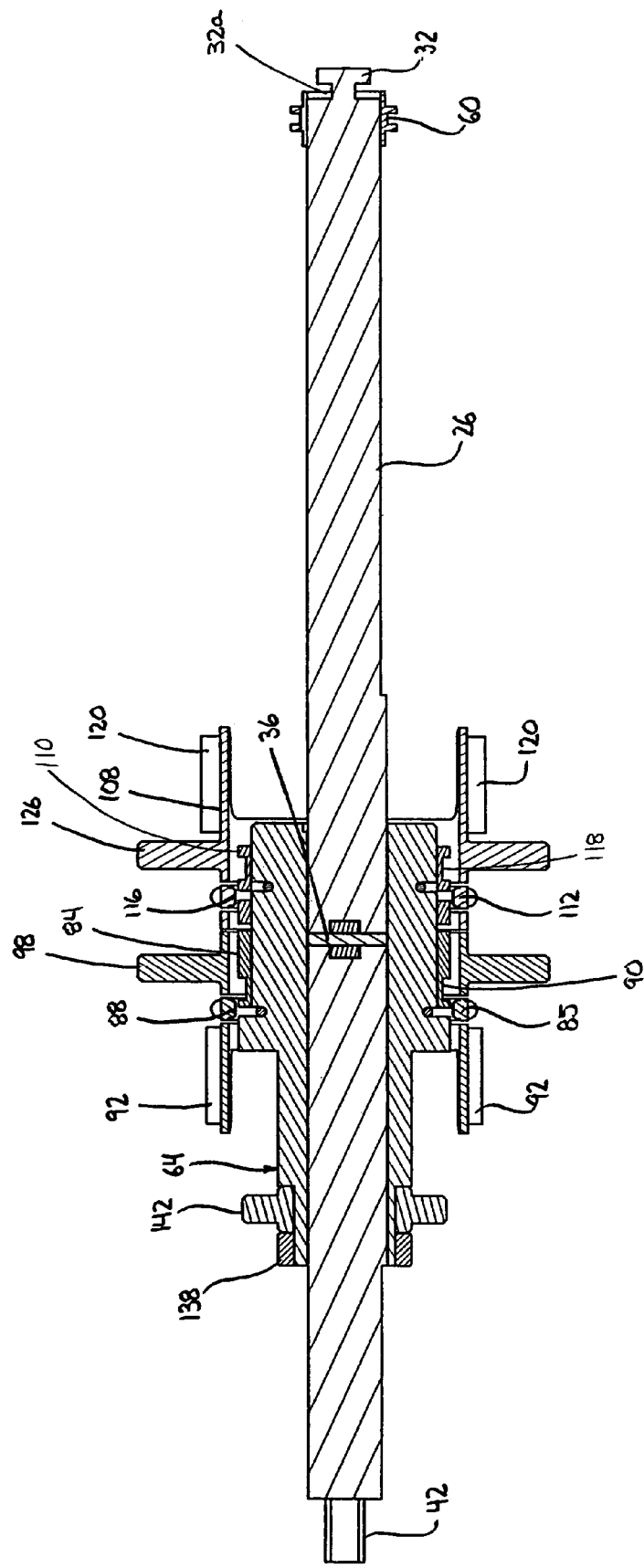
FIG. 31 is a cross-sectional view taken along section lines 31-31 of FIG. 30.
Figure 32:
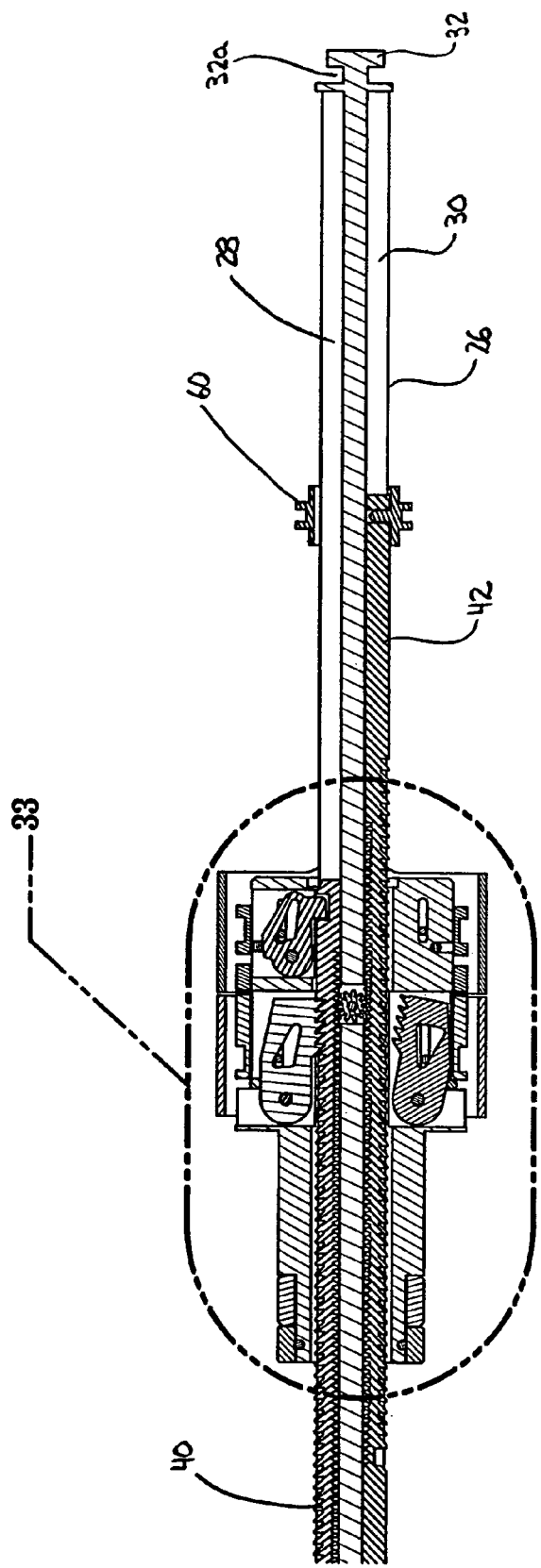
FIG. 32 is a cross-sectional view taken along section lines 32-32 of FIG. 29.

Referring to FIG. 18a, articulation links 306a-d, retraction link 308 and firing link 310 each include at least one concavity 334 formed on a top surface thereof which receives a locking member 338. A single locking member 338 may be positioned to be received in the concavities of two adjacent links. Inner shaft 304 includes an opening 336 positioned adjacent each concavity. Each locking member 338 extends partially through opening 336 and is engageable with an inner surface of movable outer tube 302 when movable outer tube 302 is not in its advanced position. Although locking member 338 is illustrated as being spherical or ball-shaped, it is envisioned that other locking member configurations are suitable for use. Engagement between the inner surface of outer tube 302 and locking member 338 forces each locking member 338 inwardly partially through opening 336 in inner shaft 304 into concavities 334 to axially fix articulation links 306a-d, retraction link 308 and firing link 310 to inner shaft 304. As will be discussed in further detail below, when a SULU 16 is attached to elongated body portion 14 of device 10, movable outer tube 302 is moved by engagement with a distal end of outer tube 172 of elongated body 14 to its advanced position on inner shaft 304 (FIG. 18e). In its advanced position, movable outer tube 302 is positioned distally of locking members 338 and locking members 338 are received within distal ball release openings 218a formed in outer tube 172 of elongated body portion 14 (FIG. 18e). When locking members 338 are positioned within openings 218a, links 306-310 are axially movable in relation to inner shaft 304.

Referring to FIGS. 18a-18e and 51, a mounting member, here shown as hollow mounting member 350, can define a throughbore 351, and can be secured within the distal end of inner shaft 304 by press fitting or using other known attachment techniques, e.g., crimping, adhesives, pins, etc. Mounting member 350 includes a pair of diametrically opposed ribs 352 which are received within slots 353 and 353a formed in inner shaft 304 and outer tube 300, respectively, to rotatably fix mounting member 350 to the distal end of proximal body portion 230 of SULU 16. Mounting member 350 includes a pair of hinge members 354a and 354b. Each hinge member 354a and 354b includes a bore 356 for receiving a pivot member 358, and a semi-circular set of teeth 360 which will be described in further detail below.

Figure 51:
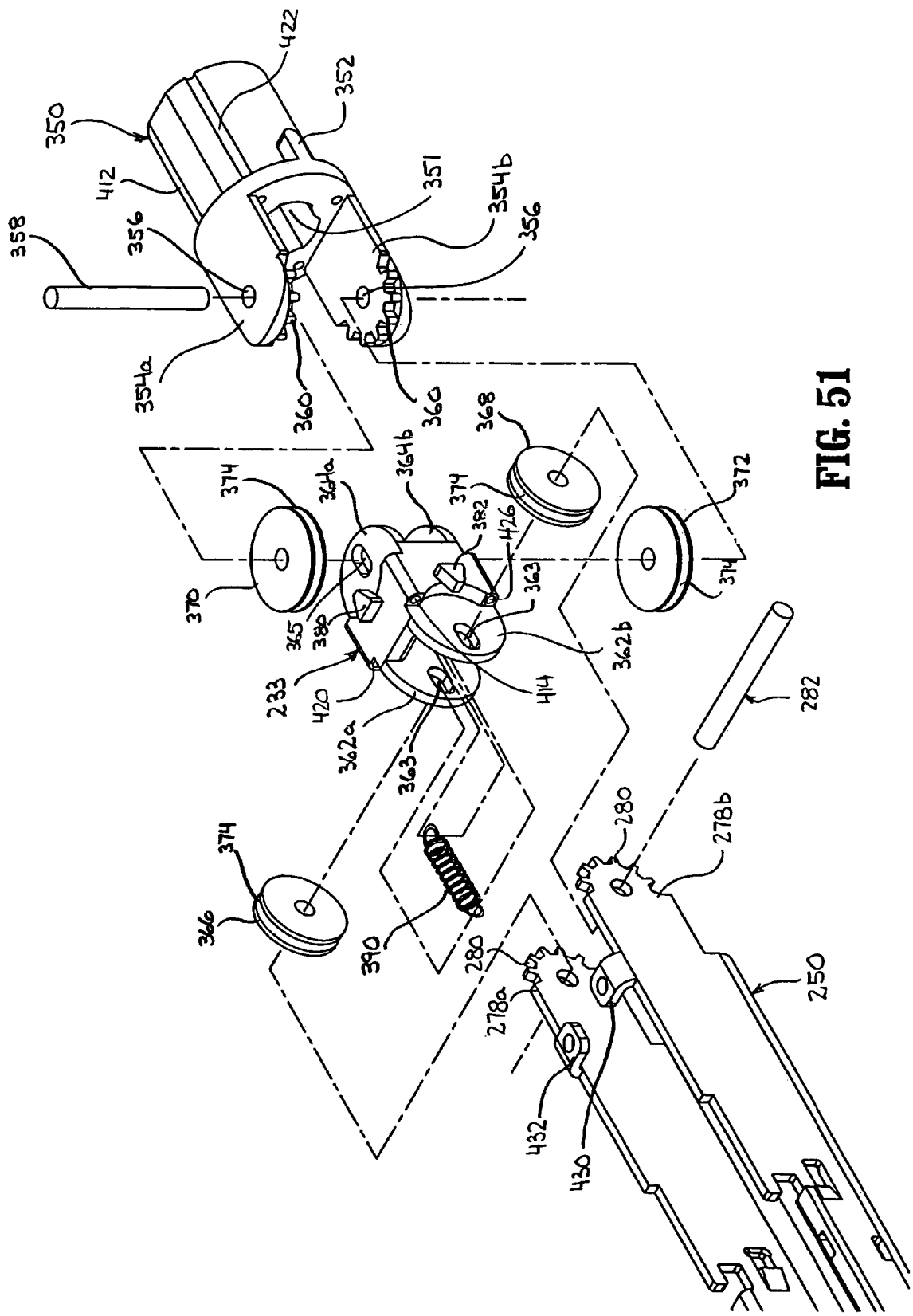
FIG. 51 is a perspective view from the distal end of the proximal end of the cartridge carrier portion, the intermediate pivot assembly and the mounting member of the surgical stapling device shown in FIG. 8, with parts separated.

As shown in FIG. 51, intermediate pivot member 233 includes a first set of hinge members 362a and 362b defining a first horizontal pivot axis and a second set of hinge members 364a and 364b defining a second vertical pivot axis which is offset by about ninety degree from the first pivot axis. Hinge members 362a and 362b each include an elongated slot 363 for receiving pivot pin 282. Hinge members 364a and 364b each include an elongated slot 365 for receiving pivot pin 358. Rotatable pulleys 366 and 368 are secured to hinge members 362a and 362b. Rotatable pulleys 370 and 372 are secured to hinge members 364a and 364b. Each of pulleys 366-372 defines a channel 374 for receiving one of articulation cables 401a and 401b (FIG. 18a). Pivot pin 282 extends between hinge members 242a and 242b of anvil assembly 234, hinge members 278a and 278b of cartridge assembly 236 and hinge members 362a and 362b of pivot member 233 such that anvil assembly 234 is pivotable in relation to cartridge assembly 236 and tool assembly 232 is pivotable in relation to intermediate pivot member 233 about the first horizontal axis. Because slots 363 in hinge members 362a and 362b are elongated, the position of intermediate pivot member 233 is movable in relation to tool assembly 232. Pivot pin 358 extends between pivot members 354a and 354b of hollow mounting member 350 and between pivot members 364a and 364b of intermediate pivot member 233, the latter of which support tool assembly 232. As such, tool assembly 232 is pivotable in relation to elongated body portion 14 about the second vertical axis "Z". Because slot 365 in hinge members 364a and 364b is elongated, the position of intermediate pivot member 233 is movable in relation to mounting member 350 of proximal body portion 230 of SULU 16.

Intermediate pivot member 233 includes a pair of first engagement members 380 positioned on top and bottom surfaces thereof. First engagement members 380 are positioned and configured to engage teeth 360 of hinge members 354a and 354b when pivot pin 358 is pulled to its forwardmost position within pivot slot 363. Engagement between engagement member 380 and teeth 360 locks the angular position of intermediate pivot member 233 in relation to proximal body portion 230 of SULU 16. A pair of second engagement members 382 are positioned on sidewalls of intermediate pivot member 233. Second engagement members 382 are positioned and configured to engage teeth 280 formed on hinge members 278a and 278b of carrier portion 250 when pivot pin 282 is pulled to proximalmost position within pivot slot 363. When second engagement members 382 engage teeth 280, pivotal movement of tool assembly 232 along the y axis in relation to intermediate pivot member 233 is prevented, i.e., the angular position of tool assembly 232 in relation to intermediate pivot member 233 is locked.

Referring to FIGS. 51, 63 and 64, a flexible biasing member or spring is positioned between pivot pins 282 and 358. The biasing member 390, which may be a compression spring, is in compression and is positioned to urge pivot pin 282 to its forwardmost position in slot 363 and urge pivot pin 358 to its proximalmost position in slot 365. In these biased positions, engagement members 380 are disengaged from teeth 360 of SULU proximal portion 230 and engagement members 382 are disengaged from teeth 280 of cartridge carrier portion 250 to facilitate articulation of the various components about the first horizontal axis and the second vertical axis.

Referring to FIGS. 62-64, first engagement members 380 and second engagement members 382 can be brought in engagement with teeth 360 of hinge members 354a and 354b and teeth 280 of hinge members 278a and 278b, respectively, by pulling proximally on articulation actuator 24 to increase the tension in articulation cables 401a and 401b (FIG. 55). When tension in cables 401a and 401b overcomes the compressive force in spring 390, pivot pin 282 moves proximally in slot 363 to move teeth 280 into contact with engagement member 382. Simultaneously, pivot pin 358 moves distally in slot 365 to move engagement member 380 into engagement with teeth 360. As discussed above, when this occurs, the tool assembly 232 is locked at a fixed angular position with respect to intermediate pivot member 233 and intermediate pivot member 233 is locked at a fixed angular position with respect to proximal body portion 230.

Referring to FIGS. 51-55, an articulation cable 401a has a first end 410a attached to articulation link 306a (FIG. 18a). Articulation cable 401a extends from articulation link 306a along and through a channel 412 formed in mounting member 350, diagonally around pulley 370 and through a channel 414 (FIG. 54) in intermediate pivot member 233. Articulation cable 401a exits channel 414 and passes over one side of pulley 368 and extends downwardly through a hole 416 in one side of a bottom portion of the proximal end of carrier portion 250 and back upwardly through a hole 418 on the other side of the proximal end of carrier 250. Articulation cable 401a then passes over one side of pulley 366, extends through a second channel 420 formed through intermediate pivot member 233, and passes around an opposite side of pulley 370. The second end 410b (FIG. 55) of articulation cable 401a extends through and along a second channel 422 (FIG. 55) formed in mounting member 350 and is attached to articulation link 306b.

Figure 50:
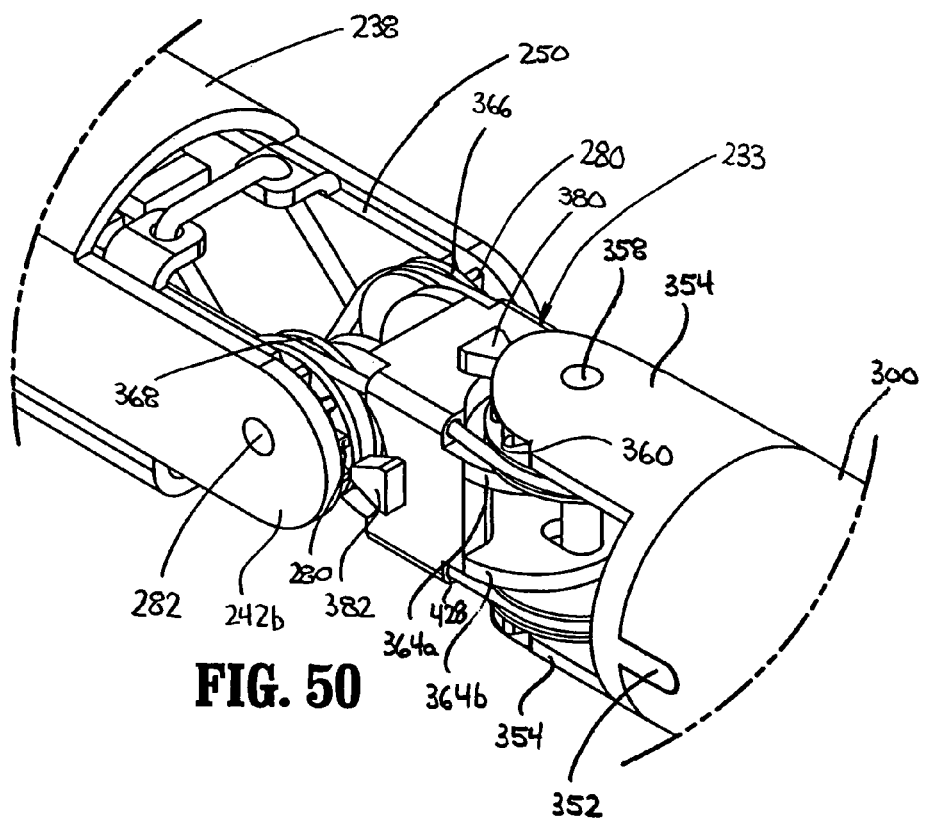
FIG. 50 is an enlarged view of the indicated area of detail shown in FIG. 2.

Articulation cable 401b has a first end 424a attached to articulation link 306c. Articulation cable 401b extends from articulation link 306c along and through a channel 426 (FIG. 55) formed in mounting member 350, diagonally around one side of pulley 372 and through a channel 428 (FIG. 50) formed in intermediate pivot member 233. Articulation cable 401b exits channel 428 and passes upwardly around one side of pulley 368, and through an opening in a bracket 430 formed on one side of a top portion of the proximal end of cartridge carrier 250. Articulation cable 401b extends from bracket 430 through an opening in a second bracket 432 on the other side of the proximal end of cartridge carrier 250 downwardly around one side of pulley 366 and through a channel 434 formed in intermediate pivot member 233. Articulation cable 401b exits channel 434, passes around the other side of pulley 372, and passes through and along a channel 436 formed in mounting member 350. The second end 424b of articulation cable 401b exits channel 436 and is attached to articulation link 306d.

In use, when ends 410a and 410b of articulation cable 401a are pulled rearwardly together, tool assembly 232 is pivoted upwardly about the first horizontal pivot axis, i.e., about pivot pin 282. When ends 424a and 424b of articulation cable 401b are pulled rearwardly together, tool assembly 232 is pivoted downwardly about pivot pin 282. When end 410a of articulation cable 401a and end 424a of articulation cable 401b are pulled rearwardly together, tool assembly 232 and intermediate pivot member 233 will pivot in a counter-clockwise direction as viewed in FIG. 55 about the second vertical axis, i.e., pivot pin 358. The opposite will occur when ends 410b and 424b are pulled rearwardly. Any combination of vertical and horizontal pivoting movements of tool assembly 232 can be achieved by pulling proximally on one or more of the articulation cables.

Each of the articulation cables 401a and 401b are connected to the articulation actuator 24 via articulation links 306a-d of SULU 16, articulation links 176a-d of central portion 14, and non-rigid links 202. By manipulating articulation actuator 24, any combination of movements as described above can be performed such that tool assembly 232 can be articulated in all directions, including those between horizontal and vertical, to at least about ninety degrees. See for example FIGS. 66-74.

Figure 39:
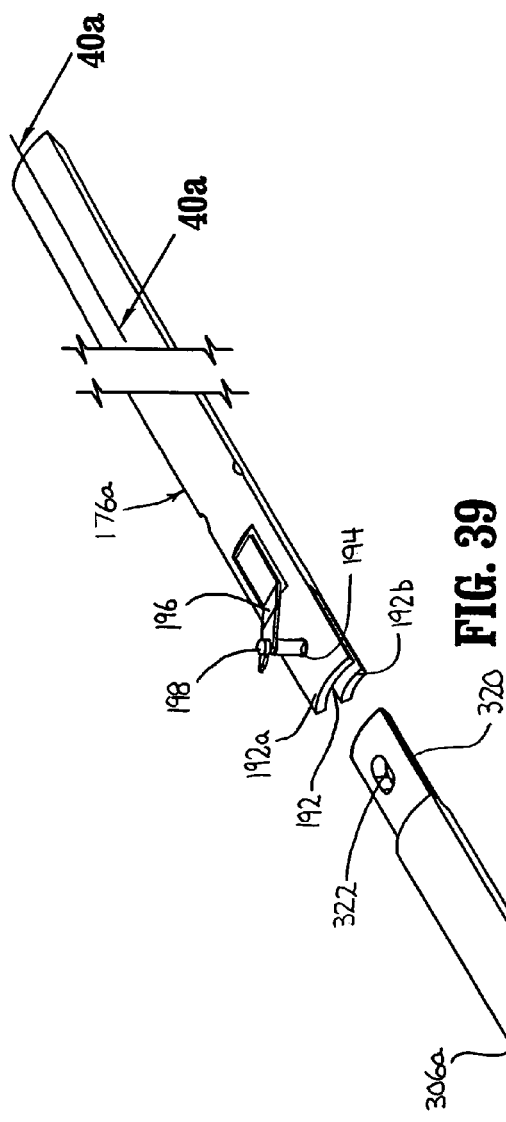
FIG. 39 is a perspective view from the distal end of an articulation link of the central body portion and an articulation link of the SULU prior to attachment.
Figure 56:
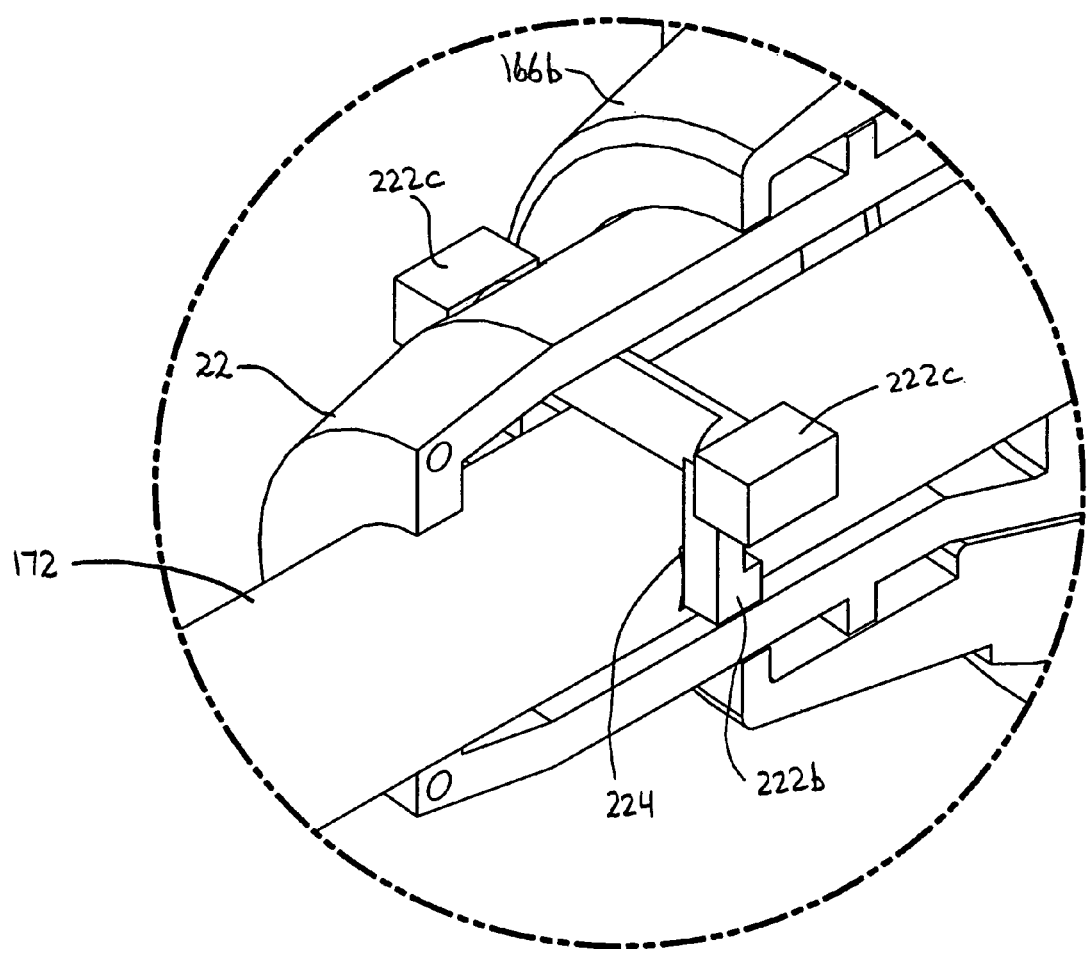
FIG. 56 is an enlarged side perspective view of the distal end of the handle portion and the proximal end of the central body portion of the surgical stapling device with a half-section of the rotation control member removed.
Figure 57:
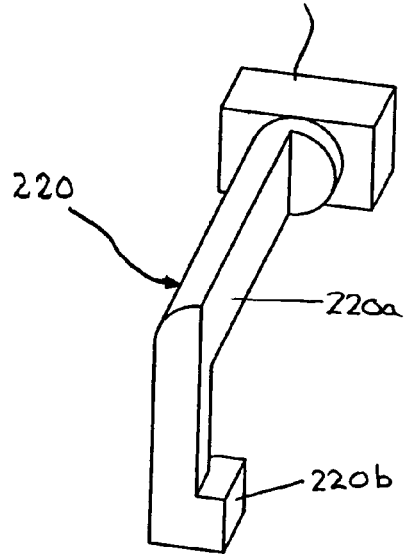
FIG. 57 is a side perspective view from the top of a snap-fit button of the surgical stapling device shown in FIG. 56.
Figure 58:
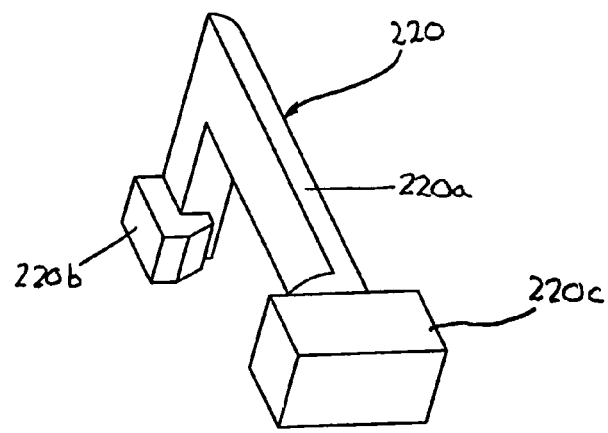
FIG. 58 is a second side perspective view from the top of the snap-fit button shown in FIG. 57.
Figure 65:
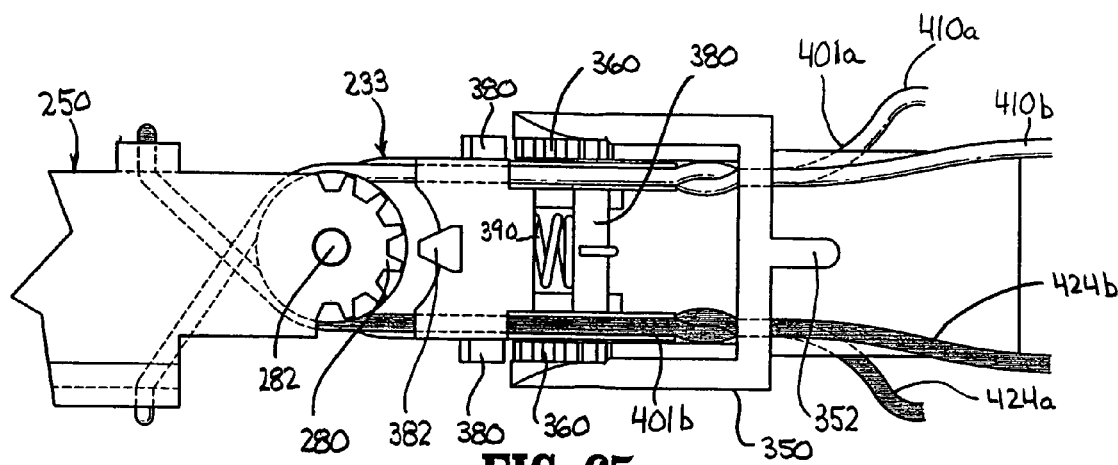
FIG. 65 is a side cutaway view of the carrier portion, intermediate pivot and mounting member of the surgical stapling device shown in FIG. 8 showing the articulation cables partly in phantom and with the SULU in a non-articulated position.
Figure 66:
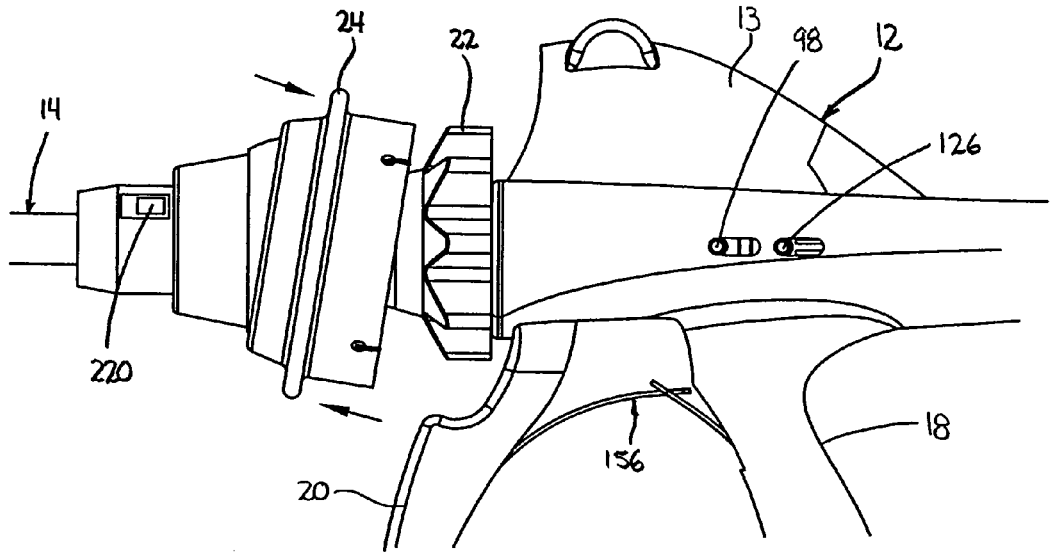
FIG. 66 is a side view of the handle portion of the surgical stapling device shown in FIG. 8 with the articulation actuator moved to a first position to articulate the tool assembly of the SULU to a first orientation.
Figure 67:
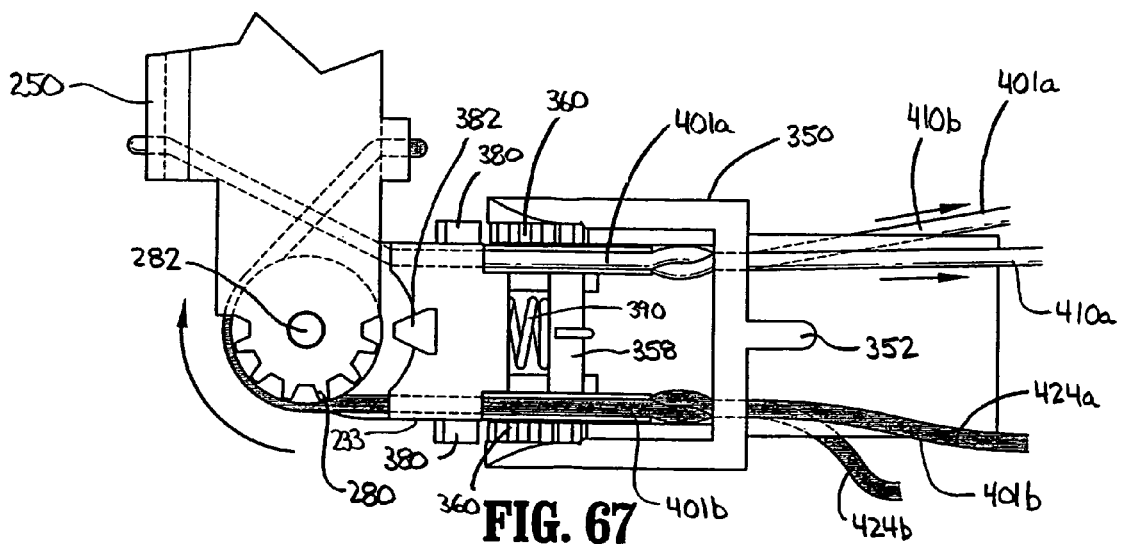
FIG. 67 is a side view of the carrier portion, intermediate pivot and mounting member shown in FIG. 65 after the articulation actuator has been moved to the position shown in FIG. 66.
Figure 68:
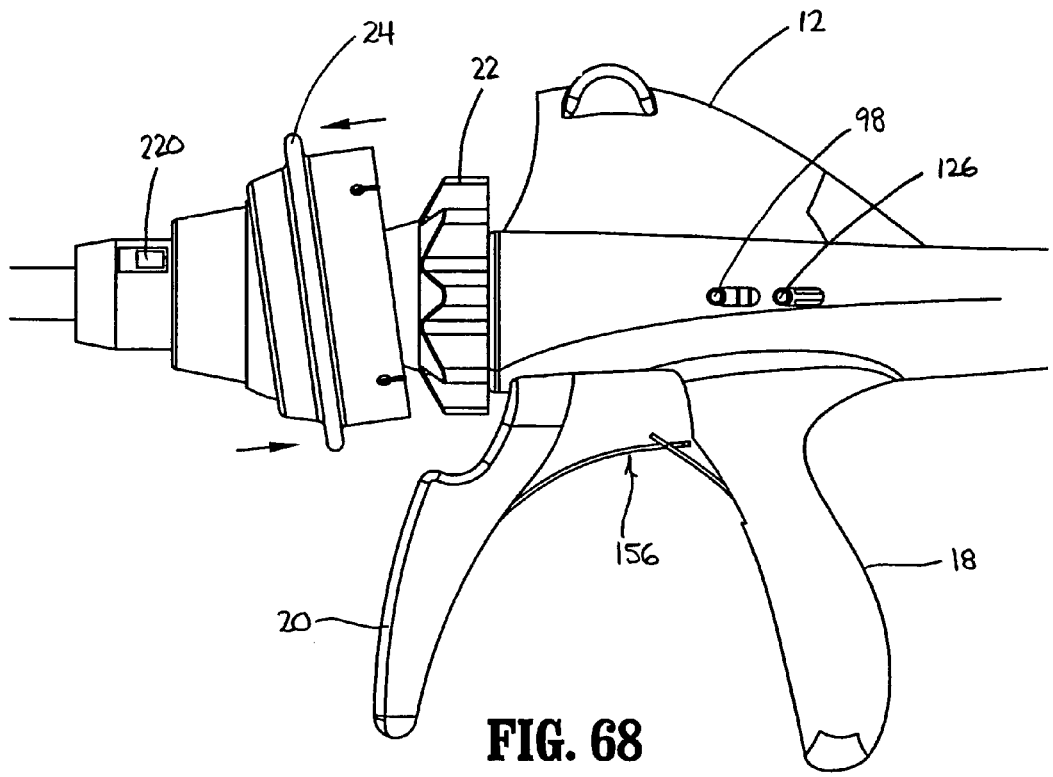
FIG. 68 is a side view of the handle portion of the surgical stapling device shown in FIG. 8 with the articulation actuator moved to a second position to articulate the tool assembly of the SULU to a second orientation.
Figure 69:
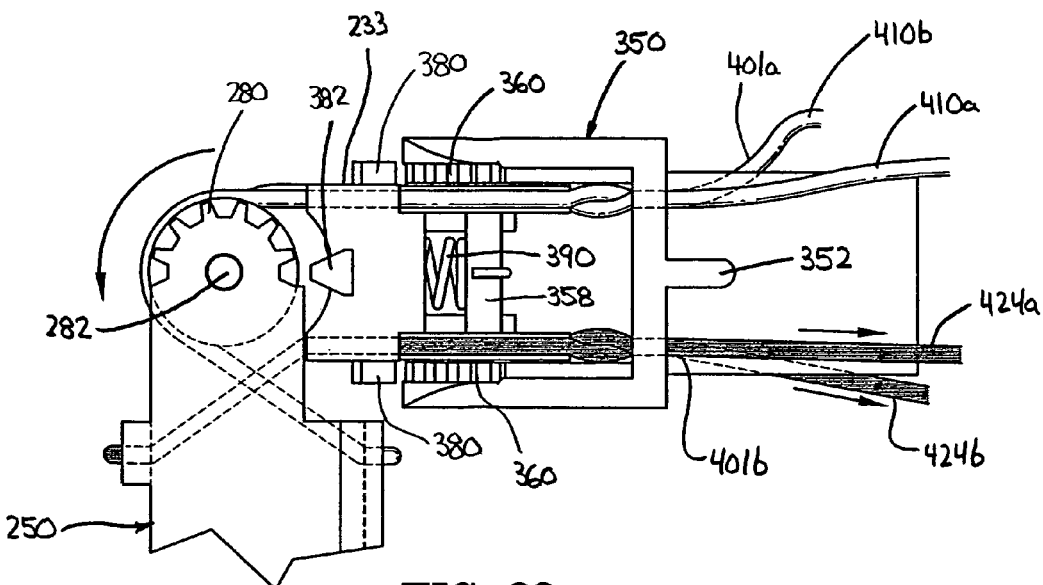
FIG. 69 is a side view of the carrier portion, intermediate pivot, and mounting member as shown in FIG. 65 after the articulation actuator has been moved to the position shown in FIG. 68.

Prior to using surgical stapling device 10, a SULU 16 is secured to the distal end of elongated body portion 14. Referring to FIGS. 39, 40 and 43-48, in order to connect SULU 16 to elongated body portion 14, fingers 320 of SULU articulation links 306a-d, retraction link 308 and firing link 310 are positioned in slots 192 formed on the distal end of elongated body articulation links 176a-d, retraction link 178 and firing link 180, respectively (FIG. 39). Next, elongated body outer tube 172 is moved distally over inner shaft 174. As outer tube 172 moves distally, the distal end of outer tube 172 engages leaf springs 196 to pivot linkage pins 198 downwardly through bores 194 in fingers 192a and 192b of the elongated body links 176a-180 and through bore 322 of fingers 320 of the SULU links 306a-310. Outer tube 172 is advanced distally into engagement with movable outer tube 302 of SULU proximal body portion 230. As outer tube 172 is advanced further, movable outer tube 302 is pushed distally over inner shaft 304 against the bias of spring 330 until locking members 338 of proximal body portion 230 are uncovered by movable outer tube 302 and are received within distal ball release holes 218a (FIG. 18e) of outer tube 172. At this time, locking members 214 of elongated body portion 14 are also received within proximal ball release holes 218b of outer tube 172, and snap-fit protrusions 220 engage cutouts 224 in the proximal end of outer tube 172. Engagement of snap-fit protrusions 220 in cutouts 224 locks outer tube 172 in its advanced position (FIG. 56). The positioning of locking members 338 in distal ball release holes 218a and locking members 214 in proximal ball release holes 218b unlocks the SULU and central body articulation, retraction and firing links in relation to inner shafts 304 and 174 of DLU 16 and elongated body portion 14 to facilitate articulation and firing of the stapling device.

As discussed briefly above, surgical stapling device 10 can be operated as a grasper. Referring to FIG. 33, to utilize device 10 as a grasper, device 10 is maintained in or moved to the unclamped position and second shift ring assembly 68 is moved to its advanced position by sliding outer ring 108 to its advanced position. As discussed above, when this occurs, inner ring 110 will advance to move cam pin 132 within cam slot 52b and allow spring 134 to move grasper protrusion 52a into firing rack cutout 50. Advancement of outer ring 108 also affects advancement of outer ring 82 of first shift ring assembly 66 since outer rings 82 and 108 are adjacent each other. When outer ring 82 is moved to its advanced position, firing pawl 48 engages firing rack 40. Thus, when trigger 20 is actuated or compressed, barrel assembly 62 is moved proximally about spindle 26 to move firing rack 40 proximally. When firing rack 40 moves proximally, firing link 180, SULU firing link 310 and firing cable 274 are pulled proximally. When articulation cable 274 is pulled proximally, knife bar 264 is moved distally such that cam bar 268 engages cam surface 244 of anvil plate 240 and pivots anvil assembly about pivot pin 282 towards cartridge assembly 236 to provide a grasping function relative to tissue in the jaws of tool assembly 232. Since grasping pawl 52 is engaged in cutout 50 of firing rack 40, when trigger 20 is released by an operator and returned to its non-compressed position by spring 156, firing rack 40 will return to its advanced position. When this occurs, pinion 36 will concurrently drive retraction rack to its retracted position to return drive member 264 to its retracted position and move the anvil and cartridge assemblies or jaws 234 and 236, respectively to their open configuration. This process can be repeated to utilize stapling device 10 as a grasper.

When it is desired to eject staples from device 10, grasper pawl 52 is disengaged from firing rack cutout 50 by moving outer ring 108 of shift ring assembly 68 to its retracted position, and moving outer ring 82 of shift ring assembly 66 to the advanced position to engage firing pawl 48 with firing rack 40. Thereafter, movable trigger 20 can be compressed towards stationary handle 18 through an actuation stroke to move firing rack 40 proximally within guide channel 28. As discussed above, movement of firing rack 40 proximally moves firing link 180, firing link 310 and firing cable 274 proximally to move drive member 264 distally within tool assembly 32. It is noted that each actuation stroke of movable trigger 20 effects a predetermined linear movement of drive member 264, e.g., 15 mm. As such, surgical device 10 may be used to fire multiple size SULU's, e.g., 15 mm, 30 mm, 45 mm, 60 mm, etc. The first actuation stroke of movable trigger effects approximation of the anvil and cartridge assemblies 234 and 236. Each actuation stroke thereafter advances drive member 264 approximately 15 mm through tool assembly 32. Thus, to fire a stapler having a 45 mm SULU, movable trigger would have to be moved through four actuating strokes or (N/15+1) actuating strokes, where N is the length of the SULU.

In order to retract drive member 264 within tool assembly 32 to move the cartridge and anvil assemblies to their spaced positions, first shift ring assembly is moved to the retracted position to move retraction pawl 58 into engagement with retraction rack 42. Thereafter, movable handle 20 is moved through a sufficient number of actuation strokes to return drive member 264 through tool assembly 32.

It will be understood that various modifications may be made to the embodiments disclosed herein. For example, it is envisioned that the surgical stapling device disclosed may be used in association with SULU's which are not surgical stapling devices, e.g., graspers, clip appliers, dissectors, electrosurgical sealing devices, etc. As such, the term "firing link" may include any link for effecting actuation of a tool assembly. Further, the SULU may also include tool assemblies other than staplers or those devices which eject a fastener, e.g., grasper, sealing devices (electrosurgical and non-electrosurgical), etc. Moreover, although the stapling device is disclosed as having a removable SULU, the tool assembly and intermediate pivot member may be non-removably fastened to the central body portion of the surgical stapling device. Therefore, the above description should not be construed as limiting, but merely as exemplifications of preferred embodiments. Those skilled in the art will envision other modifications within the scope and spirit of the claims appended hereto.

What is claimed is:

1. A disposable loading unit comprising:
   a tool assembly including a cartridge assembly having a plurality of staples and an anvil assembly, the anvil assembly being movable in relation to the cartridge assembly between spaced and approximated positions;
   a proximal body portion configured to releasably engage a surgical instrument; and
   an intermediate pivot member pivotally secured to the tool assembly about a first pivot axis and pivotally secured to the proximal body portion about a second pivot axis, the first pivot axis being substantially orthogonal to the second pivot axis.

2. A disposable loading unit according to claim 1, wherein the proximal body portion includes a plurality of substantially rigid articulation links, the substantially rigid articulation links being operably connected to the tool assembly by non-rigid articulation links.

3. A disposable loading unit according to claim 1, wherein the tool assembly includes a drive member positioned to translate through the tool assembly to eject the staples form the cartridge assembly.

4. A disposable loading unit according to claim 3, further including a substantially rigid firing link movably supported in the proximal body portion, the substantially rigid firing link being operably connected to the drive member by a non-rigid firing link.

5. A disposable loading unit according to claim 3, wherein the drive member supports a knife blade.

6. A disposable loading unit comprising:
   a tool assembly including a cartridge assembly having a plurality of staples and an anvil assembly, the anvil assembly being movable in relation to the cartridge assembly between spaced and approximated positions;
   a proximal body portion including a plurality of substantially rigid articulation links, the substantially rigid articulation links being operably connected to the tool assembly by non-rigid articulation links; and
   an intermediate pivot member pivotally secured to the tool assembly about a first pivot axis and pivotally secured to the proximal body portion about a second pivot axis, the first pivot axis being substantially orthogonal to the second pivot axis, wherein the substantially rigid articulation links each include proximal engagement structure for releasably engaging a surgical stapling instrument.

7. A disposable loading unit according to claim 6, wherein each of the non-rigid articulation links extends through a channel formed through the intermediate pivot member and is operably engaged with the tool assembly.

8. A disposable loading unit according to claim 7, wherein the plurality of rigid articulation links includes four articulation links, each of the non-rigid articulation links having a first end secured to a first substantially rigid articulation link, a central portion operably associated with the tool assembly and a second end secured to a second substantially rigid articulation link.

9. A disposable loading unit according to claim 8, wherein the central portion of each non-rigid articulation link is operably associated with a proximal end of the cartridge assembly.

10. A disposable loading unit according to claim 6, wherein the proximal engagement structure includes an extension having a bore formed therethrough.

11. A disposable loading unit comprising:
    a tool assembly including a cartridge assembly having a plurality of staples and an anvil assembly, the anvil assembly being movable in relation to the cartridge assembly between spaced and approximated positions;
    a proximal body portion;
    an intermediate pivot member pivotally secured to the tool assembly about a first pivot axis and pivotally secured to the proximal body portion about a second pivot axis, the first pivot axis being substantially orthogonal to the second pivot axis; and
    a substantially rigid firing link movably supported in the proximal body portion, the substantially rigid firing link being operably connected to a drive member by a non-rigid firing link, wherein the non-rigid firing link has a first end connected to the substantially rigid firing link, a central portion extending through the tool assembly and about a guide supported in the distal end of the tool assembly and a second end operably engaged with the drive member, wherein proximal movement of the substantially rigid firing link within the proximal body portion effects distal advancement of the drive member within the tool assembly.

12. A disposable loading unit according to claim 11, further including a substantially rigid retraction link movably supported in the proximal body portion, the substantially rigid retraction link being operably connected to the drive member by a non-rigid retraction link.

13. A disposable loading unit according to claim 12, wherein the non-rigid retraction link operably engages the drive member such that proximal movement of the rigid retraction link effects proximal movement of the drive member within the tool assembly.

14. A disposable loading unit according to claim 13, wherein the non-rigid firing link and the non-rigid retraction link are cables.

15. A disposable loading unit according to claim 12, wherein the proximal end of each of the substantially rigid articulation links and the substantially rigid firing retraction links includes engagement structure for releasably engaging a surgical stapling device.

* * * * *